United States Patent [19]
Beach

[11] Patent Number: 6,156,876
[45] Date of Patent: Dec. 5, 2000

[54] D-TYPE CYCLIN AND USES RELATED THERETO

[75] Inventor: David H. Beach, Huntington Bay, N.Y.

[73] Assignee: Cold Spring Harbor Laboratory, Cold Spring Harbor, N.Y.

[21] Appl. No.: 08/324,526

[22] Filed: Oct. 18, 1994

Related U.S. Application Data

[63] Continuation of application No. 07/888,178, May 26, 1992, abandoned, which is a continuation-in-part of application No. 07/701,514, May 16, 1991, abandoned.

[51] Int. Cl.$^7$ ........................ C07K 14/39; C07K 14/435; C07K 16/14; C07K 16/18
[52] U.S. Cl. .................. 530/350; 530/387.1; 530/388.1; 530/387.9
[58] Field of Search ................................. 435/254.1, 69.1; 536/22.1, 23.1, 23.5; 530/350, 387.1, 388.1, 387.9, 388.85

[56] References Cited

U.S. PATENT DOCUMENTS 5,086,476   2/1992   Bacus et al. .

FOREIGN PATENT DOCUMENTS

WO92/15603   9/1992   WIPO .

OTHER PUBLICATIONS

Bennett, C. F., "Antisense Research," *Science*, vol. 271, p. 434 (1996).
Gura, T., Antisense Has Growing Pains, *Science*, vol. 270, pp. 575–577 (1995).
Lehner, C.F. et al., "Cyclins and cdc2 kinases in Drospophila: genetic analyses in a higher eukaryote," *Ciba Found. Symp.*, vol. 170, pp. 97–109 (1992).
Lerner, "Trapping the Immunological Repertoire to Produce Antibodies of Predetermined Specificity," *Nature*, vol. 299, pp. 592–596 (1982).
Miller, N. et al., "Gene Transfer and Antisense Nucleic Acid Techniques," *Parisitology Today*, vol. 10,
Milligan, J., "Current Concepts in Antisense Drug Design," *J. Medicinal Chemsitry*, vol. 36, No. 14, pp. 1923–1937 (1993).
Pines, J. et al., "Cyclins A and B1 in the Human Cell Cycle," *Ciba Found Symp.*, vol. 170, pp. 187–96 (1992).
Pines, J., "Cyclins adn Cyclin–Dependent Kinases: A Biochemical View," *Biochem. J*, vol. 308, pp. 697–711 (1995).
Rojanasakul, Y., "Antisense Oligonucleotides Therapeutics: Drug Delivery and Targeting," *Advanced Drug Delivery Reviews*, vol. 18, pp. 115–131 (1996).
Stein, C. et al., "Antisense Oligonucleotides as Therapeutic Agents—Is the Bullet Really Magical?," *Science*, vol. 261, pp. 1004–1012 (1993).
Stull, R. et al., "Antigene, Ribozyme and Aptamer Nucleic Acid Drugs: Progress and Prospects," *Pharmaceutical Research*, vol. 12, No. 4, pp. 465–583 (1995).
Weiss, R., "Upping the Antisense Ante," *Science News*, vol. 139, pp. 108–109 (1991).
Westermann, B. et al., "Inhibition of Expression of SV40 Virus Large T–Antigen by Antisense Oligonucleotides," *Biomed. Biochim. Acta.*, vol. 48, pp. 85–93 (1989).
Wu–Pong, S., "Oligonucleotides: Opportunities for Drug Therapy and Research," *Pharmaceutical Technology*, vol. 18, pp. 102–114 (1994).
Xiong, Y. et al., "Molecular Cloning and Chromosomal Mapping of CCND Encoding Human D–Type Cyclins," *Genomics*, vol. 13, No. 3, pp. 575–84 (1992).
Lerner "Tapping the immunological repertoire to produce antibodies of predetermined specificity," Nature vol. 299, pp. 592–596, Oct. 14, 1982.
Lane et al., "A Rapid Antibody Assay System for Screening Hybridoma Cultures," Journal of Immunological Methods, vol. 47, pp. 303–307, 1981.
Draetta et al., "cdc2 protein kinase is complexed with both Cyclin A and B: Evidence for proteolytic inactivation of MPF" *Cell* 56:829–838 (1989).
Evans et al., "Cyclin: A protein specified by maternal mRNA in sea urchin eggs that is destroyed at each cleavage division" *Cell* 33:389–396 91983).
Gautier et al., "Cyclin is a component of maturation–promoting factor from xenopus" *Cell* 60:487–494 (1990).
Gautier et al., "Purified maturation–promoting factor contains the product of a xenopus homolog of the fission yeast cell cycle control gene cdc2$^+$" *Cell* 54:433–439 (1988).
Ghiara et al., "A cyclin B homolog in S. cerevisiae: Chronic activation of the cdc28 protein kinase by cyclin prevents exit from mitosis" *Cell* 65:163–174 (1991).
Goebl and Byers, "Letters to the Editor: Cyclin in fission yeast" *Cell* 54:739–740 (1988).
Hadwiger et al., "A family of cyclin homologs that control the $G_1$ phase in yeast" *Proc. Natl. Acad. Sci. USA* 86:6255–6259 (1989).
Hagan et al., "Cloning and sequencing of the cyclin–related cdc13$^+$gene and a cytological study of its role in fission yeast mitosis" *J. of Cell Science* 91:587–595 (1988).
Hunt, "Cell cycle gets more cyclins" *Nature* 350:462–463 (1991).
Lee and Nurse, "Complementation used to clone a human homologue of the fission yeast cell cycle control gene cdc2" *Nature* 327:31–35 (1987).
Lew et al., "Isolation of three novel human cyclins by rescue of G1 cyclin (Cln) function in yeast" *Cell* 66:1197–1206 (1991).

(List continued on next page.)

*Primary Examiner*—Marianne P. Allen
*Attorney, Agent, or Firm*—Foley, Hoag & Eliot, LLP; Matthew P. Vincent; Anita Varma

[57] ABSTRACT

A novel class of cyclins, referred to as D-type cyclins, of mammalian origin, particularly human origin, DNA and RNA encoding the novel cyclins, and a method of identifying other D-type and non-D type cyclins. Also disclosed are a method of detecting an increased level of a D-type cyclin and a method of inhibiting cell division by interfering with formation of the protein kinase-D type cyclin complex essential for cell cycle start.

9 Claims, 23 Drawing Sheets

OTHER PUBLICATIONS

Matsushime et al., "Colony–stimulating factor 1 regulates novel cyclins during the G1 phase of the cell cycle" *Cell* 65:701–713 (1991).

Motokura et al., "A novel cyclin encoded by a bcl1–linked candidate oncogene" *Nature* 350:512–515 (1991).

Murray et al., "The role of cyclin synthesis and degradation in the control of maturation promoting factor activity" *Nature* 339:280–285 (1989).

Murray and Kirschner, "Cyclin synthesis drives the early embryonic cell cycle" *Nature* 339:275–280 (1989).

Murray and Kirschner, "Dominoes and clocks: The union of two views of the cell cycle" *Science* 246:614–621 (1989).

Nasmyth, "FAR–reaching discoveries about the regulation of START" *Cell Cell:*117–1120 (1990).

Nurse, "Universal control mechanism regulating onset of M–phase" *Nature* 344:503–508 (1990).

Pines and Hunter, "Isolation of a human cyclin cDNA: Evidence for cyclin MRNA and protein regulation in the cell cycle and for interaction with $p34^{cdc2}$" *Cell* 58:833–846 (1989).

Richardson et al., "An essential G1 function for cyclin–like proteins in yeast" *Cell* 59:1127–1133 (1989).

Rosenberg et al., "Rearrangement and overexpression of D11S287E, a candidate oncogene on chormosome 11q13 in benign parathyroid tumors" *Oncogene* 6(3):449–453 (1991).

Surana et al., "The role of cdc28 and cyclins during mitosis in the budding yeast S. cerevisiae" *Cell* 65:145–161 (1991).

Solomon et al., "Letters to the Editor: Cyclin in Fission Yeast" *Cell* 54:738–739 (1988).

Westendorf et al.,"The role of Cyclin B in Meiosis I" *J. of Cell Biology* 108:1431–1444 (1989).

Xiong et al., "Human D–type cyclin" *Cell* 65:691–699 (1991).

```
GCAGTAGCACCGAGCAGCAGAGTCCGCACGCTCCGGCGAGGGCCAGAAGAGCCCGAGGGA      60
GCGCGGGGGCAGCAGAAGGGAGGAGAGCCCAGCCAGCCAGGAGACCCAGGAGACCCAGCCCCTCCCC  120
AGCTGCCCAGGAAGAGCCCCAGCCATGGAACACCAGCTCCTGTGCTGCGAAGTGGAAACC    180
                M  E  H  Q  L  L  C  C  E  V  E  T          12
ATCCGCCGCGCGTACCCCGATGCCAACCTCCTCAACGACCGGGTGCTGCGGGCCATGCTG    240
 I  R  R  A  Y  P  D  A  N  L  L  N  D  R  V  L  R  A  M  L     32
AAGGCCGAGGAGACCTGCGCGCCCTCGGTGTCCTACTTCAAATGTGTGCAGAACGACGTC    300
 K  A  E  E  T  C  A  P  S  V  S  Y  F  K  C  V  Q  K  E  V     52
CTGCCGTCCATGCGGAAGATCGTCGCCACCTGGATGCTGGAGGTCTGCGAGGAACAGAAG    360
 L  P  S  M  R  K  I  V  A  T  W  M  L  E  V  C  E  E  Q  K     72
TGCGAGGAGGAGGTCTTCCCGCTGGCCATGAACTACCTGGACCGCTTCCTGTCGCTGGAG    420
 C  E  E  E  V  F  P  L  A  M  N  Y  L  D  R  F  L  S  L  E     92
CCCGTGAAAAAGAGCCGCCTGCAGCTGCTGGGGGCCACTTGCATGTTCGTGGCCTCTAAG    480
 P  V  K  K  S  R  L  Q  L  L  G  A  T  C  M  F  V  A  S  K    112
ATGAAGGAGACCATCCCCCTGACGGCCGAGAAGCTGTGCATCTACACCGACGCCTCCATC    540
 M  K  E  T  I  P  L  T  A  E  K  L  C  I  Y  T  D  G  S  I    132
CGGCCCGAGGAGCTGCTGCAAATGGAGCTGCTCCTGGTGAACAAGCTCAAGTGGAACCTG    600
 R  P  E  E  L  L  Q  M  E  L  L  L  V  N  K  L  K  W  N  L    152
GCCGCAATGACCCCGCACGATTTCATTGAACACTTCCTCTCCAAAATGCCAGAGGCGGAG    660
 A  A  M  T  P  H  D  F  I  E  H  F  L  S  K  M  P  E  A  E    172
GAGAACAAACAGATCATCCGCAAACGCGCAGACTTCGTTGCCTTGTGTGCCACAGAT      720
 E  N  K  Q  I  I  R  K  H  A  Q  T  F  V  A  L  C  A  T  D    192
```

Fig. 2A

```
GTGAAGTTCATTTCCAATCCGCCCCTCCATGGTGGCAGCGGGGACCGTGGTGGCCGCAGTG    780
 V  K  F  I  S  N  P  P  S  M  V  A  A  G  T  V  V  A  A  V     212
CAAGGCCTGAACCTGAGGAGCCCCAACAACTTCCTGTCCTACTACCGCCTCACACGCTTC    840
 Q  G  L  N  L  R  S  P  N  N  F  L  S  Y  Y  R  L  T  R  F     232
CTCTCCAGAGTGATCAAGTGTGACCCAGACTGCCTCCGGGCCTGCCAGGAGCAGATCGAA    900
 L  S  R  V  I  K  C  D  P  D  C  L  R  A  C  Q  E  Q  I  E     252
GCCCTGCTGGAGTCAAGCCTGCGCCAGGCCCAGCAGAACATGGACCCCAAGGCCGCCGAG    960
 A  L  L  E  S  S  L  R  Q  A  Q  Q  N  M  D  P  K  A  A  E     272
GAGGAGGAAGAGGAGGAGGAGGAGGAGGAGGTGGACCTGGCTTGCACACCCACCGACGTGCCGGAC   1020
 E  E  E  E  E  E  E  E  E  V  D  L  A  C  T  P  T  D  V  R  D    292
GTGGACATCTGAGGGGCCAGGCCAGCAGGGGCGCCACCCCGCAGCCGAGGGGCGGGAGC   1080
 V  D  I  *    (SEQ ID NO. 2)
CGGCCCCAGGTGCTCCACATGACAGTCCCTCCTCCGGAGCATTTGATACCAGAAGGG   1140
AAACCTTCATTCTCCTTGTTTTTTTGCTCTTTTGCTCTTTTCCCCCTTCCATCTC   1200
TGACTTAAGCAAAAGAAAAGATTACCCAAAAAACTGTCTTTAAAGAGAGAGAGAAAA   1260
AAAAAAAAAAAAAAAAAAAAAAAAAAAAAAAAAAAAAAAAAAAAAAAAAAAAAAAA   1320
AAAAA  1325   (SEQ ID NO. 1)
```

Fig. 2B

```
GAATTCCCGCCGGGCTTGGCCAGCTGCTGTGCCACGAGGTGGACCCGGTCCGCAGG        60
                  M  E  L  L  C  H  E  V  D  P  V  R  R
GCCGTGCGCGGGACCGCAACC2GCTCCGAGACGACCGCGTCCTGCAGAACCTGCTCACCATC 120
 A  V  R  D  R  N  L  L  R  D  D  R  V  L  Q  N  L  L  T  I    33
GAGGAGCGCTACCTTCCGCAGTGCTCCTACTTCAAGTGCGTGCAGAAGGACATCCAACCC   180
 E  E  R  Y  L  P  Q  C  S  Y  F  K  C  V  Q  K  D  I  Q  P    53
TACATGCGCAGAATGGTGGCCACCTGGATGCTGGAGGTCTGTGAGGAACAGAAGTGCGAA   240
 Y  M  R  R  M  V  A  T  W  M  L  E  V  C  E  E  Q  K  C  E    73
GAAGAGGTCTTCCCCTCTGGCCATGAATTACCTGGACCGTTTCTTGGCTGGGGTCCCGACT 300
 E  E  V  F  P  L  A  M  N  Y  L  D  R  F  L  A  G  V  P  T    93
CCGAAGTCCCATCTGCAACTCTGGGTGCTGTCTGCATGTTCCTGGCCTCCAAACTCAAA   360
 P  K  S  H  L  Q  L  L  G  A  V  C  M  F  L  A  S  K  L  K   113
GAGACCAGCCCGCTGACCGCGGAGAAGCTGTGCATTTACACCGACAACTCCATCAAGCCT  420
 E  T  S  P  L  T  A  E  K  L  C  I  Y  T  D  N  S  I  K  P   133
CAGGAGCTGCTGGAGTGGGAACTGGTGGTGCTGGGGAAGTTGAAGTGGAACCTGGCAGCT   480
 Q  E  L  L  E  W  E  L  V  V  L  G  K  L  K  W  N  L  A  A   153
GTCACTCCTCATGACTTCATTGAGCACATCTTGCGCAAGCTGCCCCAGCAGCGGGAGAAG  540
 V  T  P  H  D  F  I  E  H  I  L  R  K  L  P  Q  Q  R  E  K   173
CTGTCTCTGATCCGCAAGCATCATGCTCAGACCTTCATTGCTCTGTGTGCCACCGACTTTAAG 600
 L  S  L  I  R  K  H  H  A  Q  T  F  I  A  L  C  A  T  D  F  K  193
TTTGCCATGTACCCACCGTCGATGATCGCAACTGGAAGTGTGGGAGCAGCCATCTGTGGG  660
 F  A  M  Y  P  P  S  M  I  A  T  G  S  V  G  A  A  I  C  G   213
CTCCAGCAGGATGAGGAAGTGAGCTCGCTCACTTGTGACGCCCTGACTGAGCTGCTGGCT  720
 L  Q  Q  D  E  E  V  S  S  L  T  C  D  A  L  T  E  L  L  A   233
```

Fig. 3A

```
AAGATCACCAACACAGACGTGGATTGTCTCAAAGCTTGCCAGGAGCAGATTGAGGCGGTG        780
 K  I  T  N  T  D  V  D  C  L  K  A  C  Q  E  Q  I  E  A  V        253
CTCCTCAATAGCCTGCAGCAGTACCGTCAGGACCAACGTGACGGATCCAAGTCGGAGGAT        840
 L  L  N  S  L  Q  Q  Y  R  Q  D  Q  R  D  G  S  K  S  E  D        273
GAACTGGACCAAGCCAGCACCCCTACAGACGTGCGGGATATCGACCTGTGAGGATGCCAG        900
 E  L  D  Q  A  S  T  P  T  D  V  R  D  I  D  L  *  290 (SEQ ID NO. 4)
GTTCTTTGTGTTTTAGGGTGAAACTTAAAAAAAAATTCTGCCCCCACCTAGATCATATATT     1020
TAAAGATCTTTTAGAAGTGAGAGAAAAAGGTCCTACGAAAACGGAATAATAAAAAGCATT      1080
TGGTGCCTATTTGAAGTACAGCATAAAATGCTTGTATATGCGAACAGTTATTGTTT          1140
GATTATGTAAAAGTAATAGTAAAATTAGGGACCAAATTAGAGGAGACTTTTTTTCATGTTATGAGCTA 1200
TGTATGCCTGCAATATGGACCAAATTAGGGACCAAATTAGAGGAGACTTGTACGCCATTTATCGATGATT 1260
GCACATACACCCCCTTGTAGTATATAATTCAAGGAACTGTGTACGCCATTTATCGATGATT     1320
AGATTGCAAAGCAATGAACTCAACATGAATTGAAATAAGGAGGACATGATGGGAAGG        1380
AGTACAAAACAATCTCTTACTAAGTCAGGAGTGTAGTTGGATCTCTACATTAATGTCCTTCTGCTCT 1440
CAGCCACCTGTTACTAGCTGCTACCTAAAGATGTTTATTTTGCCAGTTGGACACAGGTGATT 1500
TCTACAGTAGCTGCTACCTAAAGATGTTTATTTTGCCAGTTGGACACAGGTGATT          1560
GGCTCCTGGGTTTCATGTTCTGTGACATCCTGGTTCTTCTTCCAAATGCAGTCATTGCA       1620
GACACCACCATATTGCTATCTAATGGGACAAGGTGGCCATAACCAGTTCATTGCA          1680
ATGAAAACGGAGGCAGATGGTAATGTGCCTTGGCCTTGCACAGTTTAGCATTAGCATTAGCATTTGGTG 1740
GTATTTAAAAGGGTAATGTGCCTTGGCCTTGCACAGTTTAGCATTGTTATAAAACCATTCCATTCGAAAAGCA 1800
CTGATTGGCATGTCTCGGTTCCCGAGCGATAGATGGGATGGTTTATGCAGGAATTC         1860
CTTTGAAAAATTGTTCCCGAGCGATAGATGGGATGGTTTATGCAGGAATTC        1911
(SEQ ID NO. 3)
```

Fig. 3B

```
GAATTCCGATCCCCCAGCCCGCCCGCTCTCCGGCCCGTCGCCTGCCTTGGGACTC           60

GCGAGCCCGCACTCCCGCTGTTCGCTGCCCGAGTATGGAGCTGTGTGTTGCGA           120
                                   M  E  L  C  C  E          7

AGGCACCCGGCACGCGCCGGCCCCGGGCGCCGGCGACCCGCTGCTGGGGACCAGCGTGT     180
 G  T  R  H  A  P  R  A  G  P  D  P  R  L  L  G  D  Q  R  V    27
CCTGCAGAGCCTGCTCCGCCTGGAGGAGCGCTACGTACCCCGCGCCTCCTACTTCCAGTG    240
 L  Q  S  L  L  R  L  E  E  R  Y  V  P  R  A  S  Y  F  Q  C    47

CGTGCAGCGGGAGATCAAGCCGCACATGCGGAAGATGCTGGCTTACTGGATGCTGGAGGT    300
 V  Q  R  E  I  K  P  H  M  R  K  M  L  A  Y  W  M  L  E  V    67
ATGTGAGGAGCAGCGCTGTGAGGAGGAAGTCTTCCCCCTGGCCATGAACTACCTGGATCG    360
 C  E  E  Q  R  C  E  E  E  V  F  P  L  A  M  N  Y  L  D  R    87

CTACCTGTCTCTTGCCGTCCCCCACCCCGAAAAGGCGCAGTTGCAGCTCCTGGGTGCGCAT    420
 Y  L  S  C  V  P  P  T  R  K  A  Q  L  Q  L  L  G  A  V  C   107
GCTGCTGGCCCTCCAAGCTGCGCGAGCACCGCCCCTGACCACATCGAAAAACTGTGCATCTA    480
 M  L  A  S  K  L  R  E  T  T  P  L  T  I  E  K  L  C  I  Y   127

CACCGACCACGCTGTCTCTCCCCGCCAGTTGCGGGACTGGGAGGTGCTGGTCCTAGGGAA    540
 T  D  H  A  V  S  P  R  Q  L  R  D  W  E  V  L  V  L  G  K   147
GCTCAAGTGGGACCTGGCTGCTGTGATTGCACATGATTTCCTGGCCTTCATTCTGCACCG    600
 L  K  W  D  L  A  A  V  I  A  H  D  F  L  A  F  I  L  H  R   167

GCTCTCTCTGCCCCGTGACCGACAGGCCTTGGTCAAAAAGCATGCCCAGACCTTTTTGGC    660
 L  S  L  P  R  D  R  Q  A  L  V  K  K  H  A  Q  T  F  L  A   187
CCTCTGTGCTACAGATTATACCTTTGCCATGTACCCGCCATCGATGATCGCCACGGGCAG    720
 L  C  A  T  D  Y  T  F  A  M  Y  P  P  S  M  I  A  T  G  S   207

Fig. 4A
```

```
CATTGGGGCTGCAGTGCAAGGCCCTGGGGTGCCTGCTCCATGTCCGGGGATGAGCTCACAGA    780
 I  G  A  A  V  Q  G  L  G  A  C  S  M  S  G  D  E  L  T  E     227
GCTGCTGGCAGGGATCACTGGCACTGAAGTGGACTGCCTGCGGGCTGCTGTCAGGAGCAGAT    840
 L  L  A  G  I  T  G  T  E  V  D  C  L  R  A  C  Q  E  Q  I     247
CGAAGCTGCACTCAGGGAGAGCCTCAGGGAAGCCGCTCAGACCAGCTCCAGCCCCAGCGCC    900
 E  A  L  R  E  S  L  R  E  A  A  Q  T  S  S  P  A  P           267
CAAAGCCCCCCCGGGGCTCCCAGCCAAGGGCCCAGCCCAGCAGACACTCCTACAGATGT    960
 K  A  P  R  G  S  S  Q  G  P  S  Q  T  S  T  P  T  D  V        287
CACACAGCCATACACCTGTAGCCCCTGGAGAGGCCCTCTGGAGTGGCCACTAAGCAGAGGAGG  1020
 T  A  I  H  L  *   292   (SEQ ID NO. 6)
GGCCGCTGCACCTCCCACCTCCCTGCCTCCCAGGAACCACCACATCTAAGCCTGAAGGGGCG  1080
TCTGTTCCCCTTCACAAAGCCCAAGGGATCTGTTCCTACCCATCCCCGCAGTGTGCACT     1140
AAGGGCCCGGCCAGCAGCGCCTTTCCCAGCCCATGTCTGTGCTAGTGCAGCTCAAGCTCCTCTGCAT  1200
CTGACCAGCAGCGCCTTTCCCAACTCCTTTGAACGCCCCCACCCCAGGCTGATGGGACAGAAT  1260
TGGATACATACCAGCATTCCAAAATGTCTAGTGCCTTCTAAAGTGTGTCCCTTCTAGGGTTATTGC  1320
TTTCAACTGCCAAAATGTCTAGTGCCTTCTAAAATTAATGCATGACACATATGAGGGGGAATAGT  1380
ATTTGGATTGGGCTCCTCTCAGTACTTTGGAGGCCAGAGACGTAGTCCGTGCTGACAGCTGCTCC  1440
CTAGATGGGAGGGGCCTAGGCTCAGTGATTGACAGGAAGCTATAAATTCCTCTCTTTGCTTTTCT  1500
GCTCAGTTCTTCCTGTGTTAAGAGGACGTAGTGGGTCCTGGCCATCCCACAAGTGGTGG       1560
TTGCTTTGAGCACAACTTTGCTGTTTTCCTCCTGTCTACTGGCAAAAGGATCTTTGTGGCCA    1620
TAACCCTGGTTGCTATAGCCTGGGGTGGGTCATGCGGATGCCTCTCCCATTGTCCCTCTGCCCCA 1680
AGGAGCTGCTATAGCCTGGGGTGGGTCATGCGGATGCCTCTCCCATTGTCCCTCTGCCCCA    1740
TCCTCCAGCAGGGAAAATGCAGGATGCTCTTTCCTAAGGCTGCGAGCCCTGTCTAGAGA       1800
GGGAGGCAAGCCTGTTGACACAGGTCTCTTTCCTAAGGCTGCAAGTTTAGGCTGGCCCC       1860
AGGACCATCATCCTACTCCTACTGTAATAAAGATGATTGTGGGAATTC 1962 (SEQ ID NO. 5)
```

```
CYCD1-Hs   QLCCEVETIRRAYPDANLLNDRVLRAMLKAEETCAPSVSYFKCVQKEVLPSMRKIVATWMLEVCEEQKCEEEVFPLAMNYLDRFL
           SLEPVKKSRLQLLGATCMF
CYCA-Hs    SIVLEDEKPVSVNEVPDYHEDIHTYLR-EMEVKCKPKVGYMKKQP-DITNSMRAILVDWLVEVGEEYKLQNETLHLAVNYIDRFL
           SSMSVLRGKLQLVGTAAML
CYCA-Dm    KELPPRNDRQRFLEVVQYQMDILEYFR-ESEKKHRPKPRYMRRQK-DISHNMRSILIDWLVEVSEEYKLDTETLYLSVFYLDRFL
           SQMAVVRSKLQLVGTAAMY
CYCB1-Hs   VNDVDAEDGADPNLCSEYVKDIYAYLR-QLEEEQAVRPKYLLGR--EVTGNMRAILIDWLVQVQMKFRLLQETMYMTVSIIDRFM
           QNNCVPKKMLQLVGTAMF
CDC13-Sp   WDDLDAEDWADPLMVSEYVVDIFEYLN-ELEIETMPSPTYMDRQ-KELAWKMRGILTDWLIEVHSRFRLLPETLFLAVNIIDRFL
           SLRVCSLNKLQLVGIAALF
CLN1-Sc    IELSNAELLTHYETIQEYHEEISQNVL-VQSSKTKPDIKLIDQQPEMNPHQTREAIVTFLYQLSVMTRVSNGIFFHSVRFYDRYC
           SKRVVLKDQAKLVVGTCLW
CLN3-Sc    PNLVKRELQAHHSAISEYNNDQLDHYF-RLSHTERPLYNL3NSQPQVNP-KMRFLIFDFIMYCHTRLNLSTSTLFLTFTILDKYS
           SRFIIKSYNYQLLSLTALW
CYCB1-Hs   VASKMKETIPLTAEKLCIYTDGSIRPEELLQMELLLVNKLKWNLAAMTPHDFIEHFLSKMPEAEENKQIIRKHAQTFVALCATDV
           KFISNPPSMVAAGSVVAAV     (SEQ ID NO. 7)
CYCA-Hs    LASKFEEIYPPEVAEFVYITDDTYTKKQVLRMEHLVLKVLTFDLAAPTVNQFLTQ--YFLHQQ2NCKVESLAMFLGELSLIDAT--
           PYLKYLPSVIAGAAFHLAL     (SEQ ID NO. 8)
CYCA-Dm    IAAKYEEIYPPEVGEFVFLTDDSYTKAQVLRMEQVILKILSFDLCTPTAYVFINT-YAVLCDMPEKLKYMTLYISELSLMEGE--
           TYLQYLPSLMSSASVALAR     (SEQ ID NO. 9)
CYCB1-Hs   IASKYEEMYPPEIGDFAFVTDNTYTKHQIRQMEMKILRALNFGLGRPLPLKFLRR-ASKIGEVDVEQHTLAKYLMELTMLDYD--
           -MVHFPPSQIAAGAFCLAL     (SEQ ID NO. 10)
CDC13-Sp   IASKYEEVMCPSVQNFVYMADGGYDEEEILQAERYILRVLEFNLAYPNPMNFLRR-ISKADFYDIQTRTVAKYLVEIGLLDHK--
           -LLPYPPSQQCAAAMYLAR     (SEQ ID NO. 11)
CLN1-Sc    LAAKTWG25RLSELVHYCGGSDLFDESMFIQMERHILDTLNWDVYEPMINDYI         (SEQ ID NO. 12)
CLN3-Sc    ISSKFWD3RMATLKVLQNLCCNQYSIKQFTTMEMHLFKSLDWSI2SATFDSYI        (SEQ ID NO. 13)
```

Fig. 5A

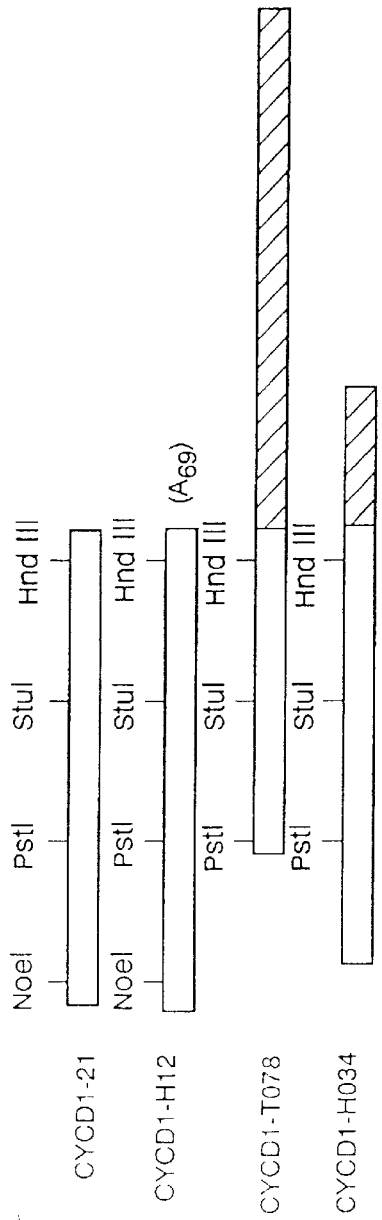
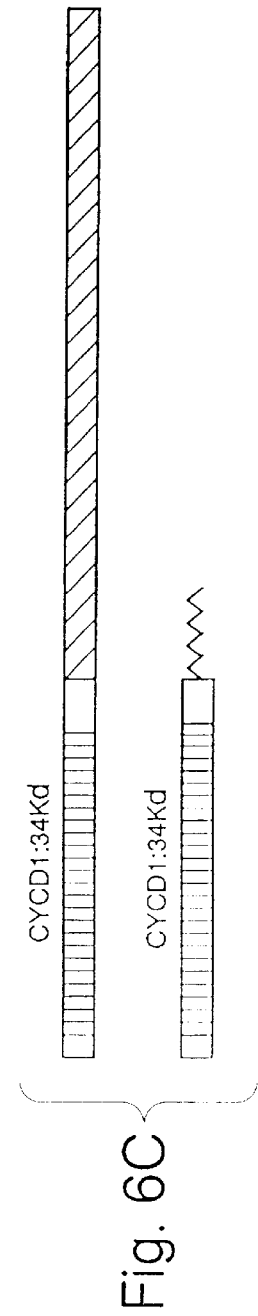

```
CYCD1-21      ....CCCAAAAACTGTCTTT     cDNA (Glioblastoma) (SEQ ID NO. 14)
CYCD1-H12     ....CCCAAAAACTGTCTTTTAAAGAGAGAGAGAGAGAAAAAATAGTATT (SEQ ID NO. 15)
CYCD1-H034    ....CCCAAAAACTGTCTCTTTAAAGAGAGAGAGAGAGAGAGAAAAAA-TAGTATT
CYCD1-T078    ....CCCAAAAACTGTCTCTTTAAAGAGAGAGAGAGAGAGAGAAAAAAAAAATAGTATT
CYCD1-G068    ....CCCAAAAACTGTCTCTTTAAAGAGAGAGAGAGAGAGAGAAAAAAAAAATAGTATT
CTCD1-H034    TGCATAACCCTGAGCGGTGGGGGAGGAGGGTT....  cDNA (HeLa)xxSEQ ID NO. 16)
CYCD1-T078    TGCATAACCCTGAGCGGTGGGGGAGGAGGGTT....  cDNA (Teratocarcinoma) (SEQ ID NO. 17)
CYCD1-G068    TGCATAACCCTGAGCGGTGGGGGAGGAGGGTT....  genomic (liver)  (SEQ ID NO. 18)
```

```
CYCD1-HS  MEHQLLCCEVETI-RRAYPDANLL-NDRVLRAMLKAEETCAPSVSYFKCVQKEVLPS
CYL1-Mm   MENQLLCCEVETI-RRAYPDTNLL-NDRVLRAMLKTEETCAPSVSYFKCVQKEIVPS
CYCD2-Hs  MELLCHEVDPVRRAVRDRNLLR-DDRVLQNLLTIEERYLPQCSYFKCVQKDIQPY
CYL2-Mm
CYCD3-Hs  MELLCCEGTRHAPRAGPDPRLLGDQRVLQSLLRLEERYVPRASYFQCVQREIKPH
CYL3-Mm
CYCA-Hs
CYCB1-HS
CYCB2-Hs
CYCC-Hs
CYCE-HS
```

Fig. 7A

```
         HCND11     HCND12                                          HCND13
MRKIVATWMLEVCEEQKCEEOKCEEEVFPLAMNYLDRFLSLEPVKKSRLQLLGATCMFVASKMKETIPLTAEKLCIYTDGSIRPEELLQMELLIVNKLKWNLAAMTPHDFI
MRKIVATWMLEVCEEQKCEEEVFPLAMNYLDRFLSLEPLKKSRLQLLGATCMFVASKMKETIPLTAEKLCIYTDNSIRPEELLQMELLIVNKLKWNLAAMTPHDFI
MRRMVATWMLEVCEEQKCEEEVFPLAMNYLDRFLAGVPTPKSHLQLLGAVCMFLASKLKETSPLTAEKLCIYTDNSIKPQELLEWELVVLGKLKWNLAAVTPHDFI
MRRMVATWMLEVCEEQKCEEEVFPLAMNYLDRFLAGVPTPKTHLQLLGAVCMFLASKLKETIPLTAEKLCIYTDNSVKPQELLEWELVVLGKLKWNLAAVTPHDFI
MRKMLAYMLEVCEEQRCEEEVFPLAMNYLDRYLSCVPTRKAQLQLLGAVCMLLASKLRETTPLTIEKLCIYTDHAVSPRQLRDWEVLVLGKLKWDLAAVIAHDFL
MRKMLAYMLEVCEEQRCEEDVFPLAMNYLDRYLSCVPTRKAQLQLLGTVCILLASKLRETTPLTIEKLCIYTDQAVAPWQLREWEVIVLGKLKWDLAAVIAHDFL
MRAILVDWLVEVGEEYKLQNETLHLAVNYIDRFLSSMSVLRGKLQLVGTARMLLASKFEEIYPPEVAEFVYITDDTYTKKQVLRMEHLVLKVLTFDLAAPTVNQFL
MRAILIDWLVQVQMKFRLLQETMYMTVSIIDRFMQNNCVPKKMLQLVGVTAMFIASKYEEMYPPEIGDFAFVTDNTYTKHQIRQMEMKILRALNFGLGRPLPLHFL
MRAILVDWLVDWLVQVHSKFRLLQETLYMCVGIMDRFLQVQPVSRKKLQLVGITALLLASKYEEMFSPNIEDFVYITDNAYTSSQIREMETLIIKELKFELGRPLPLHFL
LQIFFTNVIQALGEHLKLRQQVIATATVYFKRFYARYSLKSIDPVLMAPTCVFLASKVEE16LKTRFSYAFPKEFPYRMNHILECEFYLLELMDCCLIVYHPYRPL
MRAILLDWLMEVCEVYKLHRETFYLAQDFFDRYMA2ENVVKTLLQLIGISSLFIAAKLEEIYPPKLHQFAYTDGACSGDEILTMELMIMKALKWRLSPLTIVSWL
                                             Cyclin Box
```

Fig. 7B

```
EHFLSKMPEAEENKQIIRKHAQTFVALCATDVKFISN  (SEQ ID NO. 25)
EHFLSKMPEAEDNKQTIRKHAQTFVALCATDVKFISN  (SEQ ID NO. 26)
EHILRKLPQQREKLSLIRKHAQTFIALCATDFKFAMY  (SEQ ID NO. 27)
EHILRKLPQQKEKLSLIRKHAQTFIALCATDFKFAMY  (SEQ ID NO. 28)
AFILHRLSLPRDRQALVKKHAQTFLALCATDYTFAMY  (SEQ ID NO. 29)
ALILHRLSLPSDRQALVKKHAQTFLALCATDYTFAMY
```

Fig. 7C

```
CYCD1-Hs  PPSMVAAGSVVAAVQGLNLRSPNNFLSYYRLTRFLSRVIKCDPDCLRACQEQIEALLESSLRQAQQNMDPKA-AEEEEEEEEVDLACTPTDVRDVDI*
(SEQ ID NO. 19)

CYL1-Mm   PPSMVAAGSMVAAMQGLNLGSPNNFLSRYRTTHFLSRVIKCDPDCLRACQEQIEALLESSLRQAQQNVDPKA-TEEEGEVEEEAGLACTPTDVRDVDI*
(SEQ ID NO. 20)

CYCD2-Hs  PPSMIATGSVGAAICGLQQDEEVSSLTCDALTELLAKITNTDVDCLKACQEQIEAVLLNSLQQYRQDQRD------GSKSEDELDQASTPTDVRDIDL*
(SEQ ID NO. 21)

CYL2-Mm   PPSMIATGSVGAAICGLQQDDEVNTLTCDALTELLAKITHTDVDCLKACQEQIEALLLNSLQQFRQEQHNA------GSKSVEDPDQATTPTDVRDVDL*
(SEQ ID NO. 22)

CYCD3-Hs  PPSMIATGSIGAAVQGLGACS----MSGDELTELLAGITGTEVDCLRACQEQIEAALRESLREAAQTSSSPAPKAPRGSSSQGPSQTSTPTDVTAIHL*
(SEQ ID NO. 23)

CYL3-Mm   PPSMIATGSIGAAVIGLGACS----MSADELTELLAGITGTEVDCLRACQEQIEAALRESLREAAQTAPSPVPKAPRGSSSQGPSQTSTPTDVTAIHL*
(SEQ ID NO. 24)
```

Fig. 7D

```
TGATCAAGTTGACACTCAATATTAACCCTCATAGACTGTGATCCCTATGTTGCTGCCTTC      60
CCTCGTTTCTATTGCTCTCTTTGGCCCCAACCCAAATAAGGTTCCTTGGACACACTAAAGA    120
AGGAGGTGGAGTTCGAAGGGAGGAGAGATGTGAGCGAGGCAGGCAGGAAGCTCTGCTC       180
GCCCACTGCCCAATCCTCCACCTCTGTCTTCTCCTCCACCTCTGTCTCTGCCCTCCACCTCTC 240
CTCTGAAAACCCCCTATTGAGCCCAAAGGAGAGATGAGGGAATGCTTTTGCCTTCCCC       300
CTCCAAAACAAAAACAAAAACACACTTTCCAGTCCAGTAGGGTAGACCCAGAGAAAGCAGGGAGTGAG 360
GGGTCACAGAGCTGGCCATGCAGCTGCTGGGCTGTGAGGTAGACCCGGTCCTCAGAGCCA    420
                M  Q  L  L  G  C  E  V  D  P  V  L  R  A
CGAGGGACTGCAACTACTCCAAGTTGACCTGTCCTGAAGAACCTGCTTGCTATCAAGA       480
 T  R  D  C  N  L  L  Q  V  D  R  V  L  K  N  L  L  A  I  K
AAGCGCTACCTTCAGTAATGCTCCTACTTAAGTGTGTGCAGAAGGCCATCCAGCCGTACA    540
 K  R  Y  L  Q  *  C  S  Y  F  K  C  V  Q  K  A  I  Q  P  Y
TGCACAGGATGGTGCCACTTCTGATGTGGCCATTTGATTGGTGCCACTTCTGATGGTGG      600
 M  H  R  M  V  P  L  L  M  V  (            insertion
CCAACATGATTGAACCATTTGGGATGGAAAAGCACCTTTACTCTCAGCCACCTGTTMCT    660
AATGCTGGAGGTCTGTGAGGAACAGAAGTGTGAAGAAAAGGTTTCCCTGGCCACGAT       720
) M  L  E  V  C  E  E  Q  K  C  E  E  K  V  F  P  L  A  T  I
TTACCTGGACTGTTTCTTCGCCAGGATCCCAAGTCCAAGTCCCATCTGCAACTCCTGGG    780
 Y  L  D  C  F  F  A  R  I  P  T  S  K  S  H  L  Q  L  L  G
TGCTGTCTGCATGTTCCTGGCCTCCAGGCTCAAAGAGTCCAGCCACTGACTGCCAAAAA      840
 A  V  C  M  F  L  A  S  R  L  K  E  S  S  P  L  T  A  K  K
              insertion
GCTGTGCATTTATACCGACAACTCCATCAAGCCTCAGGAGCTGCTGGAGTGGGAACTGGT    900
 L  C  I  Y  T  D  N  S  I  K  P  Q  E  L  L  E  W  E  L  V
GGTGTTGGGAAAGTTGAAGTGGAACTTCACGCCTCATGACTTCATTTAGTA            960
 V  L  G  K  L  K  W  N  L  A  A  V  T  P  H  D  F  I  *  Y
```

Fig. 9A

```
CATCTTGCACAAGCTGCCCCAGCAGCGGGAGAAGCTGTCTCCAATCTGCAAGTCA
 I  L  H  K  L  P  Q  Q  R  E  K  L  S  (      deletio                    1080
GAACTTCAATGCTCTGTATGCCCGCCATCAATGGTTGCAACTGGAAGTGTAGG
n)              A  M  Y  P  P  S  M  V  A  T  G  S  V  G                  1140
AGCAGCTATCTGTGGACTTCAGCAACATGAGGAAGTGAGCTCACTCCCTTGCAATGCCCT
 A  A  I  C  G  L  Q  Q  H  E  E  V  S  S  L  P  C  N  A  L              1200
GACTGAGCTGCTGGCAAAGATCACCAACACAGATGTGGATTGTCTCAAAGCCAACCGGG
 T  E  L  L  A  K  I  T  N  T  D  V  D  C  L  K  \  A  N  R              1260
AGCATATATTGAGGTGGTCTTCCTCAACAGCCTGCAGTGCCATCAGGACCAGCAGGACA
 E  H  I  E  V  V  F  L  N  S  L  Q  C  H  Q  D  Q  Q  D                 1320
GATCCAAGTCAGAGGATGAACTGGGCCAAGCAGCAGCACCCCTATAGACCTGTGAGATATCGA
 D  P  S  Q  R  M  N  W  A  K  Q  Q  H  P  Y  R  P  V  R  Y  R            
 (alt: I  Q  V  R  G  *  T  G  P  S  S  T  P  *  D  L  *  D  I  D         
CCTGTGAGGATGGCAGTCCAGCTGAGAGGCGCATTCATAATCTGCTGTCTCCTTCTTTCT            1360
 R  S  K  S  E  D  E  L  G  Q  A\S  T  P  I  D  L  *                     
 L  * (SEQ ID NO. 31)
GGTTATGTTTGTTCTTTGTTCTTTGTATCTTAGGGCGAAACTTAAAAAAAAAACCTCTGCCCCCA      1440

CATAGTTCGTGTGTTTAAAGATCT 1462 (SEQ ID NO. 30)
```

Fig. 9B

```
AAGCTTCCAGATTAGAAAAGAAAAAATAAACTATCTTTATTTGCAGATGACATGATCGG        60
TCCATTCTCATGCTGCTTATAAAGACATACCCAAGACTTCACAATCATGGCGAAAGAGGAAAGAG 120
GTTTGGCTCACAGTTCCCCATGGGTGGAGAGCCTCACAATCATGGCGAAAGAGCAAGGA       180
GCATCTCACATGGCAGGCAGGCAAGAGACTCTCGAGAGAATGAGAGCCAGAGAACAGCGC      240
TAAAATCATCAGATCTCGAGAGACTTATTCGCACTGTGTTCCTCCACAACACATGGGAAACGC   300
CCTTATGATTCAATTATCTCGCACTGTGTGGAGACACAGCCAAACCATATATCAATCTTTTTTCT 360
TACAATTCAAGAGATGAGATTTGGGTGGGAGACACAGCCAAACCATATATCAATCTTTTTTCT   420
TATTCTTTTTTTTTTTTTTTTTGAGATGGAGTCCCACTCTGTTATCTAGGCTGG            480
AGTGCAGTGGTGTGTGAGACTCTTGGCTCACTGCAACCTCCAGCCTCCCAGGTTCAAGCGATTC  540
TCCTGCCTCGAGACTCCTGAATAGCTGAAATTACAGGCACCTGCCACTACGCCTCTCTGCC     600
ATTTTTGTTTGTTTGTTTGTTTGTTTGTTTGTTTGAGACAGAGTCTCGCTCTGTCTCGCC      660
CAGGCTGGAGTGCAGTGGCGCAGTCCCTCAGCTCACTGCAAACTCTGCCTCCCGGGTTCAAG    720
CCATTCTCCTGCCTCAGCTCCCAAGTAGTAGAGATTACAGGCGCCACCACCATGCC         780
AGGCTAATTTTTTGTATTTTTAGTAGAGACAGGGTTTCACCGTGTTAGCCAGGATGGTCT      840
CAATCTCCTGACCTCGTGATCCGCCCACCTCGGCCTCCCAAAGTGCTGGGATTACAGGCG      900
TGAGCCACTATGCCCAACCGTATCAATCTTGTATATAGAAAAAACCTAAGGAATCTAGAAA     960
AAAACCCTATTATAACTAATAATAATCTGCAAAGTTGTAGACTATGAGATCAATA          1020
TACAAAATTAACTCAATTCTTTACATGTACAATAACCCAAAACAATAACAAAACTGGGA      1080
ATATAATTCTATTTTTAATAGTATCACAAAGAATGACAATAATACTTAGAAACAAATGATGGG  1140
                                                   *   W
CGCTAGCTTGCACTCCCGCCCCTGCCTGCCTGCGCTGGAGCTGCTATGCTGCG            1200
 A  L  A  C  T  P  A  L  P  V  R  C  P  S  V  E  L  L  C  C
AAGGCTCGAGGACCCGCAGACGCCAGGGGATCAGCGCGTCCTGCAGAGCTTGCTCCCCTT     1260
 E  G  S  R/D  P  Q  T  P  G  DQ  R  V  L  Q  S  L  L  P  L
GGAGTAGCGCTGCGTGCCTACTTCCAGTGCGTGCAAAGGGAGAGCAAGCCGCA            1320
 E  *  R  C  V  H  C  A  Y  P  Q  C  V  Q  R  E  S  K  P  H
```

Fig. 10A

```
CATGCGGAAGATGCTGGTTTACTGGATGCTGGAGGTGTGTGAGGAGCAGTGCTGTGAGGA    1380
 M  R  K  M  L  V  Y  W  M  L  E  V  C  E  E  Q  C  C  E  E
GGAGCAGTGCTGTAAGGAGGAAGTCTTTCCCCTGGCCATGAACCACCTGCATGCTACCTG    1440
 E  Q  C  C  K  E  E  V  F  P  L  A  M  N  H  L  H  A  T  C
TCCTACGTCCCCACCCCGAAAGGCACAGTTGCAGTCTCTTGGTTGCGGTCTCCATGCG      1500
 P  T  S  P  P  T  R  K  A  Q  L  Q  L  L  V  A  V  S  M  R
GCTGGCCTCCAAGCTGCGTAAGACTGGGCCCATGACCATTGAGAAAATGTGCATCTACAC    1560
 L  A  S  K  L  R  K  T  G  P  M  T  I  E  K  M  C  I  Y  T
CGACCACGCTGTCTCTCCCTGCCAGTTGCGGGACTGGGAGGTGATGGTCCTGGGGAAGCT    1620
 D  H  A  V  S  P  C  Q  L  R  D  W  E  V  M  V  L  G  K  L
CAAATGGGACCTGGCCGCTGTGATTGCTCATGACTTCTTGGCCCTCATTCTGCACCGACC    1680
 K  W  D  L  A  A  V  I  A  H  D  F  L  A  L  I  L  H  R  \
GACAGGCCTTGGTCAAAAAGCATGCCCAGATCTTTTTGGCTGTGTCTGTGCTACAGATTACA 1740
 R  Q  A  L  V  K  K  H  A  Q  I  F  L  A  V  C  A  T  D  Y
CCTTTGCCATGTACCCACCAGTTGTGAAAACAACCCAAATGCCTGTTAACTGATGA       1800
 T  F  A  M  Y  P  P  S  S  C  E  N  N  P  N  A  C  *
(SEQ. ID No. 33)
ACAGATAACCATATGTGATATATATCAATACAATGGAATATGGCCTGGCATGCTGGCTTA   1860
CGCTGTAATCCTGCACTTTGGGAGCCAAAGTGGAGGATCACTTGAGCCGAGGAGTTCAA    1920
GGCCAGCCTGGGCACAAGTGAGACTCCTTCTAAAAATAAAATAAAAAAATARA          1980
AACAATGTAATATTATTCAGCCATAGAAAAGGAATAAAGTACT    2021
(SEQ. ID NO. 32)
```

Fig. 10B

GAGCTCGATCAGTAGTACACTCGTTTGTTTAATTGATAATTGTCCTGAATTATGCCGGCTCCT
GCAGCCCCCTCACGCTCACGAATTCAGCCCAGGCAAATTCTAAAGGTGAAGGACGTC
TACACCCCAACAAAACCAATTAGGAACCTTCGGTGGGTCTTGTCCCAGGCTCTGTCCCAGGGAC
TAATATTCCAGCAATTTAATTTCTTTTTAATTAAAAAAATGAGTCAGAATGGAGATC
ACTGTTTCTCAGCTTTCCATTCAGAGGTGTGTTTCTCCGGTTAAATTGCCGGCACGGGA
AGGGAGGGGTGCAGTTGGGACCCCGCAAGGACCGACTGGTCAAGGTAGGAAGGCAGC
CCGAAGAGAGTCTCCAGGCTAGAAGGACAAGATGAAGGAAATGCTGGCCACCATCTTGGGCT
GCTGCTGGAATTTCGGGCATTTATTTATTTTATTTTTTGAGCGCATGCTAAGCT
GAAATCCCTTTAACTTTTAGGTTACCCCTTGGCATTTGCAACGACGCCCCTGTGCGCCG
GAATGAAACTTGCACAGGGGTTGTGTGCCCGTCCCTTGCATGCTAAATTAG
TTCTTGCAATTTACACGTGTTAATGAAAATGAAAAGATGCAGTCGCTGAGATTCTTTG
GCCGTCTGTCCGCCCGTGGGGTGCCCTCGTGGCGTTCTTGAAATGCGCCCATTCTGCCGG
CTTGGATATGGGGTGTCGCGCGGACGGGACGCGCAGTCACCCTCTCGTGGTCTCCCAGGCTGCG
TGCTGGCCGGCCTTCCTAGTGTGTCCCGACCCACTCGGAGGCCACACCTCCACCTCACCCCCTAAA
TCCCGGGACCACTCGAGGCGGACGGGCATTTCTATGAAAACCGGACTACAGGGGAGAAAGGCT
GCAGCGGGGCGGCGATTGCATTTCTATGAAAACCGGACTACAGGGCAACTGCCCGCAGGGC
AGCGGCGCGGCCTCAGGGATGGCTTTCGCTGCCCCCCTCCCCATTCTCTCCGGCTTCGCCCG
CGCCCCCCTCGCCCCCCTCGCGCCACAGTAACGTCACACAGGGAGTTTTGTTGAAGTTGCA
GATCTTTGCTTAACAACAGTAACGTCGCGCGCGACTAGCAGCGACAGAGTCCGCACG
AAGTCCTGGAGCCTCCAGAGGCGTGTCGGCGAGGGAGCGCGAGCAGAGTCCGCACG
CTCCGGCGAGGGCAGAAGAGCGCGAGGGAGCGCGAGCAGAAGCGAGAGCCGAGCG
CGGACCCCAGCCAGGACCCCACAGCCCCTCCCCAGCTGCCCAGGAAGAGCCCCAGCCATG (SEQ ID No. 34)

Fig. 11

```
GAGCTCGAGCCACGCCATGCCCGCTGCACGTGCCAGCTTGGCCAGCACATCAGGGCGCTG
GTCTCTCCCTTCCTCCTGAGTGAAATACACCAAAGGCGCGGGTGGGGGTGGGGGTGA
CGGGAGGAAGGAGGTGAAGAAACGCCACCAGATCGTATCTCCTGTAAAGACAGCCTTGAC
TCAAGGATGCGTTAGAGCACGTGTCAGGGCCGACCGTGCTGGCGGCGACTTCACCGCAGT
CGGCTCCCAGGGAGAAAGCCTGGCGAGTGAGGCGCGAAACCGGAGGGTCGGCGAGGATG
CGGGCGAAGGACCGAGCGTGAGAGCCGAGCCGGACCTCATGCTCCGGGAAAGGAAGGGGTGGTGTT
TGCGCAGGGGAGCGAGGGGAGCCGGAGCCGGACCTAATCCCTTCACTCGCCCCCTTCCCCG
GGCCATTTCCTAGAAAGCTGCATCGGTTGGCCACGCTCAGCGCAGACACCTCGGGCGGC
TTGTCAGCAGATGCAGGGCGAGGAAGCGGGTTTTCCTGCGTGGCCGCTGGCCGTCGGGGG
AACCGCTGGGAGCCCTGCCCCCGGCCCTGCGGCCCTAGACGCTGCACCGCGTCGCCCC
ACGGCGCCCGAAGAGCCCCCAGAAACACGATGGTTTCTGCTCGAGGATCACATTCTATCC
CTCCAGAGAAGCACCCCCCCCCCTTCCTTCCTAATACCCTCTCCCCTCCCCTTCTTCCTCT
GCACACACTCTGCAGGGGGGCAGAAGGGACGTTGTTCTGGTCCCTTAATCGGGCTT
TCGAAACAGCTTCGAAGTTATCAGGAGAACACAGACTTCAGGGACATGACCTTTATCTCTGG
GTATGCGAGGTTGCTATTTCTGAGTCACCCCATCTTCTAAAATCACCCCCCTTATTTTTCACTTAAGGACCT
ATTTCTAAATTGTCTGAGTCAGGAGATTAGGATCCGTTTTTGAAGAAGCCAAAGTTGGAGGGTCGT
TAAATACAAGGGCAGGAGGATTAGGATCCGTTTTTGAAGAAGCCAAAGTTGGAGGGTCGT
ATTTTGGCGTGCTACACCTACAGAATGAGTGAAATTAGAGGGCAGAAATAGGAGTCGGTA
GTTTTTTGTGGGTTGCCCTGCCCTGTCCGGGCATGCAGGCTTGGATGGAGGAGAGGG
GTTGGGGGTTGCGGGGGACCGCGCGTTTGAAGTTGGGTCGGGCCAGCTGCGTGTTCTCTTAA
TAACGAGAGGGAAAAGGGAGGAGGAGGAGAGATTGAAAGGAGGAGGGAGGACCGGG
AGGGAGGAGAAAGGGAGGAGGAGAACCAGAGCGGGAGCGCGGGAGAGAGCGGAGGAGAGCTAA
CTGCCCAGCCAGCTTCGGTCACGCTTCAGAGCGAGTGCGAGCAGCGCTCTGCTCGCCACCA
CCAGTTTTAAGGGAGGAGCTCCCTTCGCCTCCACCTTCTGCCCCTCCGCCCTCCCCCGAAA
CCCAATCCTCGCCTCGCCTATTTAGCCAAAGGAAGAGGTCAGGAAGCGTCAGGGCCCGGGAAAGCCTCCCCTTCCCCCCTTCCAAAAAA
CAAAAACAGAkAAAACCCTTTTCCAGGCCGGGGAAAGCCGGGGGAAAGCAGGAGGAGGCGCGGGGCTGC
CATG (SEQ ID No. 35)
```

Fig. 12

```
GAGCTCCCGTCCCCATACTACAGGTTCACATCCAGCTTTCAGGACTAGTCAGTCTATGTG
GCCCTCCCTCAATTAATAAATCAGCAACTAATTTGCCAGGTGCGGTGGTTTGTGCCTGTA
ATCCCAGCACTTTAGGAAGCTGAGGCAGGCAGATCACTTGAGGTCAGGAGTTCGAGACCA
GCCTGGCCAACATGGTGAAATCCCGTATCTACTGAAAATACAAAAATTAGCCGGGCATGG
TGGTATGCACCCGTAATCCCAGCTACTCAGGAAGCTGAGGCAGGAGAATCACTTGAAACC
GGGAGGCAGAGGTTGCAGTAAGCTGCACTCCAGCCTGGTGACAAGAGCAAAACTTTGTGT
CAAAAAACAAGAAAACCAAAAAACAAAGGAAAACAGAAAAAACCCTTCTATTTGTTAA
AAAAAAAAAATCCACCGTGAACCAAAAATTAGTAAAACAATGAACTAAAATTTTGTTT
TTGCAAAATGTATGATAACAAAATGTTAAGGAAGGTCATGTGCCGTTATGGTTCACTGCA
GCCTTGAACTCCTGGGCTCAAGCGATCCTCCTGCTTCGGTCTCCCTAGTAGCTGGGACTA
CAGGCTTGTGCCACCGCACCCAGCTTATTTTTTTTTTTATTTTTTGTAGAGATAGGAGT
CTTGCTTTGTTGTCCAGGCTGGTCTTCAACTCCTAGCTTCCAGTGATCCTCCTGCCTCAG
CCTCCCAAGTGCTGGGCCTGATGGACATTTTTATACATAGTGCCATGTACCTATAAATG
AGAAGTTTTAAAAATACTGATTTTAAAAATTAATTTATGTCAAGAATTTTTATACCAAAG
TTAAAAAACCAAACCGAAAATATGAAAAGGGTTAATATCTTTGAGAGGTGATGAGAACTT
ATAAGTCAATAAGAGAAAACAAACATCCCTATAAATGAATAAGCTAAGGACATGAATGGG
TAATGTACATAAGAAATGTAAATGTCTAGTAATATGCCAAAATAGATTTATTATTACTAA
TAAGCCACTTTCACTCTCTAGTTGGCAGAGTTGTTTTGAAAAATAGATATGTAATGATGG
TGGAAAAGATTGGTTTAACTATTCAGCAGGAAAATTTGGCAATTAGAAGTGTATCAAAAG
CCTTAGAATGTTTCATAACCTTAGATTGGGAAATTCCACTTCTAGAAATTAATTCACTTC
TAGAAATAATCATGAGTGTGCACAAAGATATTACCACAAAAATATTTTACAGTATTATGT
CTAATAGAGAAGAACTAGAAATAATTTAAATTTCCACCAATACAGGTTTGCCAAAATACA
TTTTGTACATTCACCTAATGGTATATTATGTCCCTATTACAAATTACGTCCTAGAATATT
TAATAGCATGGAAAAGTGTTAACAGTATTTTTTAATGAAAAAGCTTACAAAACAGTTT
GTGATGATTCCATTTAAAATGTGTGTTTATTCATAGAACAAAGATTAGAAAATAAACAT
TGATATATTAAAGGGTTATTTCATGGCAAATTGCAAATGATTATTTCCTTTTTTTGTGGC
TTATTTGTATTTTTGAAGTTTTCTACAATGTAAAAGAATATTTTATGATATGAAAACTAC
AATACAATTTATAATATAAGAAAGAATAATTCGGCCGGGAACGGTGGCTCACGCCTGTAA
TCCCAGCACTTTTGGAGGCCGAGACCGGCGGATCACGAGGTCAGGGGTTCAAGACTAGCC
TGGCCAACATAGTGAAACCCCATCTCTACGAAAATACAAAAATTAGTCAGGCATGGTGG
TGCGTGCCTGTAGTCCCAGCTACTCGGGAATTGCTTGAACCCGGGAGGTGGAGGTTGCAG
TGAGCCCAGATCGCACCACTGCACTCCAGCTTGAGCAACAGAGTAGACTTCGTCTCAAAA
AAAAAAAAAAAAAAAAAGAATAATTAACAGAAATGGTTAGACACTTCCTTAGTGTCT
CCTAAGTCAGGAGGACCCCAGTAGGGCAGGGATCCTCATGGCCTCCTCCCATTTGGAGCA
TTATTGGAGGTCTTTTTCGGCCTCTTCGTCAAGTGGAATCTAGCTTCCGGTAAAACTACA
AAGTAACCAAAAGTTTGGGAGGTGGAAGAAATGCAACCGGTAGATCTCACAGAGTCTGTG
CAAGAAACTGATTCAATGAGAATCTAGTTTCTCCGTCCACAGTTTCTCCAAACAGAAACT
AAGGCCGACTTTAGGGGCTTGTCCAAACCTAGGCAAGCAACTTAACAAGGTGAGGCCATG
```

Fig. 13A

ACTCCATGGCCTTTCCGTTCTGTTATATGCTGACTTAGACTAAAGCTCTCATACTTTAAA
GTGCACAGAAATCTAGTTAAAATGCAGATTCTGATTCAGGTTAGGGGTGGGCCTGAGAGT
CTGCATTTCTAACCAGCTCCCAGGCGATGACCACGCACGGGACAGGTCTGGGATCACAGT
TTAACTAGCAATGGTGTAGAACACAGAATCTGCAGCAAGAAGGCCAGCTTCCCAATCCTA
GCTCTGCCACGGACCAACTGAATGACAGTTGCCTCGGTTTCCGAGTTTTCGTGAAGATGT
AGTGAGTCATTACATCGTGAGGCTTTCGAGCAGCGTTCACTAAGAACTAGCTCTGACATT
ATTTATCGCATTCCTTACAGCAAGCAGCCGGTGAAGTAGGGTTTGACGAATGAATAAGTG
AATGAATGACCTTTGGAGAAAAATTGTTTCCTGGGTGACTAGAGTCCGAGAAGCAAAATG
GGAGGGCCCGTGGTGGGTAGGAGGCCCACCTCCTAGAAAGTTCTCTGCACCCGGTGGTCC
AGAGGGCCTGGAGTGCCGGAAGCCGGCCGCGTTGCGCTCACGGCCCAATGGGGCCGCGGG
AGGGAGGGGAGAGCGCTCAGCCAACCCTTTCCGTTCCGGGCGCCGCAGCCCCGCCCCTCG
GAGCGTTGCGACGTCCGAGCATTCCACGGTTGCTACATCGTCGCGAGGGGGGGCGCCTGT
CAGGGAAGCGGCGCGCGCGGGCGGCGGGCGGGCTGGGGATCCGCCGCGCAGTGCCAGC
GCCAGCGCCAGACCCGCGCCCCGCGCTCTCCGGCCCGTCGCCTGTCTTGGGACTCGCGAG
CCCGCACTCCCGCCCTGCCTGTTCGCTGCCCGAGT<u>ATG</u> (SEQ ID No. 36)

Fig. 13B

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 1325 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
GCAGTAGCAG CGAGCAGCAG AGTCCGCACG CTCCGGCGAG CGCCAGAACA GCGCGAGGGA      60

GCGCGGGGCA GCAGAAGCGA GAGCCGAGCG CGGACCCAGC CAGGACCCAC AGCCCTCCCC     120

AGCTGCCCAG GAAGAGCCCC AGCCATGGAA CACCAGCTCC TGTGCTGCGA AGTGGAAACC     180

ATCCGCCGCG CGTACCCCGA TGCCAACCTC CTCAACGACC GGGTGCTGCG GGCCATGCTG     240

AAGGCGGAGG AGACCTGCGC GCCCTCGGTG TCCTACTTCA AATGTGTGCA GAACGACGTC     300

CTCCCGTCCA TGCCGAAGAT CGTCGCCACC TGGATGCTGG AGGTCTGCGA GGAACAGAAG     360

TGCGAGGAGG AGCTCTTCCC GCTGGCCATG AACTACCTGG ACCGGTTCCT GTCGCTGGAG     420

CCCGTGAAAA AGAGCCGCCT GCAGCTGCTG GGGGCCACTT GCATGTTCGT GGCCTCTAAG     480

ATGAAGGAGA CCATCCCCCT GACGGCCGAG AAGCTGTGCA TCTACACCGA CGCCTCCATC     540

CCCCCCGAGG ACCTGCTGCA AATGGAGCTG CTCCTGGTGA ACAAGCTCAA GTGGAACCTG     600

GCCGCAATGA CCCCGCACGA TTTCATTGAA CACTTCCTCT CCAAAATGAC AGAGGCGGAG     660

GAGAACAAAC AGATCATCCG CAAACACGCG CAGACCTTCG TTGCCTCTTG TGCCACAGAT     720

CTGAAGTTCA TTTCCAATCC GCCCTCCATG GTGGCAGCGG GGACCGTGGT CGCCGCAGTG     780
```

-continued

```
CAAGGCCTGA ACCTGAGGAG CCCCAACAAC TTCCTGTCGT ACTACCGCCT CACACGCTTC      840

CTCTCCAGAG TGATCAAGTG TGACCCAGAC TGCCTCCGGG CCTCCCAGGA GCAGATCGAA      900

GCCCTGCTGG AGTCAAGCCT GCGCCAGGCC CACCAGAACA TGGACCCCAA GGCCGCCGAG      960

GAGGAGGAAG AGGAGGAGGA GGAGGTGGAC CTGGCTTGCA CACCCACCGA CGTCCCGGAC     1020

CTGGACATCT GAGGGGCCCA GCGAGGCGGG CGCCACCGCC ACCCGCAGCG AGGGCGGAGC     1080

CGGCCCCAGG TGCTCCACAT GACAGTCCCT CCTCTCCGGA GCATTTTGAT ACCAGAAGGG     1140

AAACCTTCAT TCTCCTTGTT GTTGGTTGTT TTTTCCTTTG CTCTTTCCCC CTTCCATCTC     1200

TCACTTAACC AAAACAAAAA GATTACCCAA AAACTGTCTT TAAAAGAGAG AGAGAGAAAA     1260

AAAAAAAAAA AAAAAAAAAA AAAAAAAAAA AAAAAAAAAA AAAAAAAAAA AAAAAAAAAA     1320

AAAAA                                                                 1325
```

(2) INFORMATION FOR SEQ ID NO:2:

(i) SEQUENCE CHARACTERISTICS:
        (A) LENGTH: 295 amino acids
        (B) TYPE: amino acid
        (D) TOPOLOGY: unknown (ii) MOLECULE TYPE: protein (xi) SEQUENCE DESCRIPTION: SEQ ID NO:2:

```
Met Glu His Gln Leu Leu Cys Cys Glu Val Glu Thr Ile Arg Arg Ala
1               5                  10                  15

Tyr Pro Asp Ala Asn Leu Leu Asn Asp Arg Val Leu Arg Ala Met Leu
                20                  25                  30

Lys Ala Glu Glu Thr Cys Ala Pro Ser Val Ser Tyr Phe Lys Cys Val
            35                  40                  45

Gln Lys Glu Val Leu Pro Ser Met Arg Lys Ile Val Ala Thr Trp Met
        50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Gly Ser Ile Arg Pro Glu Glu Leu Leu Gln Met Glu Leu Leu Leu
130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255
```

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
        275                 280                 285

Asp Val Arg Asp Val Asp Ile
    290                 295

(2) INFORMATION FOR SEQ ID NO:3:

(i) SEQUENCE CHARACTERISTICS:
        (A) LENGTH: 1970 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

| | |
|---|---|
| GAATTCCCGC CGGGCTTGGC CATGGAGCTG CTGTGCCACG AGGTGGACCC GGTCCGCAGG | 60 |
| GCCGTGCGGG ACCGCAACCT GCTCGGAGAC GACCGCGTCC TGCAGAACCT GCTCACCATC | 120 |
| GAATTCCCGC CGGGCTTGGC CATGGAGCTG CTGTGCCACG AGGTGGACCC GGTCCGCAGG | 180 |
| GAGGAGCGCT ACCTTCCGCA GTGCTCCTAC TTCAAGTGCG TGCAGAAGGA CATCCAACCC | 240 |
| TACATGCGCA GAATGGTGGC CACCTGGATG CTGGAGGTCT GTGAGGAACA GAAGTGCGAA | 300 |
| GAAGAGGTCT TCCCTCTGGC CATGAATTAC CTGGACCGTT TCTTGGCTGG GGTCCCGACT | 360 |
| CCGAAGTCCC ATCTGCAACT CCTGGGTGCT GTCTGCATGT TCCTGGCCTC CAAACTCAAA | 420 |
| GAGACCAGCC CCCTGACCGC GGAGAAGCTG TGCATTTACA CCGACAACTC CATCAAGCCT | 480 |
| CAGGAGCTGC TGGAGTGGGA ACTGGTGGTG CTGGGGAAGT TGAAGTGGAA CCTGGCAGCT | 540 |
| GTCACTCCTC ATGACTTCAT TGAGCACATC TTGCGCAAGC TGCCCCAGCA GCGGGAGAAG | 600 |
| CTGTCTCTGA TCCGCAAGCA TGCTCAGACC TTCATTGCTC TGTGTGCCAC CGACTTTAAG | 660 |
| TTTGCCATGT ACCCACCGTC GATGATCGCA ACTGGAAGTG TGGGAGCAGC CATCTGTGGG | 720 |
| CTCCAGCAGG ATGAGGAAGT GAGCTCGCTC ACTTGTGATG CCCTGACTGA GCTGCTGGCT | 780 |
| AAGATCACCA ACACAGACGT GGATTGTCTC AAAGCTTGCC AGGACCAGAT TGAGGCGGTG | 840 |
| CTCCTCAATA GCCTGCAGCA GTACCGTCAG GACCAACGTG ACGGATCCAA GTCGGAGGAT | 900 |
| GAACTGGACC AAGCCAGCAC CCCTACAGAC GTGCGGGATA TCGACCTGTG AGGATGCCAG | 960 |
| TTGGGCCGAA AGAGAGAGAC GCGTCCATAA TCTGGTCTCT TCTTCTTTCT GGTTGTTTTT | 1020 |
| TTCTTTGTGT TTTAGGGTGA AACTTAAAAA AAAAATTCTG CCCCCACCTA GATCATATTT | 1080 |
| AAAGATCTTT TAGAAGTGAG AGAAAAAGGT CCTACGAAAA CGGAATAATA AAAAGCATTT | 1140 |
| GGTGCCTATT TGAAGTACAG CATAAGGGAA TCCCTTGTAT ATGCGAACAG TTATTGTTTG | 1200 |
| ATTATGTAAA AGTAATAGTA AAATGCTTAC AGGGAAACCT GCAGAGTAGT TAGAGAATAT | 1260 |
| GTATGCCTGC AATATGGGAC CAAATTAGAG GAGACTTTTT TTTTTCATGT TATGAGCTAG | 1320 |
| CACATACACC CCCTTGTAGT ATAATTTCAA GGAACTGTGT ACGCCATTTA TCGATGATTA | 1380 |
| GATTGCAAAG CAATGAACTC AAGAAGGAAT TGAAATAAGG AGGGACATGA TGGGGAAGGA | 1440 |
| GTACAAAACA ATCTCTCAAC ATGATTGAAC CATTTGGGAT GGAGAAGCAC CTTTGCTCTC | 1500 |
| AGCCACCTGT TACTAAGTCA GGAGTGTAGT TGGATCTCTA CATTAATGTC CTCTTGCTGT | 1560 |
| CTACAGTAGC TGCTACCTAA AAAAAGATGT TTTATTTTGC CAGTTGGACA CAGGTGATTG | 1620 |
| GCTCCTGGGT TTCATGTTCT GTGACATCCT GCTTCTTCTT CCAAATGCAG TTCATTGCAG | 1680 |

```
ACACCACCAT ATTGCTATCT AATGGGGAAA TGTAGCTATG GGCCATAACC AAAACTCACA    1740

TGAAACGGAG GCAGATGGAG ACCAAGGGTG GGATCCAGAA TGGAGTCTTT TCTGTTATTG    1800

TATTTAAAAG GGTAATGTGG CCTTGGCATT TCTTCTTAGA AAAAAACTAA TTTTTGGTGC    1860

TGATTGGCAT GTCTGGTTCA CAGTTTAGCA TTGTTATAAA CCATTCCATT CGAAAAGCAC    1920

TTTGAAAAAT TGTTCCCGAG CGATAGATGG GATGGTTTAT GCAGGAATTC               1970
```

(2) INFORMATION FOR SEQ ID NO:4:

(i) SEQUENCE CHARACTERISTICS:
        (A) LENGTH: 289 amino acids
        (B) TYPE: amino acid
        (D) TOPOLOGY: unknown (ii) MOLECULE TYPE: protein (xi) SEQUENCE DESCRIPTION: SEQ ID NO:4:

```
Met Glu Leu Leu Cys His Glu Val Asp Pro Val Arg Arg Ala Val Arg
1               5                   10                  15

Asp Arg Asn Leu Leu Arg Asp Asp Arg Val Leu Gln Asn Leu Leu Thr
            20                  25                  30

Ile Glu Glu Arg Tyr Leu Pro Gln Cys Ser Tyr Phe Lys Cys Val Gln
        35                  40                  45

Lys Asp Ile Gln Pro Tyr Met Arg Arg Met Val Ala Thr Trp Met Leu
    50                  55                  60

Glu Val Cys Glu Glu Gln Lys Cys Glu Glu Val Phe Pro Leu Ala
65                  70                  75                  80

Met Asn Tyr Leu Asp Arg Phe Leu Ala Gly Val Pro Thr Pro Lys Ser
                85                  90                  95

His Leu Gln Leu Leu Gly Ala Val Cys Met Phe Leu Ala Ser Lys Leu
            100                 105                 110

Lys Glu Thr Ser Pro Leu Thr Ala Glu Lys Leu Cys Ile Tyr Thr Asp
        115                 120                 125

Asn Ser Ile Lys Pro Gln Glu Leu Leu Glu Trp Glu Leu Val Val Leu
    130                 135                 140

Gly Lys Leu Lys Trp Asn Leu Ala Ala Val Thr Pro His Asp Phe Ile
145                 150                 155                 160

Glu His Ile Leu Arg Lys Leu Pro Gln Gln Arg Glu Lys Leu Ser Leu
                165                 170                 175

Ile Arg Lys His Ala Gln Thr Phe Ile Ala Leu Cys Ala Thr Asp Phe
            180                 185                 190

Lys Phe Ala Met Tyr Pro Pro Ser Met Ile Ala Thr Gly Ser Val Gly
        195                 200                 205

Ala Ala Ile Cys Gly Leu Gln Gln Asp Glu Glu Val Ser Ser Leu Thr
    210                 215                 220

Cys Asp Ala Leu Thr Glu Leu Leu Ala Lys Ile Thr Asn Thr Asp Val
225                 230                 235                 240

Asp Cys Leu Lys Ala Cys Gln Glu Gln Ile Glu Ala Val Leu Leu Asn
                245                 250                 255

Ser Leu Gln Gln Tyr Arg Gln Asp Gln Arg Asp Gly Ser Lys Ser Glu
            260                 265                 270

Asp Glu Leu Asp Gln Ala Ser Thr Pro Thr Asp Val Arg Asp Ile Asp
        275                 280                 285

Leu
```

(2) INFORMATION FOR SEQ ID NO:5:

(i) SEQUENCE CHARACTERISTICS:
        (A) LENGTH: 1926 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

```
GAATTCCGAT CCCCAGCCCG CCCGCCCGCG CTCTCCGGCC CGTCGCCTGC CTTGGGACTC    60
GCGAGCCCGC ACTCCCGCCC TGCCTGTTCG CTGCCCGAGT ATGGAGCTGC TGTGTTGCGA   120
AGGCACCCGG CACGCGCCCC GGGCCGGGCC GGACCCGCGG CTGCTGGGGG ACCAGCGTGT   180
CCTGCAGAGC CTGCTCCGCC TGGAGGAGCG CTACGTACCC CGCGCCTCCT ACTTCCAGTG   240
CGTGCAGCGG GAGATCAAGC CGCACATGCG GAAGATGCTG GCTTACTGGA TGCTGGAGGT   300
ATGTGAGGAG CAGCGCTGTG AGGAGGAAGT CTTCCCCCTG GCCATGAACT ACCTGGATCG   360
CTACCTGTCT TGCGTCCCCA CCCGAAAGGC GCAGTTGCAG CTCCTGGGTG CGGTCTGCAT   420
GGCCCCTGAC CATCGAAAAA CTGTGCATCT ACACCGACCA CGCTGTCGCC AGTTGCGGGA   480
CTGGGAGGTG CTGGTCCTAG GGAAGCTCAA GTGGGACCTG GCTGCTGTGA TTGCACATGA   540
TTTCCTGGCC TTCATTCTGC ACCGGCTCTC TCTGCCCCGT GACCGACAGG CCTTGGTCAA   600
AAAGCATGCC CAGACCTTTT TGGCCCTCTG TGCTACAGAT TATACCTTTG CCATGTACCC   660
GCCATCCATG ATCGCCACGG GCAGCATTGG GGCTGCAGTG CAAGGCCTGG GTGCCTGCTC   720
CATGTCCGGG GATGAGCTCA CAGAGCTGCT GGCAGGGATC ACTGGCACTG AAGTGGACTG   780
CCTGCGGGCC TGTCAGGAGC AGATCGAAGC TGCACTCAGG GAGAGCCTCA GGGAAGCCGC   840
TCAGACCAGC TCCAGCCCAG CGCCCAAAGC CCCCGGGGC TCCAGCAGCC AAGGGCCCAG    900
CCAGACCAGC ACTCTTACAG ATGTCACAGC CATACACCTG TAGCCCTGGA GAGGCCCTCT   960
GGAGTGGCCA CTAAGCAGAG GAGGGGCCGC TGCACCCACC TCCCTGCCTC CAGGAACCAC  1020
ACCACATCTA AGCCTGAAGG GGCGTCTGTT CCCCCTTCAC AAAGCCCAAG GGATCTGGTC  1080
CTACCCATCC CCGCAGTGTG CACTAAGGGG CCCGGCCAGC CATGTCTGCA TTTCGGTGGC  1140
TAGTCAAGCT CCTCCTCCCT GCATCTGACC AGCAGCGCCT TTCCCAACTC TAGCTGGGGG  1200
TGGGCCAGGC TGATGGGACA GAATTGGATA CATACACCAG CATTCCTTTT GAACGCCCCC  1260
CCCCACCCCT GGGGGCTCTC ATGTTTTCAA CTGCCAAAAT GCTCTAGTGC CTTCTAAAGG  1320
TGTTGTCCCT TCTAGGGTTA TTGCATTTGG ATTGGGGTCC CTCTAAAATT TAATGCATGA  1380
TAGACACATA TGAGGGGAA TAGTCTAGAT GGCTCCTCTC AGTACTTTGG AGGCCCCTAT   1440
GTAGTCCTGG CTGACAGCTG CTCCTAGAGG GAGGGGCCTA GGCTCAGCCA GAGAAGCTAT  1500
AAATTCCTCT TTGCTTTGCT TTCTGCTCAG CTTCTCCTGT GTGATTGACA GCTTTGCTGC  1560
TGAAGGCTCA TTTTAATTTA TTAATTGCTT TGAGCACAAC TTTAAGAGGA CGTAATGGGG  1620
TCCTGGCCAT CCCACAAGTG GTGGTAACCC TGGTGGTTGC TGTTTTCCTC CCTTCTGCTA  1680
CTGGCAAAAG GATCTTTGTG GCCAAGGAGC TGCTATAGCC TGGGGTGGGG TCATGCCCTC  1740
CTCTCCCATT GTCCCTCTGC CCCATCCTCC AGCAGGGAAA ATGCAGCAGG GATGCCCTGG  1800
AGGTGCTGAG CCCCTGTCTA GAGAGGGAGG CAAGCCTGTT GACACAGGTC TTTCCTAAGG  1860
CTGCAAGGTT TAGGCTGGTG GCCCAGGACC ATCATCCTAC TGTAATAAAG ATGATTGTGG  1920
GAATTC                                                             1926
```

(2) INFORMATION FOR SEQ ID NO:6:

(i) SEQUENCE CHARACTERISTICS:
        (A) LENGTH: 291 amino acids
        (B) TYPE: amino acid
        (D) TOPOLOGY: unknown (ii) MOLECULE TYPE: protein (xi) SEQUENCE DESCRIPTION: SEQ ID NO:6:

```
Met Glu Leu Leu Cys Cys Glu Gly Thr Arg His Ala Pro Arg Ala Gly
1               5                   10                  15

Pro Asp Pro Arg Leu Leu Gly Asp Gln Arg Val Leu Gln Ser Leu Leu
            20                  25                  30

Arg Leu Glu Glu Arg Tyr Val Pro Arg Ala Ser Tyr Pro Gln Cys Val
        35                  40                  45

Gln Arg Glu Ile Lys Pro His Met Arg Lys Met Leu Ala Tyr Trp Met
50                  55                  60

Leu Glu Val Cys Glu Glu Gln Arg Cys Glu Glu Val Phe Pro Leu
65                  70                  75                  80

Ala Met Asn Tyr Leu Asp Arg Tyr Leu Ser Cys Val Pro Thr Arg Lys
                85                  90                  95

Ala Gln Leu Gln Leu Leu Gly Ala Val Cys Met Leu Leu Ala Ser Lys
            100                 105                 110

Leu Arg Glu Thr Thr Pro Leu Thr Ile Glu Lys Leu Cys Ile Tyr Thr
        115                 120                 125

Asp Ala Val Ser Pro Arg Gln Leu Arg Asp Trp Glu Val Leu Val Leu
130                 135                 140

Gly Lys Leu Lys Trp Asp Leu Ala Ala Val Ile Ala His Asp Phe Leu
145                 150                 155                 160

Ala Phe Ile Leu His Arg Leu Ser Leu Pro Arg Asp Arg Gln Ala Leu
                165                 170                 175

Val Lys Lys His Ala Gln Thr Phe Leu Ala Leu Cys Ala Thr Asp Tyr
            180                 185                 190

Thr Phe Ala Met Tyr Pro Pro Ser Met Ile Ala Thr Gly Ser Ile Gly
        195                 200                 205

Ala Ala Val Gln Gly Leu Gly Ala Cys Ser Met Ser Gly Asp Glu Leu
210                 215                 220

Thr Glu Leu Leu Ala Gly Ile Thr Gly Thr Glu Val Asp Cys Leu Arg
225                 230                 235                 240

Ala Cys Gln Glu Gln Ile Glu Ala Ala Leu Arg Glu Ser Leu Arg Glu
                245                 250                 255

Ala Ala Gln Thr Ser Ser Ser Pro Ala Pro Lys Ala Pro Arg Gly Ser
            260                 265                 270

Ser Ser Gln Gly Pro Ser Gln Thr Ser Thr Pro Thr Asp Val Thr Ala
        275                 280                 285

Ile His Leu
290
```

(2) INFORMATION FOR SEQ ID NO:7:

(i) SEQUENCE CHARACTERISTICS:
        (A) LENGTH: 819 amino acids
        (B) TYPE: amino acid
        (D) TOPOLOGY: unknown (ii) MOLECULE TYPE: protein (xi) SEQUENCE DESCRIPTION: SEQ ID NO:7:

```
Gln Leu Cys Cys Glu Val Glu Thr Ile Arg Arg Ala Tyr Pro Asp Ala
1               5                   10                  15

Asn Leu Leu Asn Asp Arg Val Leu Arg Ala Met Leu Lys Ala Glu Glu
            20                  25                  30

Thr Cys Ala Pro Ser Val Ser Tyr Phe Lys Cys Val Gln Lys Glu Val
        35                  40                  45

Leu Pro Ser Met Arg Lys Ile Val Ala Thr Trp Met Leu Glu Val Cys
    50                  55                  60

Glu Glu Gln Lys Cys Glu Glu Val Phe Pro Leu Ala Met Asn Tyr
65                  70                  75                  80

Leu Asp Arg Phe Leu Ser Leu Glu Pro Val Lys Lys Ser Arg Leu Gln
                85                  90                  95

Leu Leu Gly Ala Thr Cys Met Phe Ser Ile Val Leu Glu Asp Glu Lys
            100                 105                 110

Pro Val Ser Val Asn Glu Val Pro Asp Tyr His Glu Asp Ile His Thr
        115                 120                 125

Tyr Leu Arg Glu Met Glu Val Lys Cys Lys Pro Lys Val Gly Tyr Met
    130                 135                 140

Lys Lys Gln Pro Asp Ile Thr Asn Ser Met Arg Ala Ile Leu Val Asp
145                 150                 155                 160

Trp Leu Val Glu Val Gly Glu Glu Tyr Lys Leu Gln Asn Glu Thr Leu
                165                 170                 175

His Leu Ala Val Asn Tyr Ile Asp Arg Phe Leu Ser Ser Met Ser Val
            180                 185                 190

Leu Arg Gly Lys Leu Gln Leu Val Gly Thr Ala Ala Met Leu Lys Glu
        195                 200                 205

Leu Pro Pro Arg Asn Asp Arg Gln Arg Phe Leu Glu Val Val Gln Tyr
    210                 215                 220

Gln Met Asp Ile Leu Glu Tyr Phe Arg Glu Ser Glu Lys Lys His Arg
225                 230                 235                 240

Pro Lys Pro Arg Tyr Met Arg Arg Gln Lys Asp Ile Ser His Asn Met
                245                 250                 255

Arg Ser Ile Leu Ile Asp Trp Leu Val Glu Val Ser Glu Glu Tyr Lys
            260                 265                 270

Leu Asp Thr Glu Thr Leu Tyr Leu Ser Val Phe Tyr Leu Asp Arg Phe
        275                 280                 285

Leu Ser Gln Met Ala Val Arg Ser Lys Leu Gln Leu Val Gly Thr
    290                 295                 300

Ala Ala Met Tyr Val Asn Asp Val Asp Ala Glu Asp Gly Ala Asp Pro
305                 310                 315                 320

Asn Leu Cys Ser Glu Tyr Val Lys Asp Ile Tyr Ala Tyr Leu Arg Gln
                325                 330                 335

Leu Glu Glu Glu Gln Ala Val Arg Pro Lys Tyr Leu Leu Gly Arg Glu
            340                 345                 350

Val Thr Gly Asn Met Arg Ala Ile Leu Ile Asp Trp Leu Val Gln Val
        355                 360                 365

Gln Met Lys Phe Arg Leu Leu Gln Glu Thr Met Tyr Met Thr Val Ser
    370                 375                 380

Ile Ile Asp Arg Phe Met Gln Asn Asn Cys Val Pro Lys Lys Met Leu
385                 390                 395                 400

Gln Leu Val Gly Val Thr Ala Met Phe Trp Asp Asp Leu Asp Ala Glu
                405                 410                 415
```

```
Asp Trp Ala Asp Pro Leu Met Val Ser Glu Tyr Val Val Asp Ile Phe
        420                 425                 430

Glu Tyr Leu Asn Glu Leu Glu Ile Glu Thr Met Pro Ser Pro Thr Tyr
            435                 440                 445

Met Asp Arg Gln Lys Glu Leu Ala Trp Lys Met Arg Gly Ile Leu Thr
        450                 455                 460

Asp Trp Leu Ile Glu Val His Ser Arg Phe Arg Leu Leu Pro Glu Thr
465                 470                 475                 480

Leu Phe Leu Ala Val Asn Ile Ile Asp Arg Phe Leu Ser Leu Arg Val
                485                 490                 495

Cys Ser Leu Asn Lys Leu Gln Leu Val Gly Ile Ala Ala Leu Phe Ile
            500                 505                 510

Glu Leu Ser Asn Ala Glu Leu Leu Thr His Tyr Glu Thr Ile Gln Glu
        515                 520                 525

Tyr His Glu Glu Ile Ser Gln Asn Val Leu Val Gln Ser Ser Lys Thr
        530                 535                 540

Lys Pro Asp Ile Lys Leu Ile Asp Gln Gln Pro Glu Met Asn Pro His
545                 550                 555                 560

Gln Thr Arg Glu Ala Ile Val Thr Phe Leu Tyr Gln Leu Ser Val Met
            565                 570                 575

Thr Arg Val Ser Asn Gly Ile Phe Phe His Ser Val Arg Phe Tyr Asp
            580                 585                 590

Arg Tyr Cys Ser Lys Arg Val Val Leu Lys Asp Gln Ala Lys Leu Val
        595                 600                 605

Val Gly Thr Cys Leu Trp Pro Asn Leu Val Lys Arg Glu Leu Gln Ala
        610                 615                 620

His His Ser Ala Ile Ser Glu Tyr Asn Asn Asp Gln Leu Asp His Tyr
625                 630                 635                 640

Phe Arg Leu Ser His Thr Glu Arg Pro Leu Tyr Asn Leu Asn Ser Gln
                645                 650                 655

Pro Gln Val Asn Pro Lys Met Arg Phe Leu Ile Phe Asp Phe Ile Met
            660                 665                 670

Tyr Cys His Thr Arg Leu Asn Leu Ser Thr Ser Thr Leu Phe Leu Thr
        675                 680                 685

Phe Thr Ile Leu Asp Lys Tyr Ser Ser Arg Phe Ile Ile Lys Ser Tyr
        690                 695                 700

Asn Tyr Gln Leu Leu Ser Leu Thr Ala Leu Trp Val Ala Ser Lys Met
705                 710                 715                 720

Lys Glu Thr Ile Pro Leu Thr Ala Glu Lys Leu Cys Ile Tyr Thr Asp
                725                 730                 735

Gly Ser Ile Arg Pro Glu Glu Leu Leu Gln Met Glu Leu Leu Leu Val
            740                 745                 750

Asn Lys Leu Lys Trp Asn Leu Ala Ala Met Thr Pro His Glu Phe Ile
            755                 760                 765

Glu His Phe Leu Ser Lys Met Pro Glu Ala Glu Glu Asn Lys Gln Ile
        770                 775                 780

Ile Arg Lys His Ala Gln Thr Phe Val Ala Leu Cys Ala Thr Asp Val
785                 790                 795                 800

Lys Phe Ile Ser Asn Pro Pro Ser Met Val Ala Ala Gly Ser Val Val
                805                 810                 815

Ala Ala Val (2) INFORMATION FOR SEQ ID NO:8:
```

(i) SEQUENCE CHARACTERISTICS:
    (A) LENGTH: 100 amino acids
    (B) TYPE: amino acid
    (D) TOPOLOGY: unknown (ii) MOLECULE TYPE: protein (xi) SEQUENCE DESCRIPTION: SEQ ID NO:8:

```
Leu Ala Ser Lys Phe Glu Glu Ile Tyr Pro Pro Glu Val Ala Glu Phe
1               5                   10                  15

Val Tyr Ile Thr Val Asp Thr Tyr Thr Lys Lys Gln Val Leu Arg Met
            20                  25                  30

Glu His Leu Val Leu Lys Val Leu Thr Phe Asp Leu Ala Ala Pro Thr
            35                  40                  45

Val Asn Gln Phe Leu Thr Gln Tyr Phe Leu His Gln Gln Asn Cys Lys
50                      55                  60

Val Glu Ser Leu Ala Met Phe Leu Gly Glu Leu Ser Leu Ile Asp Ala
65                      70                  75                  80

Asp Pro Tyr Leu Lys Tyr Leu Pro Ser Val Ile Ala Gly Ala Ala Phe
                85                  90                  95

His Leu Ala Leu
            100
```

(2) INFORMATION FOR SEQ ID NO:9:

(i) SEQUENCE CHARACTERISTICS:
    (A) LENGTH: 101 amino acids
    (B) TYPE: amino acid
    (D) TOPOLOGY: unknown (ii) MOLECULE TYPE: protein (xi) SEQUENCE DESCRIPTION: SEQ ID NO:9:

```
Ile Ala Ala Lys Tyr Glu Glu Ile Tyr Pro Pro Glu Val Gly Glu Phe
1               5                   10                  15

Val Phe Leu Thr Asp Asp Ser Tyr Thr Lys Ala Gln Val Leu Arg Met
            20                  25                  30

Glu Gln Val Ile Leu Lys Ile Leu Ser Phe Asp Leu Cys Thr Pro Thr
            35                  40                  45

Ala Tyr Val Phe Ile Asn Thr Tyr Ala Val Leu Cys Asp Met Pro Glu
50                      55                  60

Lys Leu Lys Tyr Met Thr Leu Tyr Ile Ser Glu Leu Ser Leu Met Glu
65                      70                  75                  80

Gly Glu Thr Tyr Leu Gln Tyr Leu Pro Ser Leu Met Ser Ser Ala Ser
                85                  90                  95

Val Ala Leu Ala Arg
            100
```

(2) INFORMATION FOR SEQ ID NO:10:

(i) SEQUENCE CHARACTERISTICS:
    (A) LENGTH: 100 amino acids
    (B) TYPE: amino acid
    (D) TOPOLOGY: unknown (ii) MOLECULE TYPE: protein (xi) SEQUENCE DESCRIPTION: SEQ ID NO:10:

```
Ile Ala Ser Lys Tyr Glu Glu Met Tyr Pro Pro Glu Ile Gly Asp Phe
1               5                   10                  15
```

-continued

```
Ala Phe Val Thr Asp Asn Thr Tyr Thr Lys His Gln Ile Arg Gln Met
                 20                  25                  30

Glu Met Lys Ile Leu Arg Ala Leu Asn Phe Gly Leu Gly Arg Pro Leu
         35                  40                  45

Pro Leu His Phe Leu Arg Arg Ala Ser Lys Ile Gly Glu Val Asp Val
 50                  55                  60

Glu Gln His Thr Leu Ala Lys Tyr Leu Met Glu Leu Thr Met Leu Asp
 65                  70                  75                  80

Tyr Asp Met Val His Phe Pro Pro Ser Gln Ile Ala Ala Gly Ala Phe
                 85                  90                  95

Cys Leu Ala Leu
            100
```

(2) INFORMATION FOR SEQ ID NO:11:

(i) SEQUENCE CHARACTERISTICS:
        (A) LENGTH: 100 amino acids
        (B) TYPE: amino acid
        (D) TOPOLOGY: unknown (ii) MOLECULE TYPE: protein (xi) SEQUENCE DESCRIPTION: SEQ ID NO:11:

```
Ile Ala Ser Lys Tyr Glu Glu Val Met Cys Pro Ser Val Gln Asn Phe
 1               5                  10                  15

Val Tyr Met Ala Asp Gly Gly Tyr Asp Glu Glu Ile Leu Gln Ala
                 20                  25                  30

Glu Arg Tyr Ile Leu Arg Val Leu Glu Phe Asn Leu Ala Tyr Pro Asn
         35                  40                  45

Pro Met Asn Phe Leu Arg Arg Ile Ser Lys Ala Asp Phe Tyr Asp Ile
 50                  55                  60

Gln Thr Arg Thr Val Ala Lys Tyr Leu Val Glu Ile Gly Leu Leu Asp
 65                  70                  75                  80

His Lys Leu Leu Pro Tyr Pro Pro Ser Gln Gln Cys Ala Ala Ala Met
                 85                  90                  95

Tyr Leu Ala Arg
            100
```

(2) INFORMATION FOR SEQ ID NO:12:

(i) SEQUENCE CHARACTERISTICS:
        (A) LENGTH: 51 amino acids
        (B) TYPE: amino acid
        (D) TOPOLOGY: unknown (ii) MOLECULE TYPE: protein (xi) SEQUENCE DESCRIPTION: SEQ ID NO:12:

```
Leu Ala Ala Lys Thr Trp Gly Arg Leu Ser Glu Leu Val His Tyr Cys
 1               5                  10                  15

Gly Gly Ser Asp Leu Phe Asp Glu Ser Met Phe Ile Gln Met Glu Arg
                 20                  25                  30

His Ile Leu Asp Thr Leu Asn Trp Asp Val Tyr Glu Pro Met Ile Asn
         35                  40                  45

Asp Tyr Ile
 50
```

(2) INFORMATION FOR SEQ ID NO:13:

(i) SEQUENCE CHARACTERISTICS:

(A) LENGTH: 51 amino acids
        (B) TYPE: amino acid
        (D) TOPOLOGY: unknown (ii) MOLECULE TYPE: protein (xi) SEQUENCE DESCRIPTION: SEQ ID NO:13:

Ile Ser Ser Lys Phe Trp Asp Arg Met Ala Thr Leu Lys Val Leu Gln
1               5                  10                  15

Asn Leu Cys Cys Asn Gln Tyr Ser Ile Lys Gln Phe Thr Thr Met Glu
            20                  25                  30

Met His Leu Phe Lys Ser Leu Asp Trp Ser Ile Ser Ala Thr Phe Asp
        35                  40                  45

Ser Tyr Ile
    50

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

CCCAAAAACT GTCTTT                                                          16

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

CCCAAAAACT GTCTTTAAAA GAGAGAGAGA G                                         31

(2) INFORMATION FOR SEQ ID NO:16:

(i) SEQUENCE CHARACTERISTICS:
        (A) LENGTH: 175 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

CCCAAAAACT GTCTTTAAAA GAGAGAGAGA GAAAAAAAAA ATAGTATTCC CAAAAACTGT          60

CTTTAAAAGA GAGAGAGAGA AAAAAAAATA GTATTCCCAA AAACTGTCTT TAAAAGAGAG         120

AGAGAGAAAA AAAAAATAGT ATTTGCATAA CCCTGAGCGG TGGGGGAGGA GGGTT             175

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

TGCATAACCC TGAGCGGTGG GGGAGGAGGG TT                32

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

TGCATAACCC TGAGCGGTGG GGGAGGAGGG TT                32

(2) INFORMATION FOR SEQ ID NO:19:

(i) SEQUENCE CHARACTERISTICS:
        (A) LENGTH: 295 amino acids
        (B) TYPE: amino acid
        (D) TOPOLOGY: unknown (ii) MOLECULE TYPE: protein (xi) SEQUENCE DESCRIPTION: SEQ ID NO:19:

```
Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Gly Ser Ile Arg Pro Glu Glu Leu Leu Gln Met Glu Leu Leu Leu
130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Lys Gly Leu Asn Leu Arg Ser Pro Asn Asn Phe Leu
210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255
```

```
Ser Ser Leu Arg Gln Ala Gln Gln Asn Met Asp Pro Lys Ala Ala Glu
        260                 265                 270

Glu Glu Glu Glu Glu Glu Glu Val Asp Leu Ala Cys Thr Pro Thr
    275                 280                 285

Asp Val Arg Asp Val Asp Ile
    290                 295

(2) INFORMATION FOR SEQ ID NO:20:

(i) SEQUENCE CHARACTERISTICS:
        (A) LENGTH: 295 amino acids
        (B) TYPE: amino acid
        (D) TOPOLOGY: unknown (ii) MOLECULE TYPE: protein (xi) SEQUENCE DESCRIPTION: SEQ ID NO:20:

Met Glu Asn Gln Leu Leu Cys Cys Glu Val Glu Thr Ile Arg Arg Ala
1               5                   10                  15

Tyr Pro Asp Thr Asn Leu Leu Asn Asp Arg Val Leu Arg Ala Met Leu
                20                  25                  30

Lys Thr Glu Glu Thr Cys Ala Pro Ser Val Ser Tyr Phe Lys Cys Val
            35                  40                  45

Gln Lys Glu Ile Val Pro Ser Met Arg Lys Ile Val Ala Thr Trp Met
        50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Leu Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Asp Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Met
        195                 200                 205

Val Ala Ala Met Gln Gly Leu Asn Leu Gly Ser Pro Asn Asn Phe Leu
    210                 215                 220

Ser Arg Tyr Arg Thr Thr His Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Thr Glu
            260                 265                 270

Glu Glu Gly Glu Val Glu Glu Glu Ala Gly Leu Ala Cys Thr Pro Thr
        275                 280                 285

Asp Val Arg Asp Val Asp Ile
    290                 295
```

(2) INFORMATION FOR SEQ ID NO:21:

(i) SEQUENCE CHARACTERISTICS:
        (A) LENGTH: 189 amino acids
        (B) TYPE: amino acid
        (D) TOPOLOGY: unknown (ii) MOLECULE TYPE: protein (xi) SEQUENCE DESCRIPTION: SEQ ID NO:21:

```
Met Glu Leu Leu Cys His Glu Val Asp Pro Val Arg Arg Ala Val Arg
1               5                   10                  15

Asp Arg Asn Leu Leu Arg Asp Asp Arg Val Leu Gln Asn Leu Leu Thr
            20                  25                  30

Ile Glu Glu Arg Tyr Leu Pro Gln Cys Ser Tyr Phe Lys Cys Val Gln
        35                  40                  45

Lys Asp Ile Gln Pro Tyr Met Arg Arg Met Val Ala Thr Trp Met Leu
    50                  55                  60

Glu Val Cys Glu Glu Gln Lys Cys Glu Glu Val Phe Pro Leu Ala
65                  70                  75                  80

Met Asn Tyr Leu Asp Arg Phe Leu Ala Gly Val Pro Thr Pro Lys Ser
                85                  90                  95

His Pro Pro Ser Met Ile Ala Thr Gly Ser Val Gly Ala Ala Ile Cys
            100                 105                 110

Gly Leu Lys Gln Asp Glu Glu Val Ser Ser Leu Thr Cys Asp Ala Leu
        115                 120                 125

Thr Glu Leu Leu Ala Lys Ile Thr Asn Thr Asp Val Asp Cys Leu Lys
    130                 135                 140

Ala Cys Gln Glu Gln Ile Glu Ala Val Leu Leu Asn Ser Leu Gln Gln
145                 150                 155                 160

Tyr Arg Gln Asp Gln Arg Asp Gly Ser Lys Ser Glu Asp Glu Leu Asp
                165                 170                 175

Gln Ala Ser Thr Pro Thr Asp Val Arg Asp Ile Asp Leu
            180                 185
```

(2) INFORMATION FOR SEQ ID NO:22:

(i) SEQUENCE CHARACTERISTICS:
        (A) LENGTH: 236 amino acids
        (B) TYPE: amino acid
        (D) TOPOLOGY: unknown (ii) MOLECULE TYPE: protein (xi) SEQUENCE DESCRIPTION: SEQ ID NO:22:

```
Met Arg Arg Met Val Ala Thr Trp Met Leu Glu Val Cys Glu Glu Gln
1               5                   10                  15

Lys Cys Glu Glu Glu Val Phe Pro Leu Ala Met Asn Tyr Leu Asp Arg
            20                  25                  30

Phe Leu Ala Gly Val Pro Thr Pro Lys Thr His Leu Gln Leu Leu Gly
        35                  40                  45

Ala Val Cys Met Phe Leu Ala Ser Lys Leu Lys Glu Thr Ile Pro Leu
    50                  55                  60

Thr Ala Glu Lys Leu Cys Ile Tyr Thr Asp Asn Ser Val Lys Pro Gln
65                  70                  75                  80

Glu Leu Leu Glu Trp Glu Leu Val Val Leu Gly Lys Leu Lys Trp Asn
                85                  90                  95

Leu Ala Ala Val Thr Pro His Asp Phe Ile Glu His Ile Leu Arg Lys
```

-continued

```
                100                 105                 110
Leu Pro Gln Gln Lys Glu Lys Leu Ser Leu Ile Arg Lys His Ala Gln
            115                 120                 125
Thr Phe Ile Ala Leu Cys Ala Thr Asp Phe Lys Phe Ala Met Tyr Pro
        130                 135                 140
Pro Ser Met Ile Ala Thr Gly Ser Val Gly Ala Ala Ile Cys Gly Leu
145                 150                 155                 160
Gln Gln Asp Asp Glu Val Asn Thr Leu Thr Cys Asp Ala Leu Thr Glu
                165                 170                 175
Leu Leu Ala Lys Ile Thr His Thr Asp Val Asp Cys Leu Lys Ala Cys
            180                 185                 190
Gln Glu Gln Ile Glu Ala Leu Leu Leu Asn Ser Leu Gln Gln Phe Arg
        195                 200                 205
Gln Glu Gln His Asn Ala Gly Ser Lys Ser Val Glu Asp Pro Asp Gln
    210                 215                 220
Ala Thr Thr Pro Thr Asp Val Arg Asp Val Asp Leu
225                 230                 235
```

(2) INFORMATION FOR SEQ ID NO:23:

(i) SEQUENCE CHARACTERISTICS:
        (A) LENGTH: 292 amino acids
        (B) TYPE: amino acid
        (D) TOPOLOGY: unknown (ii) MOLECULE TYPE: protein (xi) SEQUENCE DESCRIPTION: SEQ ID NO:23:

```
Met Glu Leu Leu Cys Cys Glu Gly Thr Arg His Ala Pro Arg Ala Gly
1               5                   10                  15
Pro Asp Pro Arg Leu Leu Gly Asp Gln Arg Val Leu Gln Ser Leu Leu
            20                  25                  30
Arg Leu Glu Glu Arg Tyr Val Pro Arg Ala Ser Tyr Phe Gln Cys Val
        35                  40                  45
Gln Arg Glu Ile Lys Pro His Met Arg Lys Met Leu Ala Tyr Trp Met
    50                  55                  60
Leu Glu Val Cys Glu Glu Gln Arg Cys Glu Glu Glu Val Phe Pro Leu
65                  70                  75                  80
Ala Met Asn Tyr Leu Asp Arg Tyr Leu Ser Cys Val Pro Thr Arg Lys
                85                  90                  95
Ala Gln Leu Gln Leu Leu Gly Ala Val Cys Met Leu Leu Ala Ser Lys
            100                 105                 110
Leu Arg Glu Thr Thr Pro Leu Thr Ile Glu Lys Leu Cys Ile Tyr Thr
        115                 120                 125
Asp His Ala Val Ser Pro Arg Gln Leu Arg Asp Trp Glu Val Leu Val
    130                 135                 140
Leu Gly Lys Leu Lys Trp Asp Leu Ala Ala Val Ile Ala His Asp Phe
145                 150                 155                 160
Leu Ala Phe Ile Leu His Arg Leu Ser Leu Pro Arg Asp Arg Gln Ala
                165                 170                 175
Leu Val Lys Lys His Ala Gln Thr Phe Leu Ala Leu Cys Ala Thr Asp
            180                 185                 190
Tyr Thr Phe Ala Met Tyr Pro Pro Ser Met Ile Ala Thr Gly Ser Ile
        195                 200                 205
Gly Ala Ala Val Gln Gly Leu Gly Ala Cys Ser Met Ser Gly Asp Glu
    210                 215                 220
```

```
Leu Thr Glu Leu Leu Ala Gly Ile Thr Gly Thr Glu Val Asp Cys Leu
225                 230                 235                 240

Arg Ala Cys Gln Glu Gln Ile Glu Ala Ala Leu Arg Glu Ser Leu Arg
                245                 250                 255

Glu Ala Ala Gln Thr Ser Ser Ser Pro Ala Pro Lys Ala Pro Arg Gly
                260                 265                 270

Ser Ser Ser Gln Gly Pro Ser Gln Thr Ser Thr Pro Thr Asp Val Thr
            275                 280                 285

Ala Ile His Leu
        290
```

(2) INFORMATION FOR SEQ ID NO:24:

(i) SEQUENCE CHARACTERISTICS:
        (A) LENGTH: 237 amino acids
        (B) TYPE: amino acid
        (D) TOPOLOGY: unknown (ii) MOLECULE TYPE: protein (xi) SEQUENCE DESCRIPTION: SEQ ID NO:24:

```
Met Arg Lys Met Leu Ala Tyr Trp Met Leu Glu Val Cys Glu Glu Gln
1               5                   10                  15

Arg Cys Glu Glu Asp Val Phe Pro Leu Ala Met Asn Tyr Leu Asp Arg
                20                  25                  30

Tyr Leu Ser Cys Val Pro Thr Arg Lys Ala Gln Leu Gln Leu Leu Gly
            35                  40                  45

Thr Val Cys Ile Leu Leu Ala Ser Lys Leu Arg Glu Thr Thr Pro Leu
        50                  55                  60

Thr Ile Glu Lys Leu Cys Ile Tyr Thr Asp Gln Ala Val Ala Pro Trp
65                  70                  75                  80

Gln Leu Arg Glu Trp Glu Val Leu Val Leu Gly Lys Leu Lys Trp Asp
                85                  90                  95

Leu Ala Ala Val Ile Ala His Asp Phe Leu Ala Leu Ile Leu His Arg
                100                 105                 110

Leu Ser Leu Pro Ser Asp Arg Gln Ala Leu Val Lys Lys His Ala Gln
            115                 120                 125

Thr Phe Leu Ala Leu Cys Ala Thr Asp Tyr Thr Phe Ala Met Tyr Pro
        130                 135                 140

Pro Ser Met Ile Ala Thr Gly Ser Ile Gly Ala Ala Val Ile Gly Leu
145                 150                 155                 160

Gly Ala Cys Ser Met Ser Ala Asp Glu Leu Thr Glu Leu Leu Ala Gly
                165                 170                 175

Ile Thr Gly Thr Glu Val Asp Cys Leu Arg Ala Cys Gln Glu Gln Ile
            180                 185                 190

Glu Ala Ala Leu Arg Glu Ser Leu Arg Glu Ala Ala Gln Thr Ala Pro
        195                 200                 205

Ser Pro Val Pro Lys Ala Pro Arg Gly Ser Ser Gln Gly Pro Ser
    210                 215                 220

Gln Thr Ser Thr Pro Thr Asp Val Thr Ala Ile His Leu
225                 230                 235
```

(2) INFORMATION FOR SEQ ID NO:25:

(i) SEQUENCE CHARACTERISTICS:
        (A) LENGTH: 106 amino acids
        (B) TYPE: amino acid (D) TOPOLOGY: unknown (ii) MOLECULE TYPE: protein (xi) SEQUENCE DESCRIPTION: SEQ ID NO:25:

```
Met Arg Ala Ile Leu Val Asp Trp Leu Val Glu Val Gly Glu Glu Tyr
1               5                   10                  15

Lys Leu Gln Asn Glu Thr Leu His Leu Ala Val Asn Tyr Ile Asp Arg
            20                  25                  30

Phe Leu Ser Ser Met Ser Val Leu Arg Gly Lys Leu Gln Leu Val Gly
        35                  40                  45

Thr Ala Ala Met Leu Leu Ala Ser Lys Phe Glu Glu Ile Tyr Pro Pro
    50                  55                  60

Glu Val Ala Glu Phe Val Tyr Ile Thr Asp Asp Thr Tyr Thr Lys Lys
65                  70                  75                  80

Gln Val Leu Arg Met Glu His Leu Val Leu Lys Val Leu Thr Phe Asp
            85                  90                  95

Leu Ala Ala Pro Thr Val Asn Gln Phe Leu
            100                 105
```

(2) INFORMATION FOR SEQ ID NO:26:

(i) SEQUENCE CHARACTERISTICS:
        (A) LENGTH: 116 amino acids
        (B) TYPE: amino acid
        (D) TOPOLOGY: unknown (ii) MOLECULE TYPE: protein (xi) SEQUENCE DESCRIPTION: SEQ ID NO:26:

```
Met Arg Ala Ile Leu Val Asp Trp Leu Val Met Arg Ala Ile Leu Ile
1               5                   10                  15

Asp Trp Leu Val Gln Val Gln Met Lys Phe Arg Leu Leu Gln Glu Thr
            20                  25                  30

Met Tyr Met Thr Val Ser Ile Ile Asp Arg Phe Met Gln Asn Asn Cys
        35                  40                  45

Val Pro Lys Lys Met Leu Gln Leu Val Gly Val Thr Ala Met Phe Ile
    50                  55                  60

Ala Ser Lys Tyr Glu Glu Met Tyr Pro Pro Glu Ile Gly Asp Phe Ala
65                  70                  75                  80

Phe Val Thr Asp Asn Thr Tyr Thr Lys His Gln Ile Arg Gln Met Glu
            85                  90                  95

Met Lys Ile Leu Arg Ala Leu Asn Phe Gly Leu Gly Arg Pro Leu Pro
            100                 105                 110

Leu His Phe Leu
        115
```

(2) INFORMATION FOR SEQ ID NO:27:

(i) SEQUENCE CHARACTERISTICS:
        (A) LENGTH: 106 amino acids
        (B) TYPE: amino acid
        (D) TOPOLOGY: unknown (ii) MOLECULE TYPE: protein (xi) SEQUENCE DESCRIPTION: SEQ ID NO:27:

```
Met Arg Ala Ile Leu Val Asp Trp Leu Val Gln Val His Ser Lys Phe
1               5                   10                  15

Arg Leu Leu Gln Glu Thr Leu Tyr Met Cys Val Gly Ile Met Asp Arg
```

-continued

```
                20                  25                  30
Phe Leu Gln Val Gln Pro Val Ser Arg Lys Lys Leu Gln Leu Val Gly
            35                  40                  45

Ile Thr Ala Leu Leu Ala Ser Lys Tyr Glu Glu Met Phe Ser Pro
 50                  55                  60

Asn Ile Glu Asp Phe Val Tyr Ile Thr Asp Asn Ala Tyr Thr Ser Ser
 65                  70                  75                  80

Gln Ile Arg Glu Met Glu Thr Leu Ile Leu Lys Glu Leu Lys Phe Glu
                85                  90                  95

Leu Gly Arg Pro Leu Pro Leu His Phe Leu
                100                 105
```

(2) INFORMATION FOR SEQ ID NO:28:

(i) SEQUENCE CHARACTERISTICS:
        (A) LENGTH: 105 amino acids
        (B) TYPE: amino acid
        (D) TOPOLOGY: unknown (ii) MOLECULE TYPE: protein (xi) SEQUENCE DESCRIPTION: SEQ ID NO:28:

```
Leu Gln Ile Phe Phe Thr Asn Val Ile Gln Ala Leu Gly Glu His Leu
 1               5                  10                  15

Lys Leu Arg Gln Gln Val Ile Ala Thr Ala Val Tyr Phe Lys Arg
                20                  25                  30

Phe Tyr Ala Arg Tyr Ser Leu Lys Ser Ile Asp Pro Val Leu Met Ala
            35                  40                  45

Pro Thr Cys Val Phe Leu Ala Ser Lys Val Glu Glu Ile Leu Lys Thr
 50                  55                  60

Arg Phe Ser Tyr Ala Phe Pro Lys Glu Phe Pro Tyr Arg Met Asn His
 65                  70                  75                  80

Ile Leu Glu Cys Glu Phe Tyr Leu Leu Glu Leu Met Asp Cys Cys Leu
                85                  90                  95

Ile Val Tyr His Pro Tyr Arg Pro Leu
                100                 105
```

(2) INFORMATION FOR SEQ ID NO:29:

(i) SEQUENCE CHARACTERISTICS:
        (A) LENGTH: 104 amino acids
        (B) TYPE: amino acid
        (D) TOPOLOGY: unknown (ii) MOLECULE TYPE: protein (xi) SEQUENCE DESCRIPTION: SEQ ID NO:29:

```
Met Arg Ala Ile Leu Leu Asp Trp Leu Met Glu Val Cys Glu Val Tyr
 1               5                  10                  15

Lys Leu His Arg Glu Thr Phe Tyr Leu Ala Gln Asp Phe Phe Asp Arg
                20                  25                  30

Tyr Met Ala Glu Asn Val Val Lys Thr Leu Leu Gln Leu Ile Gly Ile
            35                  40                  45

Ser Ser Leu Phe Ile Ala Ala Lys Leu Glu Glu Ile Tyr Pro Pro Lys
 50                  55                  60

Leu His Gln Phe Ala Tyr Val Thr Asp Gly Ala Cys Ser Gly Asp Glu
 65                  70                  75                  80

Ile Leu Thr Met Glu Leu Met Ile Met Lys Ala Leu Lys Trp Arg Leu
                85                  90                  95
```

Ser Pro Leu Thr Ile Val Ser Trp
            100

(2) INFORMATION FOR SEQ ID NO:30:

(i) SEQUENCE CHARACTERISTICS:
        (A) LENGTH: 1462 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:30:

| | |
|---|---:|
| TGATCAAGTT GACACTCAAT ATTAACCCTC ATAGACTGTG ATCCCTATGT TGCTGCCTTC | 60 |
| CCTCGTTTCT ATTGCTCTTT GGCCCCAACC CAAATAAGGT TCCTTGGGAC ACACTAAAGA | 120 |
| AGGAGGTGGA GTTCGAAGGG GAGGAGAGAT GTGAGCGAGG CAGGCAGGGA AGCTCTGCTC | 180 |
| GCCCACTGCC CAATCCTCAC CTCTCTTCTC CTCCACCTTC TGTCTCTGCC CTCACCTCTC | 240 |
| CTCTGAAAAC CCCCTATTGA GCCAAAGGAA GGAGATGAGG GGAATGCTTT TGCCTTCCCC | 300 |
| CTCCAAAACA AAACAAAAA CAAACACACT TTTCCAGTCC AGAGAAAGCA GGGGAGTGAG | 360 |
| GGGTCACAGA GCTGGCCATG CAGCTGCTGG GCTGTGAGGT AGACCCGGTC CTCAGAGCCA | 420 |
| CGAGGGACTG CAACCTACTC CAAGTTGACC GTGTCCTGAA GAACCTGCTT GCTATCAAGA | 480 |
| AGCGCTACCT TCAGTAATGC TCCTACTTCA AGTGTGTGCA GAAGGCCATC CAGCCGTACA | 540 |
| TGCACAGGAT GGTGCCACTT CTGATGGTGG CCATTTGATT GGTGCCACTT CTGATGGTGG | 600 |
| CCAACATGAT TGAACCATTT GGGATGGAAA AGCACCTTTA CTCTCAGCCA CCTGTTAACT | 660 |
| AATGCTGGAG GTCTGTGAGG AACAGAAGTG TGAAGAAAAG GTTTTCCCTC TGGCCACGAT | 720 |
| TTACCTGGAC TGTTTCTTCG CCAGGATCCC AACTTCAAAG TCCCATCTGC AACTCCTGGG | 780 |
| TGCTGTCTGC ATGTTCCTGG CCTCCAGGCT CAAAGAGTCC AGCCCACTGA CTGCCAAAAA | 840 |
| GCTGTGCATT TATACCGACA ACTCCATCAA GCCTCAGGAG CTGCTGGAGT GGGAACTGGT | 900 |
| GGTGTTGGGA AAGTTGAAGT GGAACCTGGC AGCTGTCACG CCTCATGACT TCATTTAGTA | 960 |
| CATCTTGCAC AAGCTGCCCC AGCAGCGGGA GAAGCTGTCT CCAATCTGCA AGCAAGTCCA | 1020 |
| GAACTTCAAT GCTCTGTATG CAATGTACCC GCCATCAATG GTTGCAACTG GAAGTGTAGG | 1080 |
| AGCAGCTATC TGTGGACTTC AGCAACATGA GGAAGTGAGC TCACTCCCTT GCAATGCCCT | 1140 |
| GACTGAGCTG CTGGCAAAGA TCACCAACAC AGATGTGGAT TGTCTCAAAA GCCAACCGGG | 1200 |
| AGCATATTGA GGTGGTCTTC CTCAACAGCC TGCAGCAGTG CCATCAGGAC CAGCAGGACA | 1260 |
| GATCCAAGTC AGAGGATGAA CTGGGCCAAG CAGCACCCCT ATAGACCTGT GAGATATCGA | 1320 |
| CCTGTGAGGA TGGCAGTCCA GCTGAGAGGC GCATTCATAA TCTGCTGTCT CCTTCTTTCT | 1380 |
| GGTTATGTTT TGTTCTTTGT ATCTTAGGGC GAAACTTAAA AAAAAAACC TCTGCCCCCA | 1440 |
| CATAGTTCGT GTTTAAAGAT CT | 1462 |

(2) INFORMATION FOR SEQ ID NO:31:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (xi) SEQUENCE DESCRIPTION: SEQ ID NO:31:

```
Met Gln Leu Leu Gly Cys Glu Val Asp Pro Val Leu Arg Ala Thr Arg
1               5                  10                 15

Asp Cys Asn Leu Leu Gln Val Asp Arg Val Leu Lys Asn Leu Leu Ala
            20                  25                 30

Ile Lys Lys Arg Tyr Leu Gln Cys Ser Tyr Phe Lys Cys Val Gln Lys
        35                  40                 45

Ala Ile Gln Pro Tyr Met His Arg Met Val Pro Leu Leu Met Val Met
50                  55                  60

Leu Glu Val Cys Glu Glu Gln Lys Cys Glu Glu Lys Val Phe Pro Leu
65                  70                  75                 80

Ala Thr Ile Tyr Leu Asp Cys Phe Phe Ala Arg Ile Pro Thr Ser Lys
                85                  90                 95

Ser His Leu Gln Leu Leu Gly Ala Val Cys Met Phe Leu Ala Ser Arg
            100                 105                110

Leu Lys Glu Ser Ser Pro Leu Thr Ala Lys Lys Leu Cys Ile Tyr Thr
        115                 120                125

Asp Asn Ser Ile Lys Pro Gln Glu Leu Leu Glu Gln Glu Leu Val Val
130                 135                 140

Leu Gly Lys Leu Lys Trp Asn Leu Ala Ala Val Thr Pro His Asp Phe
145                 150                 155                160

Ile Tyr Ile Leu His Lys Leu Pro Gln Gln Arg Glu Lys Leu Ser Ala
                165                 170                175

Met Tyr Pro Pro Ser Met Val Ala Thr Gly Ser Val Gly Ala Ala Ile
            180                 185                 190

Cys Gly Leu Gln Gln His Glu Glu Val Ser Ser Leu Pro Cys Asn Ala
        195                 200                 205

Leu Thr Glu Leu Leu Ala Lys Ile Thr Asn Thr Asp Val Asp Cys Leu
210                 215                 220

Lys Ala Asn Arg Glu His Ile Glu Val Val Phe Leu Asn Ser Leu Gln
225                 230                 235                240

Gln Cys His Gln Asp Gln Gln Asp Arg Ser Lys Ser Glu Asp Glu Leu
            245                 250                 255

Gly Gln Ala Ser Thr Pro Ile Asp Leu Asp Ile Asp Leu
        260                 265
```

(2) INFORMATION FOR SEQ ID NO:32:

(i) SEQUENCE CHARACTERISTICS:
        (A) LENGTH: 1901 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:32:

```
AAGCTTCCAG ATTAGAAAAG AAAAAATAAA ACTATCTTTA TTTGCAGATG ACATGATCGG     60

TCCATTCTCA TGCTGCTTAT AAAGACATAC CCAAGACTGG ATAATTTATA AAGGAAAGAG    120

GTTTGGCTCA CAGTTCCCCA TGGGTGGAGA GGCCTCACAA TCATGGCGAA AGAGCAAGGA    180

GCATCTCACA TGGCAGCAGG CAAGAAAAGA ATGAGAGCCA CGCCAGAGGG AAACCCCTTA    240

TAAAATCATC AGATCTCGAG AGACTTATTC ACTGTCAGGA GAACAGTATG GAGGAAACGC    300

CCTTATGATT CAATTATCTC GCACTGTGTT CCTCCCACAA CACATGGGAA TTATGGGAGC    360

TACAATTCAA GATGAGATTT GGGTGGAGAC ACAGCCAAAC CATATCAATC TTTTTTTTCT    420

TATTCTTTTT TTTTTTTTTT TTTTTTTTGA GATGGAGTCC CACTCTGTTA TCTAGGCTGG    480
```

```
AGTGCAGTGG TGTGTGATCT TGGCTCACTG CAACCTCAGC CTCCCAGGTT CAAGCGATTC    540

TCCTGCCTCA GACTCCTGAA TAGCTGAAAT TACAGGCACC TGCCACTACG CCTGGCAAAT    600

ATTTTTTGTT TGTTTGTTTG TTTGTTTGTT TGTTTTGAGA CAGAGTCTCT CTCTGTCGCC    660

CAGGCTGGAG TGCAGTGGGC GCGATCTCAG CTCACTGCAA ACTCTGCTCC CGGGTTCAAG    720

CCATTCTCCT GCCTCAGCTC CCAAGTAGCT GGGACTACAG GCGCCCACCA CCACCATGCC    780

AGGCTAATTT TTTGTATTTT TAGTAGAGAC AGGGTTTCAC CGTGTTAGCC AGGATGGTCT    840

CAATCTCCTG ACCTCGTGAT CCGCCCACCT CGGCCTCCCA AAGTGCTGGG ATTACAGGCG    900

TGAGCCACTA TGCCCAACCG TATCAATCTT GTATATAGAA AAACCTAAGG AATCTACAAA    960

AAAACCCTAT TATAACTAAT ATAATAATAA TCTGCAAAGT TGTAGACTAT GAGATCAATA   1020

TACAAAAATT AACTCAATTT CTTTACATGT ACAATGAATA ACCCCAAAAC AAAACTGGGA   1080

ATATAATTCT ATTTTTAATA GTATCACAAA GAATGACAAT ACTTAGAAAC AAATGATGGG   1140

CGCTAGCTTG CACTCCCGCC CTGCCTGTGC GCTGCCCGAG TGTGGAGCTG CTATGCTGCG   1200

AAGGCTCGAG GACCCGCAGA CGCCAGGGGA TCAGCGCGTC CTGCAGAGCT TGCTCCCCTT   1260

GGAGTAGCGC TGCGTGCACT GCGCCTACTT CCAGTGCGTG CAAAGGGAGA GCAAGCCGCA   1320

CATGCGGAAG ATGCTGGTTT ACTGGATGCT GGAGGTGTGT GAGGAGCAGT GCTGTGAGGA   1380

GGAGCAGTGC TGTAAGGAGG AAGTCTTTCC CCTGGCCATG AACCACCTGC ATGCTACCTG   1440

TCCTACGTCC CCACCCACCC GAAAGGCACA GTTGCAGCTC TTGGTTGCGG TCTCCATGCG   1500

GCTGGCCTCC AAGCTGCGTA AGACTGGGCC CATGACCATT GAGAAAATGT GCATCTACAC   1560

CGACCACGCT GTCTCTCCCT GCCAGTTGCG GGACTGGGAG GTGATGGTCC TGGGGAAGCT   1620

CAAATGGGAC CTGGCCGCTG TGATTGCTCA TGACTTCTTG GCCCTCATTC TGCACCGACA   1680

CAGATAACCA TATGTGATAT ATATCAATAC AATGGAATAT GGCCTGGCAT GCTGGCTTAC   1740

GCTGTAATCC TGCACTTTGG GAGGCCAAAG TGGAGGATCA CTTGAGCCGA GGAGTTCAAG   1800

GCCAGCCTGG GCACAAAGTG AGACTCCTTC TAAAAAAATA AAATAAAATA AAAAATAAAA   1860

ACAATGTAAT ATTATTCAGC CATAGAAAGG AATAAAGTAC T                      1901
```

(2) INFORMATION FOR SEQ ID NO:33:

(i) SEQUENCE CHARACTERISTICS:
        (A) LENGTH: 215 amino acids
        (B) TYPE: amino acid
        (D) TOPOLOGY: unknown (ii) MOLECULE TYPE: protein (xi) SEQUENCE DESCRIPTION: SEQ ID NO:33:

```
Trp Ala Leu Ala Cys Thr Pro Ala Leu Pro Val Arg Cys Pro Ser Val
1               5                   10                  15

Glu Leu Leu Cys Cys Glu Gly Ser Arg Asp Pro Gln Thr Pro Gly Asp
            20                  25                  30

Gln Arg Val Leu Gln Ser Leu Leu Pro Leu Glu Arg Cys Val His Cys
        35                  40                  45

Ala Tyr Phe Gln Cys Val Gln Arg Glu Ser Lys Pro His Met Arg Lys
    50                  55                  60

Met Leu Val Tyr Trp Met Leu Glu Val Cys Glu Cys Cys Glu Glu
65                  70                  75                  80

Glu Cys Cys Lys Glu Glu Val Phe Pro Leu Ala Met Asn His Leu His
                85                  90                  95
```

```
Ala Thr Cys Pro Thr Ser Pro Pro Thr Arg Lys Ala Gln Leu Gln Leu
            100                 105                 110

Leu Val Ala Val Ser Met Arg Leu Ala Ser Lys Leu Arg Lys Thr Gly
        115                 120                 125

Pro Met Thr Ile Glu Lys Met Cys Ile Tyr Thr Asp His Ala Val Ser
130                 135                 140

Pro Cys Gln Leu Arg Asp Trp Glu Val Met Val Leu Gly Lys Leu Lys
145                 150                 155                 160

Trp Asp Leu Ala Ala Val Ile Ala His Asp Phe Leu Ala Leu Ile Leu
                165                 170                 175

His Arg Arg Gln Ala Leu Val Lys Lys His Ala Gln Ile Phe Leu Ala
            180                 185                 190

Val Cys Ala Thr Asp Tyr Thr Phe Ala Met Tyr Pro Pro Ser Ser Cys
        195                 200                 205

Glu Asn Asn Pro Asn Ala Cys
210                 215
```

(2) INFORMATION FOR SEQ ID NO:34:

(i) SEQUENCE CHARACTERISTICS:
        (A) LENGTH: 1317 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:34:

```
GAGCTCGATC AGTACACTCG TTTGTTTAAT TGATAATTGT CCTGAATTAT GCCGGCTCCT    60

GCAGCCCCCT CACGCTCACG AATTCAGTCC CAGGGCAAAT TCTAAAGGTG AAGGGACGTC   120

TACACCCCCA ACAAAACCAA TTAGGAACCT TCGGTGGGTC TTGTCCCAGG CAGAGGGGAC   180

TAATATTTCC AGCAATTTAA TTTCTTTTTT AATTAAAAAA AATGAGTCAG AATGGAGATC   240

ACTGTTTCTC AGCTTTCCAT TCAGAGGTGT GTTTCTCCCG GTTAAATTGC CGGCACGGGA   300

AGGGAGGGGG TGCAGTTGGG GACCCCCGCA AGGACCGACT GGTCAAGGTA GGAAGGCAGC   360

CCGAAGAGTC TCCAGGCTAG AAGGACAAGA TGAAGGAAAT GCTGGCCACC ATCTTGGGCT   420

GCTGCTGGAA TTTTCGGGCA TTTATTTTAT TTTATTTTTT GAGCGAGCGC ATGCTAAGCT   480

GAAATCCCTT TAACTTTTAG GTTACCCCTT GGGCATTTGC AACGACGCCC CTGTGCGCCG   540

GAATGAAACT TGCACAGGGG TTGTGTGCCC GGTCCTCCCC GTCCTTGCAT GCTAAATTAG   600

TTCTTGCAAT TTACACGTGT TAATGAAAAT GAAAGAAGAT GCAGTCGCTG AGATTCTTTG   660

GCCGTCTGTC CGCCCGTGGG TGCCCTCGTG GCGTTCTTGG AAATGCGCCC ATTCTGCCGG   720

CTTGGATATG GGGTGTCGCC GCGCCCCAGT CACCCCTTCT CGTGGTCTCC CCAGGCTGCG   780

TGCTGGCCGG CCTTCCTAGT TGTCCCCTAC TGCAGAGCCA CCTCCACCTC ACCCCCTAAA   840

TCCCGGGACC CACTCGAGGC GGACGGGCCC CCTGCACCCC TCTCGGCGGG GAGAAAGGCT   900

GCAGCGGGGC GATTTGCATT TCTATGAAAA CCGGACTACA GGGCAACTG CCCGCAGGGC    960

AGCGCGGCGC CTCAGGGATG GCTTTTCGTC TGCCCCTCGC TGCTCCCGGC GTTCTGCCCG  1020

CGCCCCCTCC CCCTGCGCCC GCCCCGCCC CCTCCCGCT CCCATTCTCT GCGGGCTTT    1080

GATCTTTGCT TAACAACAGT AACGTCACAC GGACTACAGG GGAGTTTTGT TGAAGTTGCA  1140

AAGTCCTGGA GCCTCCAGAG GGCTGTCGGC GCAGTAGCAG CGAGCAGCAG AGTCCGCACG  1200

CTCCGGCGAG GGGCAGAAGA GCGCGAGGGA GCGCGGGGCA GCAGAAGCGA GAGCCGAGCG  1260
```

CGGACCCAGC CAGGACCCAC AGCCCTCCCC AGCTGCCCAG GAAGAGCCCC AGCCATG         1317

(2) INFORMATION FOR SEQ ID NO:35:

(i) SEQUENCE CHARACTERISTICS:
        (A) LENGTH: 1624 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:35:

```
GAGCTCGAGC CACGCCATGC CCGCTGCACG TGCCAGCTTG GCCAGCACAT CAGGGCGCTG      60

GTCTCTCCCC TTCCTCCTGG AGTGAAATAC ACCAAAGGGC GCGGTGGGGG TGGGGGGTGA     120

CGGGAGGAAG GAGGTGAAGA AACGCCACCA GATCGTATCT CCTGTAAAGA CAGCCTTGAC     180

TCAAGGATGC GTTAGAGCAC GTGTCAGGGC CGACCGTGCT GGCGGCGACT TCACCGCAGT     240

CGGCTCCCAG GGAGAAAGCC TGGCGAGTGA GGCGCGAAAC CGGAGGGGTC GGCGAGGATG     300

CGGGCGAAGG ACCGAGCGTG GAGGCCTCAT GCTCCGGGGA AAGGAAGGGG TGGTGGTGTT     360

TGCGCAGGGG GAGCGAGGGG GAGCCGGACC TAATCCCTTC ACTCGCCCCC TTCCCTCCCG     420

GGCCATTTCC TAGAAAGCTG CATCGGTGTG GCCACGCTCA GCGCAGACAC CTCGGGCGGC     480

TTGTCAGCAG ATGCAGGGGC GAGGAAGCGG GTTTTTCCTG CGTGGCCGCT GGCGCGGGGG     540

AACCGCTGGG AGCCCTGCCC CCGGCCTGCG GCGGCCCTAG ACGCTGCACC GCGTCGCCCC     600

ACGGCGCCCG AAGAGCCCCC AGAAACACGA TGGTTTCTGC TCGAGGATCA CATTCTATCC     660

CTCCAGAGAA GCACCCCCCT TCCTTCCTAA TACCCACCTC TCCCTCCCTC TTCTTCCTCT     720

GCACACACTC TGCAGGGGGG GGCAGAAGGG ACGTTGTTCT GGTCCCTTTA ATCGGGGCTT     780

TCGAAACAGC TTCGAAGTTA TCAGGAACAC AGACTTCAGG GACATGACCT TTATCTCTGG     840

GTATGCGAGG TTGCTATTTT CTAAAATCAC CCCCTCCCTT ATTTTTCACT TAAGGGACCT     900

ATTTCTAAAT TGTCTGAGGT CACCCCATCT TCAGATAATC TACCCTACAT TCCTGGATCT     960

TAAATACAAG GGCAGGAGGA TTAGGATCCG TTTTTGAAGA AGCCAAAGTT GGAGGGTCGT    1020

ATTTTGGCGT GCTACACCTA CAGAATGAGT GAAATTAGAG GGCAGAAATA GGAGTCGGTA    1080

GTTTTTTGTG GGTTGCCCTG TCCGGGCCCC TGGCATGCAG GCTTGGATGG AGGGAGAGGG    1140

GTTGGGGGTT GCGGGGGACC GCGTTTGAAG TTGGGTCGGG CCAGCTGCTG TTCTCCTTAA    1200

TAACGAGAGG GGAAAAGGAG GGAGGGAGGG AGAGATTGAA AGGAGGAGGG GAGGACCGGG    1260

AGGGGAGGAA AGGGGAGGAG GAACCAGAGC GGGGAGCGCG GGGAGAGGGA GGAGAGCTAA    1320

CTGCCCAGCC AGCTTCGGTC ACGCTTCAGA GCGGAGAAGA GCGAGCAGGG GAGAGCGAGA    1380

CCAGTTTTAA GGGGAGGACC GGTGCGAGTG AGGCAGCCCC TAGGCTCTGC TCGCCCACCA    1440

CCCAATCCTC GCCTCCCTTC TGCTCCACCT TCTCTCTCTG CCCTCACCTC TCCCCCGAAA    1500

ACCCCCTATT TAGCCAAAGG AAGGAGGTCA GGGAACGCTC TCCCCTCCCC TTCCAAAAAA    1560

CAAAAACAGA AAACCCTTT TCCAGGCCGG GGAAAGCAGG AGGGAGAGGG CGCGGGCTGC    1620

CATG                                                                1624
```

(2) INFORMATION FOR SEQ ID NO:36:

(i) SEQUENCE CHARACTERISTICS:
        (A) LENGTH: 1317 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:36:

```
GAGCTCGATC AGTACACTCG TTTGTTTAAT TGATAATTGT CCTGAATTAT GCCGGCTCCT      60
GCAGCCCCCT CACGCTCACG AATTCAGTCC CAGGGCAAAT TCTAAAGGTG AAGGGACGTC     120
TACACCCCCA ACAAAACCAA TTAGGAACCT TCGGTGGGTC TTGTCCCAGG CAGAGGGGAC     180
TAATATTTCC AGCAATTTAA TTTCTTTTTT AATTAAAAAA AATGAGTCAG AATGGAGATC     240
ACTGTTTCTC AGCTTTCCAT TCAGAGGTGT GTTTCTCCCG GTTAAATTGC CGGCACGGGA     300
AGGGAGGGGG TGCAGTTGGG GACCCCCGCA AGGACCGACT GGTCAAGGTA GGAAGGCAGC     360
CCGAAGAGTC TCCAGGCTAG AAGGACAAGA TGAAGGAAAT GCTGGCCACC ATCTTGGGCT     420
GCTGCTGGAA TTTTCGGGCA TTTATTTTAT TTTATTTTTT GAGCGAGCGC ATGCTAAGCT     480
GAAATCCCTT TAACTTTTAG GTTACCCCTT GGGCATTTGC AACGACGCCC CTGTGCGCCG     540
GAATGAAACT TGCACAGGGG TTGTGTGCCC GGTCCTCCCC GTCCTTGCAT GCTAAATTAG     600
TTCTTGCAAT TTACACGTGT TAATGAAAAT GAAAGAAGAT GCAGTCGCTG AGATTCTTTG     660
GCCGTCTGTC CGCCCGTGGG TGCCCTCGTG GCGTTCTTGG AAATGCGCCC ATTCTGCCGG     720
CTTGGATATG GGGTGTCGCC GCGCCCCAGT CACCCCTTCT CGTGGTCTCC CCAGGCTGCG     780
TGCTGGCCGG CCTTCCTAGT TGTCCCCTAC TGCAGAGCCA CCTCCACCTC ACCCCCTAAA     840
TCCCGGGACC CACTCGAGGC GGACGGGCCC CCTGCACCCC TCTCGGCGGG GAGAAAGGCT     900
GCAGCGGGGC GATTTGCATT TCTATGAAAA CCGGACTACA GGGGCAACTG CCCGCAGGGC     960
AGCGCGGCGC CTCAGGGATG GCTTTTCGTC TGCCCCTCGC TGCTCCCGGC GTTCTGCCCG    1020
CGCCCCCTCC CCCTGCGCCC GCCCCCGCCC CCCTCCCGCT CCCATTCTCT GCCGGGCTTT    1080
GATCTTTGCT TAACAACAGT AACGTCACAC GGACTACAGG GGAGTTTTGT TGAAGTTGCA    1140
AAGTCCTGGA GCCTCCAGAG GGCTGTCGGC GCAGTAGCAG CGAGCAGCAG AGTCCGCACG    1200
CTCCGGCGAG GGGCAGAAGA GCGCGAGGGA GCGCGGGGCA GCAGAAGCGA GAGCCGAGCG    1260
CGGACCCAGC CAGGACCCAC AGCCCTCCCC AGCTGCCCAG GAAGAGCCCC AGCCATG      1317
```

(2) INFORMATION FOR SEQ ID NO:37:

(i) SEQUENCE CHARACTERISTICS:
            (A) LENGTH: 38 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:37:

```
TGGATGYTNG ARGTNTGYGA RGARCARAAR TGYGARGA                              38
```

(2) INFORMATION FOR SEQ ID NO:38:

(i) SEQUENCE CHARACTERISTICS:
            (A) LENGTH: 13 amino acids
            (B) TYPE: amino acid
            (D) TOPOLOGY: unknown (ii) MOLECULE TYPE: peptide (xi) SEQUENCE DESCRIPTION: SEQ ID NO:38:

```
Trp Met Leu Glu Val Cys Glu Glu Gln Lys Cys Glu Glu
1               5                   10
```

-continued

```
(2) INFORMATION FOR SEQ ID NO:39:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:39:

GTNTTYCCNY TNGCNATGAA YTAYTNGA                                    28

(2) INFORMATION FOR SEQ ID NO:40:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (xi) SEQUENCE DESCRIPTION: SEQ ID NO:40:

Val Phe Pro Leu Ala Met Asn Tyr Leu Asp
1               5                   10

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:41:

RTCNGTRTAD ATRCANARYT TYTC                                        24

(2) INFORMATION FOR SEQ ID NO:42:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (xi) SEQUENCE DESCRIPTION: SEQ ID NO:42:

Glu Lys Leu Cys Ile Tyr Thr Asp
1               5
```

D-TYPE CYCLIN AND USES RELATED THERETO

DESCRIPTION

This application is a continuation of application Ser. No. 07/888,178, filed on May 26, 1992, now abandoned, which is a continuation-in-part of U.S. Ser. No. 07/701,514 filed May 16, 1991 now abandoned and entitled "D-Type Cyclin and Uses Related Thereto" and also corresponds to and claims priority to Patent Cooperation Treaty Application (number not yet available) filed May 18, 1992 and entitled "D-Type Cyclin and Uses Related Thereto". The teachings of U.S. Ser. No. 07/701,514 now abandoned and the PCT Application filed May 18, 1992 are incorporated herein by reference.

FUNDING

Work described herein was supported by National Institutes of Health Grant GM39620 and the Howard Hughes Medical Institute. The United States Government has certain rights in the invention.

BACKGROUND OF THE INVENTION

A typical cell cycle of a eukaryotic cell includes the M phase, which includes nuclear division (mitosis) and cytoplasmic division or cytokinesis and interphase, which begins with the G1 phase, proceeds into the S phase and ends with the G2 phase, which continues until mitosis begins, initiating the next M phase. In the S phase, DNA replication and histone synthesis occurs, while in the G1 and G2 phases, no net DNA synthesis occurs, although damaged DNA can be repaired. There are several key changes which occur during the cell cycle, including a critical point in the G1 phase called the restriction point or start, beyond which a cell is committed to completing the S, G2 and M phases.

Onset of the M phase appears to be regulated by a common mechanism in all eukaryotic cells. A key element of this mechanism is the protein kinase $p34^{cdc2}$, whose activation requires changes in phosphorylation and interaction with proteins referred to as cyclins, which also have an ongoing role in the M phase after activation.

Cyclins are proteins that were discovered due to their intense synthesis following the fertilization of marine invertebrate eggs (Rosenthal, E. T. et al., *Cell* 20:487–494 (1980)). It was subsequently observed that the abundance of two types of cyclin, A and B, oscillated during the early cleavage divisions due to abrupt proteolytic degradation of the polypeptides at mitosis and thus, they derived their name (Evans, T. et al., *Cell* 33:389–396 (1983); Swenson, K. I. et al., *Cell* 47:867–870 (1986); Standart, N. et al., *Dev. Biol.* 124:248–258 (1987)).

Active rather than passive involvement of cyclins in regulation of cell division became apparent with the observation that a clam cyclin mRNA could cause activation of frog oocytes and entry of these cells into M phase (Swenson, K. I. et al., *Cell* 47:867–870 (1986)). Activation of frog oocytes is associated with elaboration of an M phase inducing factor known as MPF (Masui, Y. and C. L. Markert, *J. Exp. Zool.* 177:129–146 (1971); Smith, L. D. and R. E. Ecker, *Dev. Biol.* 25:232–247 (1971)). MPF is a protein kinase in which the catalytic subunit is the frog homolog of the cdc2 protein kinase (Dunphy, W. G. et al., *Cell* 54:423–431 (1988); Gautier, J. et al., *Cell* 54:433–439 (1988); Arion, D. et al., *Cell* 55:371–378 (1988)).

Three types of classes of cyclins have been identified to date: B, A and CLN cyclins. The B-type cyclin has been shown to act in mitosis by serving as an integral subunit of the cdc2 protein kinase (Booher, R. and D. Beach, *EMBO J.* 6:3441–3447 (1987); Draetta, G. et al., *Cell* 56:829–838 (1989); Labbe, J. C. et al., *Cell* 57:253–263 (1989); Labbe, J. C. et al., *EMBO J.* 8:3053–3058 (1989); Meijer, L. et al., *EMBO J.* 8:2275–2282 (1989); Gautier, J. et al., *Cell* 60:487–494 (1990)). The A-type cyclin also independently associates with the cdc2 kinase, forming an enzyme that appears to act earlier in the division cycle than mitosis (Draetta, G. et al., *Cell* 56:829–838 (1989); Minshull, J. et al., *EMBO J.* 9:2865–2875 (1990); Giordano, A. et al., *Cell* 58:981–990 (1989); Pines, J. and T. Hunter, *Nature* 346:760–763 (1990)). The functional difference between these two classes of cyclins is not yet fully understood.

Cellular and molecular studies of cyclins in invertebrate and vertebrate embryos have been accompanied by genetic studies, particularly in ascomycete yeasts. In the fission yeast, the cdc13 gene encodes a B-type cyclin that acts in cooperation with cdc2 to regulate entry into mitosis (Booher, R. and D. Beach, *EMBO J.*, 6:3441–3447 (1987); Booher, R. and D. Beach, *EMBO J.* 7:2321–2327 (1988); Hagan, I. et al., *J. Cell Sci.* 91:587–595 (1988); Solomon, M., *Cell* 54:738–740 (1988); Goebl, M. and B. Byers, *Cell* 54:433–439 (1988); Booher, R. N. et al., *Cell* 58:485–497 (1989)).

Genetic studies in both the budding yeast and fission yeast have revealed that cdc2 (or CDC28 in budding yeast) acts at two independent points in the cell cycle: mitosis and the so-called cell cycle "start" (Hartwell, L. H., *J. Mol. Biol.*, 104:803–817 (1971); Nurse, P. and Y. Bissett, *Nature* 292:558–560 (1981); Piggot, J. R. et al., *Nature* 298:391–393 (1982); Reed, S. I. and C. Wittenberg, *Proc. Nat. Acad. Sci. USA* 87:5697–5701 (1990)).

In budding yeast, the start function of the CDC28 protein also requires association of the catalytic subunit of the protein kinase with ancillary proteins that are structurally related to A and B-type cyclins. This third class of cyclin has been called the ClN class, and three genes comprising a partially redundant gene family have been described (Nash, R. et al., *EMBO J.* 7:4335–4346 (1988); Hadwiger, J. A. et al., *Prot. Natl. Acad. Sci. USA* 86:6255–6259 (1989); Richardson, H. E. et al., *Cell* 59:1127–1133 (1989)). The CLN genes are essential for execution of start and in their absence, cells become arrested in the G1 phase of the cell cycle. The CLN1 and CLN2 transcripts oscillate in abundance through the cell cycle, but the CLN3 transcript does not. In addition, the ClN2 protein has been shown to oscillate in parallel with its mRNA (Nash, R. et al., *EMBO J.* 7:4335–4346 (1988); Cross, F. R., *Mol. Cell. Biol.* 8:4675–4684 (1988); Richardson, H. E. et al., *Cell* 59:1127–1133 (1988); Wittenberg, et al., 1990)).

Although the precise biochemical properties conferred on cdc2/CDC28 by association with different cyclins have not been fully elaborated, genetic studies of cyclin mutants clearly establishes that they confer "G1" and "G2" properties on the catalytic subunit (Booher, R. and D. Beach, *EMBO J.* 6:3441–3447 (1987); Nash, R. et al., *EMBO J.* 7:4335–4346 (1988); Richardson, H. E. et al., *Cell* 56:1127–1133 (1989)).

cdc2 and cyclins have been found not only in embryos and yeasts, but also in somatic human cells. The function of the cdc2/cyclin B enzyme appears to be the same in human cells as in other cell types (Riabowol, K. et al., *Cell* 57:393–401 (1989)). A human A type cyclin has also been found in association with cdc2. No CLN type cyclin has yet been described in mammalian cells. A better understanding of the

SUMMARY OF THE INVENTION

The present invention relates to a novel class of cyclins, referred to as D-type cyclins, which are of mammalian origin and are a new family of cyclins related to, but distinct from, previously described A, B or CLN type cyclins. In particular, it relates to human cyclins, encoded by genes shown to be able to replace a CLN-type gene essential for cell cycle start in yeast, which complement a deficiency of a protein essential for cell cycle start and which, on the basis of protein structure, are on a different branch of the evolutionary tree from A, B or CLN type cyclins. Three members of the new family of D-type cyclins, referred to as the human D-type gene family, are described herein. They encode small (33–34 KDa) proteins which share an average of 57% identity over the entire coding region and 78% in the cyclin box. One member of this new cyclin family, cyclin D1 or CCND1, is 295 amino acid residues and has an estimated molecular weight of 33,670 daltons (Da). A second member, cyclin D2 or CCND2, is 289 amino acid residues and has an estimated molecular weight of 33,045 daltons. It has been mapped to chromosome 12p band p13. A third member, cyclin D3 or CCND3, is 292 amino acid residues and has an estimated molecular weight of approximately 32,482 daltons. It has been mapped to chromosome 6p band p21. The D-type cyclins described herein are the smallest cyclin proteins identified to date. All three cyclin genes described herein are interrupted by an intron at the same position. D-type cyclins of the present invention can be produced using recombinant techniques, can be synthesized chemically or can be isolated or purified from sources in which they occur naturally. Thus, the present invention includes recombinant D-type cyclins, isolated or purified D-type cyclins and synthetic D-type cyclins.

The present invention also relates to DNA or RNA encoding a D-type cyclin of mammalian origin, particularly of human origin, as well as to antibodies, both polyclonal and monoclonal, specific for a D-type cyclin of mammalian, particularly human, origin.

The present invention further relates to a method of isolating genes encoding other cyclins, such as other D-type cyclins and related (but non-D type) cyclins. It also has diagnostic and therapeutic aspects. For example, it relates to a method in which the presence and/or quantity of a D-type cyclin (or cyclins) in tissues or biological samples, such as blood, urine, feces, mucous or saliva, is determined, using a nucleic acid probe based on a D-type cyclin gene or genes described herein or an antibody specific for a D-type cyclin. This embodiment can be used to predict whether cells are likely to undergo cell division at an abnormally high rate (i.e., if cells are likely to be cancerous), by determining whether their cyclin levels or activity are elevated (elevated level of activity being indicative of an increased probability that cells will undergo an abnormally high rate of division). The present method also relates to a diagnostic method in which the occurrence of cell division at an abnormally high rate is assessed based on abnormally high levels of a D-type cyclin(s), a gene(s) encoding a D-type cyclin(s) or a transcription product(s) (RNA).

In addition, the present invention relates to a method of modulating (decreasing or enhancing) cell division by altering the activity of at least one D-type cyclin, such as D2, D2 or D3 in cells. The present invention particularly relates to a method of inhibiting increased cell division by interfering with the activity or function of a D-type cyclin(s). In this therapeutic method, function of D-type cyclin(s) is blocked (totally or partially) by interfering with its ability to activate the protein kinase it would otherwise (normally) activate (e.g., p34$^{cdc2}$ or a related protein kinase), by means of agents which interfere with D-type cyclin activity, either directly or indirectly. Such agents include anti-sense sequences or other transcriptional modulators which bind D cyclin-encoding DNA or RNA; antibodies which bind either the D-type cyclin or a molecule with which a D-type cyclin must interact or bind in order to carry out its role in cell cycle start; substances which bind the D-type cyclin(s); agents (e.g., proteases) which degrade or otherwise inactivate the D-type cyclin(s); or agents (e.g., small organic molecules) which interfere with association of the D-type cyclin with the catalytic subunit of the kinase. The subject invention also relates to agents (e.g., oligonucleotides, antibodies, peptides) useful in the isolation, diagnostic or therapeutic methods described.

BRIEF DESCRIPTION OF THE FIGURES

FIGS. 2A and 2B show the human cyclin D1 nucleic acid sequence (SEQ ID No. 1) and amino acid sequence (SEQ ID No. 2), in which nucleotide numbers and amino acid numbers are on the right, amino acid numbers are given with the initiation methionine as number one and the stop codon is indicated by an asterisk.

FIGS. 3A and 3B show the human cyclin D2 nucleic acid sequence (SEQ ID No. 3) and amino acid sequence (SEQ ID No. 4) in which nucleotide numbers and amino acid numbers are on the right, amino acid numbers are given with the initiation methionine as number one and the stop codon is indicated by an asterisk.

FIGS. 4A and 4B show the human cyclin D3 nucleic acid sequence (SEQ ID No. 5) and amino acid sequence (SEQ ID No. 6), in which nucleotide numbers and amino acid numbers are on the right, amino acid numbers are given with the initiation methionine as number one and the stop codon is indicated by an asterisk.

FIG. 5A shows the amino acid sequence alignment of seven cyclin genes (CYCD1-Hs, SEQ ID No. 7; CYCA-Hs, SEQ ID No. 8; CYCA-Dm, SEQ ID No. 9; CYCB1-Hs, SEQ ID No. 10; CDC13-Sp, SEQ ID No. 11; CLN1-Sc, SEQ ID No. 12; CLN3-Sc, SEQ ID No. 13), in which numbers within certain sequences indicate the number of amino acid residues omitted from the sequence as the result of insertion.

FIG. 6A is a comparison of several cDNA clones isolated from different cell lines. Open boxes represent the 1.7 kb small transcript containing the coding region of cyclin D1 gene. Shadowed boxes represent the 3' fragment present in the 4.8 kb long transcript. Restriction sites are given above each cDNA clone to indicate the alignment of these clones.

FIG. 6B shows the nucleotide sequence surrounding the first polyadenylation site for several cDNA clones (CYCD1-21, SEQ ID No. 14; CYCD1-H12, SEQ ID No. 15; CYCD1-HO34, SEQ ID No. 16; CYCD1-TO78, SEQ ID No. 17 and a genomic clone; CYCD1-GO68, SEQ ID No. 18).

FIG. 6C is a summary of the structure and alternative polyadenylation of the cyclin D1 gene. Open boxes represent the small transcript, the shadowed box represents the 3' sequence in the large transcript and the filled boxes indicate the coding regions.

FIGS. 7 through 7D show the protein sequence comparison of eleven mammalian cyclins (CYCD1-Hs, SEQ ID No. 19; CYL1-Mm, SEQ ID No. 20; CYCD2-Hs, SEQ ID No. 21; CYCL2-Mm, SEQ ID No. 22; CYCD3-Hs, SEQ ID No. 23; CYL3-Mm, SEQ ID No. 24; CYCA-Hs, SEQ ID No. 25; CYCB1-Hs, SEQ ID No. 26; CYCB2-Hs, SEQ ID No. 27; CYCC-Hs, SEQ ID No. 28; CYCE-Hs, SEQ ID No. 29).

FIGS. 9A and FIG. 9B show the nucleic acid sequence (SEQ ID No. 30) and amino acid sequence (SEQ ID No. 31) of a cyclin D2 pseudogene.

FIGS. 10A and FIG. 10B show is the nucleic acid sequence (SEQ ID No. 32) and the amino acid sequence (SEQ ID No. 33) of a cyclin D3 pseudogene.

FIG. 11 is the nucleic acid sequence (SEQ ID No. 34) of 1.3 kb of human cyclin D1 promoter; the sequence ends at initiation ATG codon and transcription starts at approximately nucleotide −160.

FIG. 12 is the nucleotide sequence (SEQ ID No. 35) of 1.6 kb of human cyclin D2 promoter; the sequence ends at initiation ATG codon and transcription starts at approximately nucleotide −170.

FIGS. 13A and FIG. 13B show is the nucleotide sequence (SEQ ID No. 36) of 3.2 kb of human cyclin D3 promoter; the sequence ends at initiation ATG codon and transcription starts at approximately nucleotide −160.

DETAILED DESCRIPTION OF THE INVENTION

As described herein, a new class of mammalian cyclin proteins, designated D-type cyclins, has been identified, isolated and shown to serve as a control element for the cell cycle start, in that they fill the role of a known cyclin protein by activating a protein kinase whose activation is essential for cell cycle start, an event in the G1 phase at which a cell becomes committed to cell division. Specifically, human D-type cyclin proteins, as well as the genes which encode them, have been identified, isolated and shown to be able to replace CLN type cyclin known to be essential for cell cycle start in yeast. The chromosomal locations of CCND2 and CCND3 have also been mapped.

As a result, a new class of cyclins (D type) is available, as are DNA and RNA encoding the novel D-type cyclins, antibodies specific for (which bind to) D-type cyclins and methods of their use in the identification of additional cyclins, the detection of such proteins and oligonucleotides in biological samples, the inhibition of abnormally increased rates of cell division and the identification of inhibitors of cyclins.

The following is a description of the identification and characterization of human D-type cyclins and of the uses of these novel cyclins and related products.

Isolation and Characterization of Human Cyclin D1, D2 and D3

Figure 1:
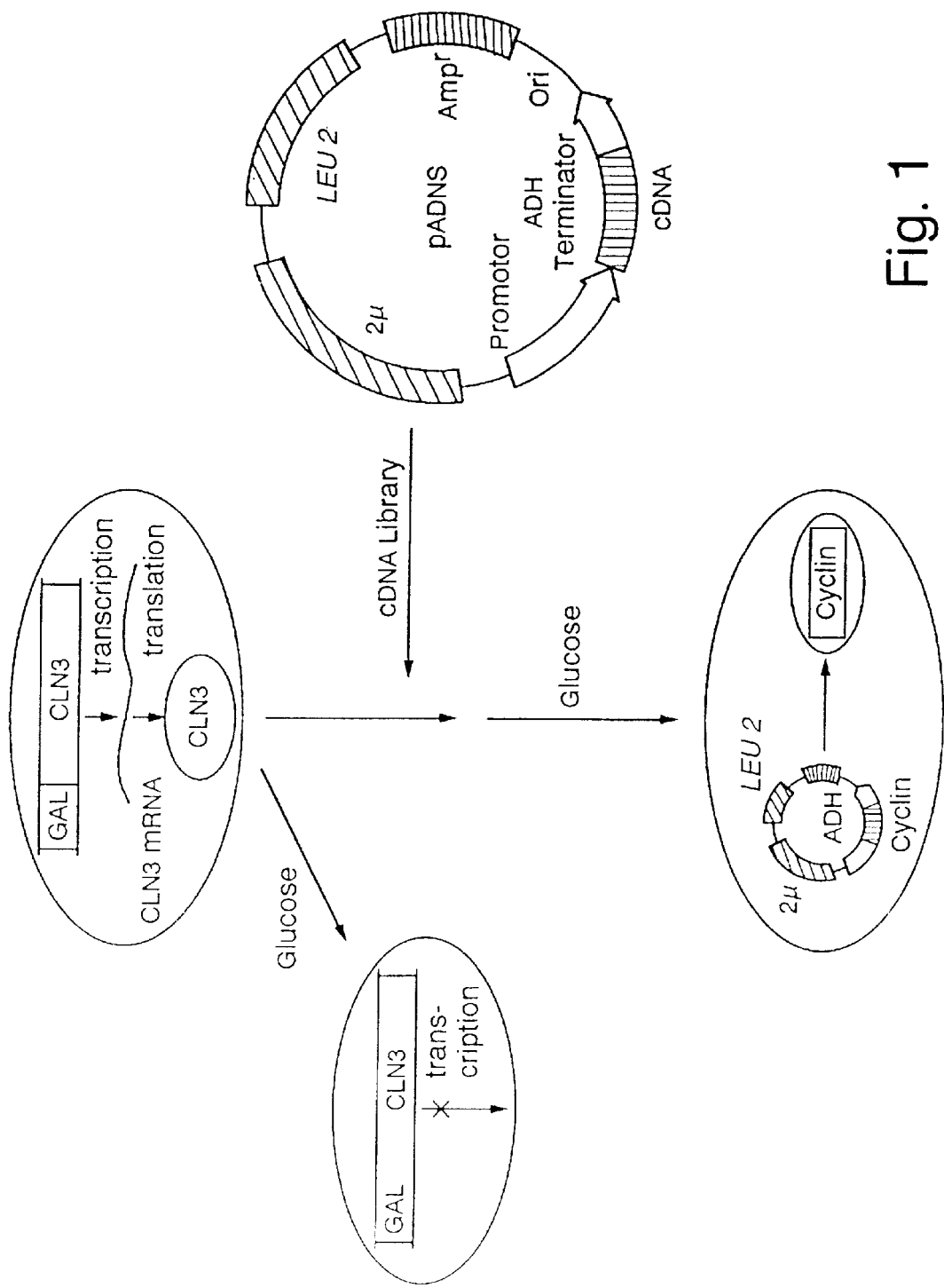
FIG. 1 is a schematic representation of a genetic screen for human cyclin genes.

As represented schematically in FIG. 1 and described in detail in Example 1, a mutant yeast strain in which two of the three CLN genes (CLN1 and CLN2) were inactive and expression of the third was conditional, was used to identify human cDNA clones which rescue yeast from CLN deficiency. A human glioblastoma cDNA library carried in a yeast expression vector (pADNS) was introduced into the mutant yeast strain. Two yeast transformants (pCYCD1-21 and pCYCD1-19) which grew despite the lack of function of all three CLN genes and were not revertants, were identified and recovered in *E. coli*. Both rescued the mutant (CLN deficient) strain when reintroduced into yeast, although rescue was inefficient and the rescued strain grew relatively poorly.

pCYCD1-19 and pCYCD1-21 were shown, by restriction mapping and partial DNA sequence analysis, to be independent clones representing the same gene. A HeLa cDNA library was screened for a full length cDNA clone, using the 1.2 kb insert of pCYCD1-21 as probe. Complete sequencing was done of the longest of nine positive clones identified in this manner (pCYCD1-H12; 1325 bp). The sequence of the 1.2 kb insert is presented in FIG. 2; the predicted protein product of the gene is of approximate molecular weight 34,000 daltons.

Cyclin D2 and cyclin D3 cDNAs were isolated using the polymerase chain reaction and three oligonucleotide probes derived from three highly conserved regions of D-type cyclins, as described in Example 4. As described, two 5' oligonucleotides and one 3' degenerate oligonucleotide were used for this purpose. The nucleotide and amino acid sequences of the CCND2 gene and encoded D2 cyclin protein are represented in FIG. 3 and of the CCND3 gene and encoded D3 cyclin protein are represented in FIG. 4. A deposit of plasmid pCYC-D3 was made with the American Type Culture Collection (Rockville, Md.) on May 14, 1991, under the terms of the Budapest Treaty. Accession number 68620 has been assigned to the deposit.

Comparison of the CYCD1-H12-encoded protein sequence with that of known cyclins (see FIG. 5A) showed that there was homology between the new cyclin and A, B and CLN type cyclins, but also made it clear that CYCD1 differs from these existing classes.

Figure 5B:
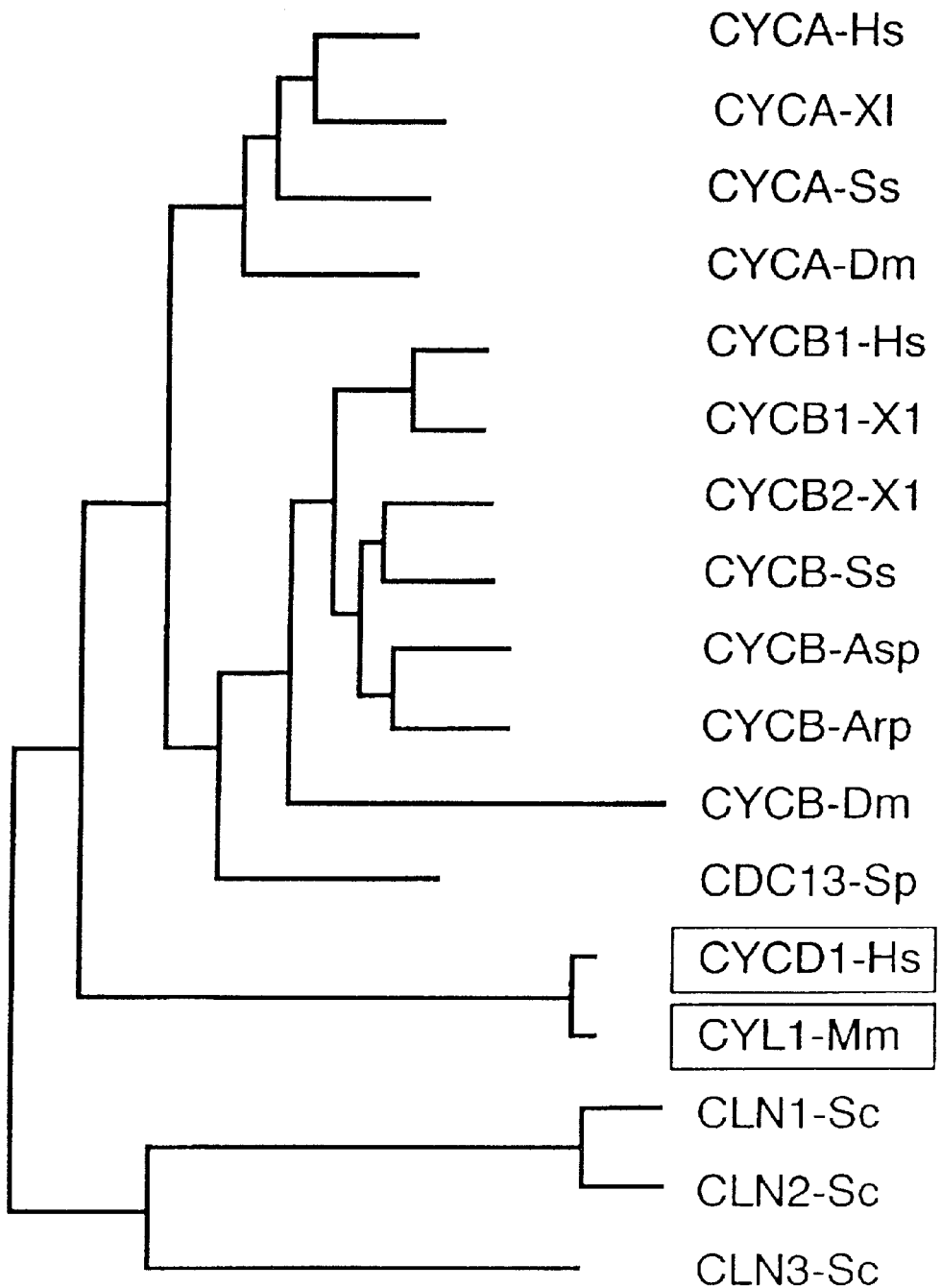
FIG. 5B is a schematic representation of the evolutionary tree of the cyclin family, constructed using the Neighbor-Joining method; the length of horizontal line reflects the divergence.

An assessment of how this new cyclin gene and its product might be related in an evolutionary sense to other cyclin genes was carried out by a comprehensive comparison of the amino acid sequences of all known cyclins (FIG. 5B and Example 1). Results of this comparison showed that CYCD1 represents a new class of cyclin, designated herein cyclin D.

Expression of cyclin D1 gene in human cells was studied using Northern analysis, as described in Example 2. Results showed that levels of cyclin D1 expression were very low in several cell lines. The entire coding region of the CYCD1 gene was used to probe poly(A)+RNA from HeLa cells and demonstrated the presence of two major transcripts, one approximately 4.8 kb and the other approximately 1.7 kb, with the higher molecular weight form being the more abundant. Most of the cDNA clones isolated from various cDNA libraries proved to be very similar to clone λCYCD1-H12 and, thus, it appears that the 1.7 kb transcript detected in Northern blots corresponds to the nucleotide sequence of FIG. 2. The origin of the larger (4.8 kb) transcript was unclear. As described in Example 2, it appears that the two mRNAs detected (4.8 kb and 1.7 kb) arose by differential polyadenylation of CYCD1 (FIG. 6).

Differential expression of cyclin D1 in different tissues and cell lines was also assessed, as described in Example 3. Screening of cDNA libraries to obtain full length CYCD1 clones had demonstrated that the cDNA library from the human glioblastoma cell line (U118 MG) used to produce yeast transformants produced many more positives than the other three cDNA libraries (human HeLa cell cDNA, human T cell cDNA, human teratocarcinoma cell cDNA). Northern and Western blotting were carried out to determine whether cyclin D1 is differentially expressed. Results showed (Example 3) that the level of transcript is 7 to 10 fold higher in the glioblastoma (U118 MG) cells than in HeLa cells, and that in both HeLa and U118 MG cells, the high and low molecular weight transcripts occurred. Western blotting using anti-CYL1 antibody readily detected the presence of a 34 kd polypeptide in the glioblastoma cells and demonstrated that the protein is far less abundant in HeLa cells and not detectable in the 293 cells. The molecular weight of the anti-CYCL1 cross reactive material identified in U118 MG and HeLa cells is exactly that of the human CYCD1 protein expressed in *E. coli*. Thus, results demonstrated differential occurrence of the cyclin D1 in the cell types analyzed, with the highest levels being in cells of neural origin.

As also described herein (Example 6), human genomic libraries were screened using cDNA probes and genomic clones of human D-type cyclins, specifically D1, D2 and D3, have been isolated and characterized. Nucleic acid sequences of cyclin D1, D2 and D3 promoters are represented in FIGS. 11–13. Specifically, the entire 1.3 kb cyclin D1 cDNA clone was used as a probe to screen a normal human liver genomic library, resulting in identification of three positive clones. One of these clones (G6) contained a DNA insert shown to contain 1150 bp of upstream promoter sequence and a 198 bp exon, followed by an intron. Lambda genomic clones corresponding to the human cyclin D2 and lambda genomic clones corresponding to the human cyclin D3 were also isolated and characterized, using a similar approach. One clone (γD2-G4) was shown to contain (FIG. 8B) a 2.7 kb SacI SmaI fragment which includes 1620 bp of sequence 5' to the presumptive initiating methionine codon identified in D2 cDNA (FIG. 3) and a 195 bp exon followed by a 907 bp intervening sequence. One clone (G9) was shown to contain (FIG. 8C) 1.8 kb of sequence 5' to the presumptive initiating methionine codon identified in D3 cDNA (FIG. 4), a 198 bp exon 1, a 684 bp exon 2 and a 870 bp intron.

Thus, as a result of the work described herein, a novel class of mammalian cyclins, designated cyclin D or D-type cyclin, has been identified and shown to be distinct, on the basis of structure of the gene (protein) product, from previously-identified cyclins. Three members of this new class, designated cyclin D1 or CCND1, cyclin D2 or CCND2 and cyclin D3 or CCND3, have been isolated and sequenced. They have been shown to fulfill the role of another cyclin (CLN type) in activation of the protein kinase (CDC28) which is essential for cell cycle start in yeast. It has also been shown that the cyclin D1 gene is expressed differentially in different cell types, with expression being highest in cells of neural origin.

Uses of the Invention

It is possible, using the methods and materials described herein, to identify genes (DNA or RNA) which encode other cyclins (DNA or RNA which replaces a gene essential for cell cycle start). This method can be used to identify additional members of the cyclin D class or other (non-D type) cyclins of either human or nonhuman origin. This can be done, for example, by screening other cDNA libraries using the budding yeast strain conditional for CLN cyclin expression, described in Example 1, or another mutant in which the ability of a gene to replace cyclin expression can be assessed and used to identify cyclin homologues. This method is carried out as described herein, particularly in Example 1 and as represented in FIG. 1. A cDNA library carried in an appropriate yeast vector (e.g., pADNS) is introduced into a mutant yeast strain, such as the strain described herein (Example 1 and Experimental Procedures). The strain used contains altered CLN genes. In the case of the specific strain described herein, insertional mutations in the CLN1 and CLN2 genes rendered them inactive and alteration of the CLN3 gene allowed for its conditional expression from a galactose-inducible, glucose-repressible promoter; as exemplified, this promoter is a galactose-inducible, glucose-repressible promoter but others can be used.

Mutant yeast transformed with the cDNA library in the expression vector are screened for their ability to grow on glucose-containing medium. In medium containing galactose, the CLN3 gene is expressed and cell viability is maintained, despite the absence of CLN1 and CLN2. In medium containing glucose, all CLN function is lost and the yeast cells arrest in the G1 phase of the cell cycle. Thus, the ability of a yeast transformant to grow on glucose-containing medium is an indication of the presence in the transformant of DNA able to replace the function of a gene essential for cell cycle start. Although not required, this can be confirmed by use of an expression vector, such as pADNS, which contains a selectable marker (the LEU2 marker is present in pADNS). Assessment of the plasmid stability shows whether the ability to grow on glucose-containing medium is the result of reversion or the presence of DNA function (introduction of DNA which replaces the unexpressed or nonfunctional yeast gene(s) essential for cell cycle start). Using this method, cyclins of all types (D type, non-D type) can be identified by their ability to replace CLN3 function when transformants are grown on glucose.

Screening of additional cDNA or genomic libraries to identify other cyclin genes can be carried out using all or a portion of the human D-type cyclin DNAs disclosed herein as probes; for example, all or a portion of the D1, D2 or D3 cDNA sequences of FIGS. 2–4, respectively, or all or a portion of the corresponding genomic sequences described herein can be used as probes. The hybridization conditions can be varied as desired and, as a result, the sequences identified will be of greater or lesser complementarity to the probe sequence (i.e., if higher or lower stringency conditions are used). Additionally, an anti-D type cyclin antibody, such as CYL1 or another raised against D1 or D3 or other human D-type cyclin, can be used to detect other recombinant D-type cyclins produced in appropriate host cells transformed with a vector containing DNA thought to encode a cyclin.

Based on work described herein, it is possible to detect altered expression of a D-type cyclin or increased rates of cell division in cells obtained from a tissue or biological sample, such as blood, urine, feces, mucous or saliva. This has potential for use for diagnostic and prognostic purposes since, for example, there appears to be a link between alteration of a cyclin gene expression and cellular transformation or abnormal cell proliferation. For example, several previous reports have suggested the oncogenic potential of altered human cyclin A function. The human cyclin A gene was found to be a target for hepatitis B virus integration in a hepatocellular carcinoma (Wand, J. et al., *Nature* 343:555–557 (1990)). Cyclin A has also been shown to associate with adenovirus E1A in virally infected cells (Giordano, A et al., *Cell* 58:981–990 (1989); Pines, J. and T.

Hunter, *Nature* 346:760–763 (1990)). Further, the PRAD1 gene, which has the same sequence as the cyclin D1 gene, may play an important role in the development of various tumors (e.g., non-parathyroid neoplasis, human breast carcinomas and squamous cell carcinomas) with abnormalities in chromosome 11q13. In particular, identification of CCND1 (PRAD1) as a candidate BCL1 oncogene provides the most direct evidence for the oncogenic potential of cyclin genes. This also suggests that other members of the D-type cyclin family may be involved in oncogenesis. In this context, the chromosomal locations of the CCND2 and CCND3 genes have been mapped to 12p13 and 6p21, respectively. Region 12p13 contains sites of several translocations that are associated with specific immunophenotypes of disease, such as acute lymphoblastic leukemia, chronic myelomoncytic leukemia, and acute myeloid leukemia. Particularly, the isochromosome of the short arm of chromosome 12 [1(12p)] is one of a few known consistent chromosomal abnormalities in human solid tumors and is seen in 90% of adult testicular germ cell tumors. Region 6p21, on the other hand, has been implicated in the manifestation of chronic lymphoproliferative disorder and leiomyoma. Region tp21, the locus of HLA complex, is also one of the best characterized regions of the human genome. Many diseases have been previously linked to the KLA complex, but the etiology of few of these diseases is fully understood. Molecular cloning and chromosomal localization of cyclins D2 and D3 should make it possible to determine whether they are directly involved in these translocations, and if so, whether they are activated. If they prove to be involved, diagnostic and therapeutic methods described herein can be used to assess an individual's disease state or probability of developing a condition associated with or caused by such translocations, to monitor therapy effectiveness (by assessing the effect of a drug or drugs on cell proliferation) and to provide treatment.

The present invention includes a diagnostic method to detect altered expression of a cyclin gene, such as cyclin D1, D2, D3 or another D-type cyclin. The method can be carried out to detect altered expression in cells or in a biological sample. As shown herein, there is high sequence similarity among cyclin D genes, which indicates that different members of D-type cyclins may use similar mechanisms in regulating the cell cycle (e.g., association with the same catalytic subunit and acting upon the same substrates). The fact that there is cell-type-specific differential expression, in both mouse and human cells, makes it reasonable to suggest that different cell lineages or different tissues may use different D-type cyclins to perform very similar functions and that altered tissue-specific expression of cyclin D genes as a result of translocation or other mutational events may contribute to abnormal cell proliferation. As described herein, cyclin D1 is expressed differentially in tissues analyzed; in particular, it has been shown to be expressed at the highest levels in cells of neural origin (e.g., glioblastoma cells).

As a result of the work described herein, D-type cyclin expression can be detected and/or quantitated and results used as an indicator of normal or abnormal (e.g., abnormally high rate of) cell division. Differential expression (either expression in various cell types or of one or more of the types of D cyclins) can also be determined.

In a diagnostic method of the present invention, cells obtained from an individual are processed in order to render nucleic acid sequences in them available for hybridization with complementary nucleic acid sequences. All or a portion of the D1, D2 and/or D3 cyclin (or other D-type cyclin gene) sequences can be used as a probe(s). Such probes can be a portion of a D-type cyclin gene; such a portion must be of sufficient length to hybridize to complementary sequences in a sample and remain hybridized under the conditions used and will generally be at least six nucleotides long. Hybridization is detected using known techniques (e.g., measurement of labeled hybridization complexes, if radiolabeled or fluorescently labeled oligonucleotide probed are used). The extent to which hybridization occurs is quantitated; increased levels of the D-type cyclin gene is indicative of increased potential for cell division.

Alternatively, the extent to which a D-type cyclin (or cyclins) is present in cells, in a specific cell type or in a body fluid can be determined using known techniques and an antibody specific for the D-type cyclin(s). In a third type of diagnostic method, complex formation between the D-type cyclin and the protein kinase with which it normally or typically complexes is assessed, using exogenous substrate, such as histone H1, as a substrate. Arion, D. et al., *Cell*, 55:371–378 (1988). In each diagnostic method, comparison of results obtained from cells or a body fluid being analyzed with results obtained from an appropriate control (e.g., cells of the same type known to have normal D-type cyclin levels and/or activity or the same body fluid obtained from an individual known to have normal D-type cyclin levels and/or activity) is carried out. Increased D-type cyclin levels and/or activity may be indicative of an increased probability of abnormal cell proliferation or oncogenesis or of the actual occurrence of abnormal proliferation or oncogenesis. It is also possible to detect more than one type of cyclin (e.g., A, B, and/or D) in a cell or tissue sample by using a set of probes (e.g., a set of nucleic acid probes or a set of antibodies), the members of which each recognize and bind to a selected cyclin and collectively provide information about two or more cyclins in the tissues or cells analyzed. Such probes are also the subject of the present invention; they will generally be detectably labelled (e.g., with a radioactive label, a fluorescent material, biotin or another member of a binding pair or an enzyme).

A method of inhibiting cell division, particularly cell division which would otherwise occur at an abnormally high rate, is also possible. For example, increased cell division is reduced or prevented by introducing into cells a drug or other agent which can block, directly or indirectly, formation of the protein kinase-D type cyclin complex and, thus, block activation of the enzyme. In one embodiment, complex formation is prevented in an indirect manner, such as by preventing transcription and/or translation of the D-type cyclin DNA and/or RNA. This can be carried out by introducing antisense oligonucleotides into cells, in which they hybridize to the cyclin-encoding nucleic acid sequences, preventing their further processing. It is also possible to inhibit expression of the cyclin by interfering with an essential D-type transcription factor. There are reasons to believe that the regulation of cyclin gene transcription may play an important role in regulating the cell cycle and cell growth and oscillations of cyclin mRNA levels are critical in controlling cell division. The G1 phase is the time at which cells commit to a new round of division in response to external and internal sequences and, thus, transcription factors which regulate expression of G1 cyclins are surely important in controlling cell proliferation. Modulation of the transcription factors is one route by which D-type cyclin activity can be influenced, resulting, in the case of inhibition or prevention of function of the transcription factor(s), in reduced D-type cyclin activity. Alternatively, complex formation can be prevented indirectly by degrading the D-type cyclin(s), such as by introducing a protease or substance which enhances cyclin breakdown into cells. In either case, the effect is indirect in that less D-type cyclin is available than would otherwise be the case.

In another embodiment, protein kinase-D type cyclin complex formation is prevented in a more direct manner by, for example, introducing into cells a drug or other agent which binds the protein kinase or the D-type cyclin or otherwise interferes with the physical association between the cyclin and the protein kinase it activates (e.g., by intercalation) or disrupts the catalytic activity of the enzyme. This can be effected by means of antibodies which bind the kinase or the cyclin or a peptide or low molecular weight organic compound which, like the endogenous D-type cyclin, binds the protein kinase, but whose binding does not result in activation of the enzyme or results in its being disabled or degraded. Peptides and small organic compounds to be used for this purpose can be designed, based on analysis of the amino acid sequences of D-type cyclins, to include residues necessary for binding and to exclude residues whose presence results in activation. This can be done, for example, by systematically mapping the binding site(s) and designing molecules which recognize or otherwise associate with the site(s) necessary for activation, but do not cause activation. As described herein, there is differential expression in tissues of D-type cyclins. Thus, it is possible to selectively decrease mitotic capability of cells by the use of an agent (e.g., an antibody or anti-sense or other nucleic acid molecule) which is designed to interfere with (inhibit) the activity and/or level of expression of a selected type (or types) of D cyclin. For example, in treating tumors involving the central nervous system or other non-hemotopoietic tissues, agents which selectively inhibit cyclin D1 might be expected to be particularly useful, since D1 has been shown to be differentially expressed (expressed at particularly high levels in cells of neural origin).

Antibodies specifically reactive with D-type cyclins of the present invention can also be produced, using known methods. For example, anti-D type cyclin antisera can be produced by injecting an appropriate host (e.g., rabbits, mice, rats, pigs) with the D-type cyclin against which anti sera is desired and withdrawing blood from the host animal after sufficient time for antibodies to have been formed. Monoclonal antibodies can also be produced using known techniques. Sambrook, J. et al., *Molecular Cloning: A Laboratory Manual*, Cold Spring Harbor Laboratory, Cold Spring Harbor, N.Y. (1989).

The present invention also includes a method of screening compounds or molecules for their ability to inhibit or suppress the function of a cyclin, particularly a D-type cyclin. For example, mutant cells as described herein, in which a D-type cyclin such as D1 or D3, is expressed, can be used. A compound or molecule to be assessed for its ability to inhibit a D-type cyclin is contacted with the cells, under conditions appropriate for entry of the compound or molecule into the cells. Inhibition of the cyclin will result in arrest of the cells or a reduced rate of cell division. Comparison of the rate or extent of cell division in the presence of the compound or molecule being assessed with cell division of an appropriate control (e.g., the same type of cells without added test drug) will demonstrate the ability or inability of the compound or molecule to inhibit the cyclin. Existing compounds or molecules (e.g., those present in a fermentation broth or a chemical "library") or those developed to inhibit the cyclin activation of its protein kinase can be screened for their effectiveness using this method. Drugs which inhibit D-type cyclin are also the subject of this invention.

The present invention will now be illustrated by the following examples, which are not intended to be limiting in any way.

EXAMPLES

Experimental procedures for Examples 1–3 are presented after Example 3.

Example 1

Identification of Human cDNA Clones that Rescue CLN Deficiency

In *S. cerevisiae*, there are three Cln proteins. Disruption of any one CLN gene has little effect on growth, but if all three CLN genes are disrupted, the cells arrest in G1 (Richardson, H. E. et al., *Cell* 59:1127–1133 (1989)). A yeast strain was constructed, as described below, which contained insertional mutations in the CLN1 and CLN2 genes to render them inactive. The remaining CLN3 gene was further altered to allow for conditional expression from the galactose-inducible, glucose-repressible promoter GAL1 (see FIG. 1). The strain is designated 305-15d #21. In medium containing galactose the CLN3 gene is expressed and despite the absence of both CLN1 and CLN2, cell viability is retained (FIG. 1). In a medium containing glucose, all CLN function is lost and the cells arrest in the G1 phase of the cell cycle.

A human glioblastoma cDNA library carried in the yeast expression vector pADNS (Colicelli, J. et al., *Pro. Natl. Acad. Sci. USA* 86:3599–3603 (1989)) was introduced into the yeast. The vector pADNS has the LEU2 marker, the $2\mu$ replication origin, and the promoter and terminator sequences from the yeast alcohol dehydrogenase gene (FIG. 1). Approximately $3 \times 10^6$ transformants were screened for the ability to grow on glucose containing medium. After 12 days of incubation, twelve colonies were obtained. The majority of these proved to be revertants. However, in two cases, the ability to grow on glucose correlated with the maintenance of the LEU2 marker as assessed by plasmid stability tests. These two yeast transformants carried plasmids designated pCYCD1-21 and pCYCD1-19 (see below). Both were recovered in *E. coli*. Upon reintroduction into yeast, the plasmids rescued the CLN deficient strain, although the rescue was inefficient and the rescued strain grew relatively poorly.

The restriction map and partial DNA sequence analysis revealed that pCYCD1-19 and pCYCD1-21 were independent clones representing the same gene. The 1.2 kb insert of pCYCD1-21 was used as probe to screen a human HeLa cDNA library for a full length cDNA clone. Approximately 2 million cDNA clones were screened and 9 positives were obtained. The longest one of these clones, pCYCD1-H12 (1325 bp), was completely sequenced (FIG. 2). The sequence exhibits a very high GC content within the coding region (61%) and contains a poly A tail (69 A residues). The estimated molecular weight of the predicted protein product of the gene is 33,670 daltons starting from the first in-frame AUG codon at nucleotide 145 (FIG. 2). The predicted protein is related to other cyclins (see below) and has an unusually low pI of 4.9 (compared to 6.4 of human cyclin A, 7.7 of human cyclin B and 5.6 of CLN1), largely contributed by the high concentration of acidic residues at its C-terminus.

There are neither methionine nor stop codons 5' to the predicted initiating methionine at nucleotide 145. Because of this and also because of the apparent N-terminal truncation of CYCD1 with respect to other cyclins (see below for more detail), four additional human cDNA libraries were further screened to see if the λCYCD1-H12 clone might lack the full 5' region of the cDNA. Among more than 100 cDNA clones isolated from these screens, none was found that had a more extensive 5' region than that of λCYCD1-H12. The full length coding capacity of clone H12 was later confirmed by Western blot analysis (see below).

CYCD1 encodes the smallest (34 kd) cyclin protein identified so far, compared to the 49 kd human cyclin A, 50 kd human cyclin B and 62 kd S. cerevisiae CLN1. By comparison with A and B type cyclins, the difference is due to the lack of almost the entire N-terminal segment that contains the so called "destruction box" identified in both A and B type cyclins (Glotzer, M. et al., Nature 349:132–138 (1991)).

Sequence Analysis of D1 and Comparison with Other Cyclins

Sequence analysis revealed homology between the CYCD1-H12 encoded protein and other cyclins. However, it is clear that CYCD1 differs from the three existing classes of cyclins, A, B and CLN. To examine how this new cyclin gene might be evolutionary related to other cyclins, a comprehensive amino acid sequence comparison of all cyclin genes was conducted. Fifteen previously published cyclin sequences as well as CYCD1 were first aligned using a strategy described in detail by Xiong and Eickbush (Xiong, Y. and T. H. Eickbush, EMBO J. 9:3353–3362 (1990)). Effort was made to reach the maximum similarity between sequences with the minimum introduction of insertion/deletions and to include as much sequence as possible. With the exception of CLN cyclins, this alignment contains about 200 amino acids residues which occupies more than 70% of total coding region of CYCD1 (FIG. 5A). There is a conserved domain and some scattered similarities between members of A and B type cyclins N-terminal to the aligned region (Glotzer, M. et al., Nature 349:132–138 (1991)), but this is not present in either CLN cyclins or CYCD1 and CYL1 and so they were not included in the alignment.

The percent divergence for all pairwise comparisons of the 17 aligned sequences was calculated and used to construct an evolutionary tree of cyclin gene family using the Neighbor-Joining method (Saitou, N. and M. Nei, Mol. Biol. Evol. 4:406–425 (1987) and Experimental Procedures). Because of the lowest similarity of CLN cyclins to the other three classes, the tree (FIG. 5B) was rooted at the connection between the CLN cyclins and the others. It is very clear from this evolutionary tree that CYCD1, CYCD2 and CYCD3 represent a distinct new class of cyclin, designated cyclin D.

Example 2

Expression of the Cyclin D1 Gene in Human Cells

Expression of cyclin D1 gene in human cells was studied by Northern analysis. Initial studies indicated that the level of cyclin D1 expression was very low in several cell lines. Poly (A)+RNA was prepared from HeLa cells and probed with the entire coding region of CYCD1 gene. Two major transcripts of 4.8 kb and 1.7 kb were detected. The high molecular weight form was the most abundant. With the exception of a few cDNA clones, which were truncated at either the 5' or 3' ends, most of the cDNA clones isolated from various different cDNA libraries are very similar to the clone λCYCD1-H12 (FIG. 2). Thus, it appears that the 1.7 kb transcript detected in Northern blots corresponds to nucleotide sequence in FIG. 2.

To understand the origin of the larger 4.8 kb transcript, both 5' and 3' end sub-fragments of the λCYCD1-H12 clone were used to screen both cDNA and genomic libraries, to test whether there might be alternative transcription initiation, polyadenylation and/or mRNA splicing. Two longer cDNA clones, λCYCD1-H034 (1.7 kb) from HeLa cells and λDYDC1-T078 (4.1 kb) from human teratocarcinoma cells, as well as several genomic clones were isolated and partially sequenced. Both λCYCD1-H034 and λCYCD1-T078 have identical sequences to λCYCD1-H12 clone from their 5' ends (FIG. 6). Both differ from λCYCD1-H12 in having additional sequences at the 3' end, after the site of polyadenylation. These 3' sequences are the same in λCYCD1-H034 and λCYCD1-T078, but extend further in the latter clone (FIG. 6). Nucleotide sequencing of a genomic clone within this region revealed colinearity between the cDNAs and the genomic DNA (FIG. 6). There is a single base deletion (an A residue) in λCYCD1-T078 cDNA clone. This may be the result of polymorphism, although it is not possible to exclude the possibility that some other mechanism is involved. The same 4.8 kb transcript, but not the 1.7 kb transcript, was detected using the 3' end extra fragment from clone T078 as a probe.

It appears that the two mRNAs detected in Northern blots arise by differential polyadenylation (FIG. 6). Strangely, there is no recognizable polyadenylation sequence (AAUAAA) anywhere within the sequence of clone λCYCD1-H12, even though polyadenylation has clearly occurred (FIG. 2). There is also no close variant of AAUAAA (nothing with less than two mismatches).

Example 3

Differential Expression of Cyclin D1 Gene in Different Cell Types

During the screening of cDNA libraries to obtain full length clones of CYCD1, it became evident that the cDNA library derived from the human glioblastoma cell line (U118 MG) from which the yeast transformants were obtained gave rise to many more positives than the other four cDNA libraries. Northern and Western blotting were carried out to explore the possibility that cyclin D1 might be differentially expressed in different tissues or cell lines. Total RNA was isolated from U118 MG cells and analyzed by Northern blot using the CYCD1 gene coding region as probe. The level of transcript is 7 to 10 fold higher in the glioblastoma cells, compared to HeLa cells. In both HeLa and U118 MG cells, both high and low molecular weight transcripts are observed.

To investigate whether the abundant CYCD1 message in the U118 MG cell line is reflected at the protein level, cell extracts were prepared and Western blotting was performed using anti-CYL1 prepared against mouse CYL1 (provided by Matsushime, H. et al.). This anti-CYL1 antibody was able to detect nanogram quantities of recombinant CYCD1 on Western blots (data not shown), and was also able to detect CYCD1 in the original yeast transformants by immunoprecipitation and Western analysis. Initial experiments using total cell extracts, from HeLa, 293 or U118 MG cells failed to detect any signal. However, if the cell extracts were immunoprecipitated with the serum before being subjected to SDS-PAGE and immunoblotting, a 34 kd polypeptide was readily detected in U118 MG cells. The protein is far less abundant in HeLa cells and was not detectable in 293 cells. The molecular weight of the anti-CYCL1 cross-reactive material from U118 MG and HeLa is exactly that of the human CYCD1 protein expressed in E. coli. This argues that the sequenced cDNA clones contain the entire open reading frame.

EXPERIMENTAL PROCEDURES

Strain Construction

The parental strain was BF305-15d (MATa leu2-3 leu2-112 his3-11 his3-15 ura3-52 trp1 ade1 met14 arg5,6) (Futcher, B. and J. Carbon, *Mol. Cell. Biol.* 6:2213–2222 (1986)). The strain was converted into a conditional cln-strain in three steps. First, the chromosomal CLN3 gene was placed under control of the GAL1 promoter. A 0.75 kb EcoRI-BamHI fragment containing the bidirectional GAL10-GAL1 promoters was fused to the 5' end of the CLN3 gene, such that the BamHI (GAL1) end was attached 110 nucleotides upstream of the CLN3 start codon. An EcoRI fragment stretching from the GAL10 promoter to the middle of CLN3 (Nash, R. et al., *EMBO J.* 7:4335–4346 (1988)) was then subcloned between the XhoI and EcoRI sites of pBF30 (Nash, R. et al., *EMBO J.* 7:4335–4346 (1988)). The ligation of the XhoI end to the EcoRI end was accomplished by filling in the ends with Klenow, and blunt-end ligating (destroying the EcoRI site). As a result, the GAL1 promoter had replaced the DNA normally found between −110 and −411 upstream of CLN3. Next, an EcoRI to SphI fragment was excised from this new pBF30 derivative. This fragment had extensive 5' and 3' homology to the CLN3 region, but contained the GAL1 promoter and a URA3 marker just upstream of CLN3. Strain BF305-15d was transformed with this fragment and Ura+transformants were selected. These were checked by Southern analysis. In addition, average cell size was measured when the GAL1 promoter was induced or uninduced. When the GAL1 promoter was induced by growing the cells in 1% raffinose and 1% galactose, mode cell volume was about 25 $\mu m^3$ (compared to a mode volume of about 40 $\mu m^3$ for the parental strain) whereas when the promoter was not induced (raffinose alone), or was repressed by the presence of glucose, cell volume was much larger than for the wild-type strain. These experiments showed that CLN3 had been placed under control of the GAL1 promoter. It is important to note that this GAL1-controlled, glucose repressible gene is the only source of CLN3 protein in the cell.

Second, the CLN1 gene was disrupted. A fragment of CLN1 was obtained from I. Fitch, and used to obtain a full length clone of CLN1 by hybridization, and this was sub-cloned into a pUC plasmid. A BamHI fragment carrying the HIS3 gene was inserted into an NcoI site in the CLN1 open reading frame. A large EcoRI fragment with extensive 5' and 3' homology to the CLN1 region was then excised, and used to transform the BF305-15d GAL-CLN3 strain described above. Transformation was done on YNB-his raffinose galactose plates. His+ clones were selected, and checked by Southern analysis.

Finally, the CLN2 gene was disrupted. A fragment of CLN2 was obtained from I. Fitch, and used to obtain a full length clone of CLN2 by hybridization, and this was sub-cloned into a pUC plasmid. An EcoRI fragment carrying the TRP1 gene was inserted into an SpeI site in the CLN2 open reading frame. A BamHI-KpnI fragment was excised and used to transform the BF305-15d GAL-CLN3 HIS3::cln1 strain described above. Transformation was done on YNB-trp raffinose galactose plates. Trp+ clones were selected. In this case, because the TRP1 fragment included an ARS, many of the transformants contained autonomously replicating plasmid rather than a disrupted CLN2 gene. However, several percent of the transformants were simple TRP1::cln2 disruptants, as shown by phenotypic and Southern analysis.

One particular 305-15d GAL1-CLN3 HIS3::cln1 TRP1::cln2 transformant called clone #21 (referred to hereafter as 305-15d #21) was analyzed extensively. When grown in 1% raffinose and 1% galactose, it had a doubling time indistinguishable from the CLN wild-type parental strain. However, it displayed a moderate Wee phenotype (small cell volume), as expected for a CLN3 over-expressor. When glucose was added, or when galactose was removed, cells accumulated in G1 phase, and cell division ceased, though cells continued to increase in mass and volume. After overnight incubation in the G1-arrested state, essentially no budded cells were seen, and a large proportion of the cells had lysed due to their uncontrolled increase in size.

When 305-15d #21 was spread on glucose plates, revertant colonies arose at a frequency of about 10–7. The nature of these glucose-resistant, galactose-independent mutants was not investigated.

Yeast Spheroplasts Transformation

*S. cerevisae* spheroplasts transformation was carried out according to Burgers and Percival and Allshire (Burgers, P. M. J. and K. J. Percival, *Anal. Biochem.* 163:391–397 (1987); Allshire, R. C., *Proc. Natl. Acad. Sci. USA* 87:4043–4047 (1990)).

Cell Culture

HeLa and 293 cells were cultured at 37° C. either on plates or in suspension in Dulbecco's modified Eagle's medium (DMEM) supplemented with 10% fetal calf serum. Glioblastoma U118 MG cells were cultured on plates in DMEM supplemented with 15% fetal bovine serum and 0.1 mM non-essential amino acid (GIBCO).

Nucleic Acid Procedures

Most molecular biology techniques were essentially the same as described by Sambrook et al. (Sambrook, J. et al., *Molecular Cloning: A Laboratory Manual* Cold Spring Harbor Laboratory, Cold Spring Harbor, N.Y. (1989)). Phagmid vectors pUC118 or pUC119 (Vieira, J. and J. Messing, *Meth. Enzymol.* 153:3–11 (1987)) or pBlueScript (Stratagene) were used as cloning vectors. DNA sequences were determined either by a chain termination method (Sanger, F. et al., *Proc. Natl. Acad. Sci. USA* 74:5463–5467 (1977)) using Sequenase Kit (United States Biochemical) or on an Automated Sequencing System (373A, Applied Biosystems).

Human HeLa cell cDNA library in λZAP II was purchased from Stratagene. Human T cell cDNA library in λgt10 was a gift of M. Gillman (Cold Spring Harbor Laboratory). Human glioblastoma U118 MG and glioblastoma SW1088 cell cDNA libraries in λZAP II were gifts of M. Wigler (Cold Spring Harbor Laboratory). Human teratocarcinoma cell cDNA library λgt10 was a gift of Skowronski (Cold Spring Harbor Laboratory). Normal human liver genomic library λGEM-11 was purchased from Promega.

Total RNA from cell culture was extracted exactly according to Sambrook et al. (Sambrook, J. et al., *Molecular Cloning: A Laboratory Manual* Cold Spring Harbor Laboratory, Cold Spring Harbor, N.Y. (1989)) using guanidium thiocyanate followed by centrifugation in CsCl solution. Poly(A)+RNA was isolated from total RNA preparation using Poly (A)+Quick push columns (Stratagene). RNA samples were separated on a 1% agarose-formaldehyde-MOPS gel and transferred to a nitrocellulose filter. Northern hybridizations (as well as library screening) were carried out at 68° C. in a solution containing 5×Denhardt's solution, 2×SSC, 0.1% SDS, 100 μg/ml denatured Salmon sperm DNA, 25 μM NaPO$_4$ (pH7.0) and 10% dextran sulfate. Probes were labelled by the random priming labelling method (Feinberg, A. and B. Vogelstein, *Anal. Biochem.* 132:6–13 (1983)). A 1.3 kb Hind III fragment of cDNA clone pCYCD1-H12 was used as coding region probe for Northern hybridization and genomic library screening, a 1.7 kb Hind III-EcoRI fragment from cDNA clone pCYCD1-T078 was used as 3' fragment probe.

To express human cyclin D1 gene in bacteria, a 1.3 kb Nco I-Hind II fragment of pCYCD1-H12 containing the entire CYCD1 open reading frame was subcloned into a T7 expression vector (pET3d, Studier, F. W. et al., *Methods in Enzymology* 185:60–89 (1990)). Induction of *E. coli* strain BL21 (DE3) harboring the expression construct was according to Studier (Studier, F. W. et al., *Methods in Enzymology* 185:60–89 (1990)). Bacterial culture was lysed by sonication in a lysis buffer (5 mM EDTA, 10% glycerol, 50 mM Tris-HCL, pH 8.0, 0.005% Triton X-100) containing 6M urea (CYCD1 encoded p34 is only partial soluble in 8M urea), centrifuged for 15 minutes at 20,000 g force. The pellet was washed once in the lysis buffer with 6M urea, pelleted again, resuspended in lysis buffer containing 8M urea, and centrifuged. The supernatant which enriched the 34 kd CYCD1 protein was loaded on a 10% polyacrymide gel. The 34 kd band was cut from the gel and eluted with PBS containing 0.1% SDS.

Sequence Alignment and Formation of an Evolutionary Tree

Protein sequence alignment was conducted virtually by eye according to the methods described and discussed in detail by Xiong and Eickbush (Xiong, Y. and T. H. Eickbush, *EMBO J.* 9:3353–3362 (1990)). Numbers within certain sequences indicate the number of amino acid residues omitted from the sequence as the result of insertion.

Numbers within certain sequences indicate the number of amino acid residues omitted from the sequence as the result of insertion (e.g., for CLN1, . . . TWG25RLS . . . indicates that 25 amino acids have been omitted between G and R). Sources for each sequence used in this alignment and in the construction of an evolutionary tree (FIG. 5B) are as follows: CYCA-Hs, human A type cyclin (Wang, J. et al., *Nature* 343:555–557 (1990)); CYCA-X1, Xenopus A-type cyclin (Minshull, J. et al., *EMBO J.* 9:2865–2875 (1990)); CYCA-Ss, clam A-type cyclin (Swenson, K. I. et al., *Cell* 47:867–870 (1986); CYCA-Dm, Drosophila A-type cyclin (Lehner, C. F. and P. H. O'Farrell, *Cell* 56:957–968 (1989)); CYCB1-Hs, human B1-type cyclin (Pines, J. and T. Hunter, *Cell* 58:833–846 (1989)); CYCB1-X1 and CYCB2-X1, Xenopus B1- and B2-type cyclin (Minshull, J. et al., *Cell* 56:947–956 (1989)); CYCB-Ss, clam B-type cyclin (Westendorf, J. M et al., *J. Cell Biol.,* 108:1431–1444 (1989)); CYCB-Asp, starfish B-type cyclin (Tachibana, K. et al., *Dev. Biol.* 140:241–252 (1990)); CYCB-Arp, sea urchin B-type cyclin (Pines, J. and T. Hunter, *EMBO J.* 6:2987–2995 (1987)); CYCB-Dm, Drosophila B-type cyclin (Lehner, C. F. and P. H. O'Farrell, *Cell* 61:535–547 (1990)); CDC13-Sp, S. pombe CDC13 (Booher, R. and D. Beach, *EMBO J.* 7:2321–2327 (1988)); CLN1-Sc and CLN2-Sc, *S. cerevisiae* cyclin 1 and 2 (Hadwiger, J. A. et al., *Proc. Natl. Acad. Sci. USA* 86:6255–6259 (1989)); CLN3-Sc, *S. cerevisiae* cyclin 3 (Nash, R. et al., *EMBO J.* 7:4335–4346 (1988)).

A total of 17 cyclin sequences were aligned and two representive sequences from each class are presented in FIG. 5A.

Percent divergence of all pairwise comparison of 17 sequences were calculated from 154 amino acid residues common to all 17 sequences, which does not include the 50 residue segments located at N-terminal part of A, B and D-type cyclins because of its absence from CLN type cyclins. A gap/insertion was counted as one mismatch regardless of its size. Before tree construction, all values were changed to distance with Poisson correction (d=– $\log_e S$, where the S=sequence similarity (Nei, M., *Molecular Evolutionary Genetics* pp. 287–326 Columbia University Press, NY (1987)). Calculation of pairwise comparison and Poisson correction were conducted using computer programs developed at University of Rochester. Evolutionary trees of cyclin gene family was generated by the Neighbor-Joining program (Saitou, N. and M. Nei, *Mol. Biol. Evol.* 4:406–567 (1987)). All calculations were conducted on VAX computer MicroVMS V4.4 of Cold Spring Harbor Laboratory. The reliability of the tree was evaluated by using a subset sequence (e.g., A, B and D-type cyclins), including more residues (e.g., the 50-residue segment located at C-terminal of A, B and D-type cyclins, FIG. 5A) or adding several other unpublished cyclin sequences. They all gave rise to the tree with the same topology as the one presented in FIG. 5B.

Immunoprecipitation and Western Blots

Cells from 60 to 80% confluent 100 mm dish were lysed in 1 ml of lysis buffer (50 mM Tris-HCl, pH 7.4, 150 mM NaCl, 20 mM EDTA, 0.5% NP-40, 0.5% Nadeoxycholate, 1 mM PMSF) for 30 minutes on ice. Immunoprecipitation was carried out using 1 mg protein from each cell lysate at 4° C. for overnight. After equilibrated with the lysis buffer, 60 µl of Protein A-agarose (PIERCE) was added to each immunoprecipitation and incubated at 4° C. for 1 hour with constant rotating. The immunoprecipitate was washed three times with the lysis buffer and final resuspended in 50 µl 2×SDS protein sample buffer, boiled for 5 minutes and loaded onto a 10% polyacrymide gel. Proteins were transferred to a nitrocellulose filter using a SDE Electroblotting System (Millipore) for 45 minutes at a constant current of 400 mA. The filter was blocked for 2 to 6 hours with 1×PBS, 3% BSA and 0.1% sodium azide, washed 10 minutes each time and 6 times with NET gel buffer (50 mM Tris-HCl, pH 7.5, 150 mM NaCl, 0.1% NP-40, 1 mM EDTA, 0.25% gelatin and 0.02 sodium azide), radio-labelled with $^{125}$I-Protein A for 1 hour in blocking solution with shaking. The blot was then washed 10 minutes each time and 6 times with the NET gel buffer before autoradiography.

The tree was constructed using the Neighbor-Joining method (Saitou, N. and M. Nei, *Mol. Biol. Evol.,* 4:406–425 (1987). The length of horizontal line reflects the divergence. The branch length between the node connecting the CLN cyclins and other cyclins was arbitrary divided.

MATERIALS AND METHODS

The following materials and methods were used in the work described in Examples 4–6.

Molecular Cloning

The human HeLa cell cDNA library, the human glioblastoma cell U118 MG cDNA library, the normal human liver genomic library, and the hybridization buffer were the same as those described above. A human hippocampus cDNA library was purchased from Stratagene, Inc. High- and low-stringency hybridizations were carried out at 68° and 50° C., respectively. To prepare template DNA for PCR reactions, approximately 2 million lambda phages from each cDNA library were plated at a density of $10^5$ PFU/150-mm plate, and DNA was prepared from the plate lysate according to Sambrook, J. et al., *Molecular Cloning: A Laboratory Manual,* 2nd ed., Cold Spring Harbor Laboratory, Cold Spring Harbor, N.Y., 1989.

Example 4

Isolation of Human Cyclin D2 and D3 cDNAs

To isolate human cyclin D2 and D3 cDNAs, two 5' oligonucleotides and one 3' degenerate oligonucleotide were derived from three highly conserved regions of human CCND1, mouse cy11, cy12, and cy13 D-type cyclins (Matsushime, H. et al., *Cell* 65:701–713 (1991); Xiong, Y. et al., *Cell* 65:691–699; FIG. 8). The first 5' oligonucleotide primer, HCND11, is a 8192-fold degenerate 38-mer (TGGATG[T/C]TNGA[A/G]GTNTG[T/C]GA[A/C]GA[A/G]CA[A/G]AA[A/G]TG[T/C]GA[A/G]GA) (SEQ ID No. 37), encoding 13 amino acids (WMLEVCEEQKCEE) (SEQ ID No. 38). The second 5' oligonucleotide primer, HCND12, is a 8192-fold degenerate 29-mer (GTNTT[T/C]CCN[T/C]TNGCNATGAA[T/C]TA[T/C]TNGA) (SEQ ID No. 39), encoding 10 amino acids (VFPLAMNYLD) (SEQ ID No. 40). The 3' primer, HCND13, is a 3072-fold degenerate 24-mer ([A/G]TCNGT[A/G]TA[A/G/T]AT[A/G]CANA[A/G][T/C]TT-[T/C]TC) (SEQ ID No. 41), encoding 8 amino acids (EKLCIYTD) (SEQ ID No. 42). The PCR reactions were carried out for 30 cycles at 94° C. for 1 min, 48° C. for 1 min, and 72° C. for 1 min. The reactions contained 50 mM KCl, 10 mM Tris-HCl (pH 8.3), 1.5 mM $MgCl_2$, 0.01% gelatin, 0.2 mM each of dATP, dGTP, dCTP, and dTTP, 2.5 units of Taq polymerase, 5 μM of oligonucleotide, and 2–10 μg of template DNA. PCR products generated by HCND11 and HCND13 were verified in a second-round PCT reaction using HCND12 and HCND13 as the primers. After resolution on a 1.2% agarose gel, DNA fragments with the expected size (200 bp between primer HCND11 and HCND13) were purified and subcloned into the SmaI site of phagmid vector pUC118 for sequencing.

To isolate full-length cyclin D3 cDNA, the 201-bp fragment of the D3 PCR product was labeled with oligonucleotide primers HCND11 and HCND13 using a random-primed labeling technique (Feinberg, A. P. et al., *Anal. Biochem.* 132:6–13 (1983)) and used to screen a human HeLa cell cDNA library. The probe used to screen the human genomic library for the CCND3 gene was a 2-kb EcoRI fragment derived from cDNA clone λD3-H34. All hybridizations for the screen of human cyclin D3 were carried out at high stringency.

The PCR clones corresponding to CCND1 and CCND3 have been repeatedly isolated from both cDNA libraries; CCND2 has not. To isolate cyclin D2, a 1-kb EcoRI fragment derived from mouse cy12 cDNA was used as a probe to screen a human genomic library. Under low-stringency conditions, this probe hybridized to both human cyclins D1 and D2. The cyclin D1 clones were eliminated through another hybridization with a human cyclin D1 probe at high stringency. Human CCND2 genomic clones were subsequently identified by partial sequencing and by comparing the predicted protein sequence with that of human cyclins D1 and D3 as well as mouse cy12.

As described above, human CCND1 (cyclin D1) was isolated by rescuing a triple Cln deficiency mutant of *Saccharomyces cerevisiae* using a genetic complementation screen. Evolutionary proximity between human and mouse, and the high sequence similarity among cy11, cy12, and cy13, suggested the existence of two additional D-type cyclin genes in the human genome. The PCR technique was first used to isolate the putative human cyclin D2 and D3 genes. Three degenerate oligonucleotide primers were derived from highly conserved regions of human CCND1, mouse cy11, cy12, and cy13. Using these primers, cyclin D1 and a 200-bp DNA fragment that appeared to be the human homolog of mouse cy[13] from both human HeLa cell and glioblastoma cell cDNA libraries was isolated. A human HeLa cell cDNA library was screened with this PCR product as probe to obtain a full-length D3 clone. Some 1.2 million cDNA clones were screened, and six positives were obtained. The longest cDNA clone from this screen, λD3-H34 (1962 bp), was completely sequenced (FIG. 4).

Because a putative human cyclin D2 cDNA was not detected by PCR, mouse cy12 cDNA was used as a heterologous probe to screen a human cDNA library at low stringency. This resulted, initially, in isolation of 10 clones from the HeLa cell cDNA library, but all corresponded to the human cyclin D1 gene on the basis of restriction mapping. Presumably, this was because cyclin D2 in HeLa cells is expressed at very low levels. Thus, the same probe was used to screen a human genomic library, based on the assumption that the representation of D1 and D2 should be approximately equal. Of the 18 positives obtained, 10 corresponded to human cyclin D1 and 8 appeared to contain human cyclin D2 sequences (see below). A 0.4-kb BamHI restriction fragment derived from λD2-G1 1 of the 8 putative cyclin D2 clones, was then used as probe to screen a human hippocampus cDNA library at high stringency to search for a full-length cDNA clone of the cyclin D2 gene. Nine positives were obtained after screening of approximately 1 million cDNA clones. The longest cDNA clone, λD2-P3 (1911 bp), was completely sequenced (FIG. 3). Neither λD2-P3 nor λD3-H34 contains a poly(A) sequence, suggesting that part of the 3' untranslated region might be missing.

The DNA sequence of λD2-P3 revealed an open reading frame that could encode a 289-amino-acid protein with a 33,045-Da calculated molecular weight. A similar analysis of λD3-H34 revealed a 292-amino-acid open reading frame encoding a protein with a 32,482-Da calculated molecular weight. As in the case of human cyclin D1, there is neither methionine nor stop codons 5' to the presumptive initiating methionine codon for both λD2-P3 (nucleotide position 22, FIG. 3) and λD3-H34 (nucleotide position 101, FIG. 4). On the basis of the protein sequence comparison with human cyclin D1 and mouse cy11 (FIG. 7) and preliminary results of the RNase protection experiment, both λD2-P3 and λD3-H34 are believed to contain full-length coding regions.

The protein sequence of all 11 mammalian cyclins identified to date were compared to assess their structural and evolutionary relationships. This includes cyclin A, cyclins B1 and B2, six D-type cyclins (three from human and three from mouse), and the recently identified cyclins E and C (FIG. 7). Several features concerning D-type cyclins can be seen from this comparison. First, as noted previously for cyclin D1, all three cyclin D genes encode a similar small size protein ranging from 289 to 295 amino acid residues, the shortest cyclins found so far. Second, they all lack the so-called "destruction box" identified in the N-terminus of both A- and B-type cyclins, which targets it for ubiquitin-dependent degradation (Glotzer, M. et al., *Nature* 349:132–138 (1991)). This suggests either that the D-type cyclins have evolved a different mechanism to govern their periodic degradation during each cell cycle or that they do not undergo such destruction. Third, the three human cyclin D genes share very high similarity over their entire coding region: 60% between D1 and D2, 60% between D2 and D3, and 52% between D1 and D3. Fourth, members of the D-type cyclins are more closely related to each other than are members of the B-type cyclins, averaging 78% for three cyclin D genes in the cyclin box versus 57% for two cyclin B genes. This suggests that the separation (emergence) of D-type cyclins occurred after that of cyclin B1 from B2. Finally, using the well-characterized mitotic B-type cyclin as an index, the most closely related genes are cyclin A (average 51%), followed by the E-type (40%), D-type (29%), and C-type cyclins (20%).

Example 5

Chromosome Localization of CCND2 and CCND3

The chromosome localization of CCND2 and CCND3 was determined by fluorescence in situ hybridization. Chromosome in situ suppression hybridization and in situ hybridization banding were performed as described previously (Lichter, T. et al., Science 247:64–69 (1990); Baldini, A. et al., Genomics 9:770–774 (1991)). Briefly λD2-G4 and λD3-G9 lambda genomic DNAs containing inserts of 15 and 16 kb, respectively, were labeled with biotin-11-dUTP (Sigma) by nick-translation (Brigatti, D. J. et al., Urology 126:32–50 (1983); Boyle, A. L., In Current Protocols in Molecular Biology, Wiley, New York, 1991). Probe size ranged between 200 and 400 nucleotides, and unincorporated nucleotides were separated from probes using Sephadex G-50 spin columns (Sambrook, J. et al., Molecular Cloning: A Laboratory Manual, 2nd ed., Cold Spring Harbor Laboratory, Cold Spring Harbor, N.Y., 1989). Metaphase chromosome spreads prepared by the standard technique (Lichter, T. et al., Science 247:64–69 (1990)) were hybridized in situ with biotin-labeled D2-G4 or D3-G9. Denaturation and preannealing of 5 μg of DNase-treated human placental DNA, 7 μg of DNased salmon sperm DNA, and 100 ng of labeled probe were performed before the cocktail was applied to Alu prehybridized slides. The in situ hybridization banding pattern used for chromosome identification and visual localization of the probe was generated by cohybridizing the spreads with 40 ng of an Alu 48-mer oligonucleotide. This Alu oligo was chemically labeled with digoxigenin-11-dUTP (Boehringer-Mannheim) and denatured before being applied to denatured chromosomes. Following 16–18 h of incubation at 37° C. and posthybridization wash, slides were incubated with blocking solution and detection reagent (Lichter, T. et al., Science 247:64–69 (1990)). Biotin-labeled DNA was detected using fluorescence isothiocyanate (FITC)-conjugated avidin DCS (5 μg/ml) (Vector Laboratories); digoxigenin-labeled DNA was detected using a rhodamine-conjugated anti-digoxigenin antibody (Boehringer-Mannheim). Fluorescence signals were imaged separately using a Zeiss Axioskop-20 epifluorescence microscope equipped with a cooled CCD camera (Photometrics CH220). Camera control and image acquisition were performed using an Apple Macintosh IIX computer. The gray scale images were pseudocolored and merged electronically as described previously (Baldini, A. et al., Genomics 9:770–774 (1991)). Image processing was done on a Macintosh IIci computer using Gene Join Maxpix (software by Tim Rand in the laboratory of D. Ward, Yale) to merge FITC and rhodamine images. Photographs were taken directly from the computer monitor.

Chromosomal fluorescence in situ hybridization was used to localize D2-G4 and D3-G9. The cytogenetic location of D2-G4 on chromosome 12p band 13 and that of D3-G9 on chromosome 6p band 21 were determined by direct visualization of the two-color fluorescence in situ hybridization using the biotin-labeled probe and the digoxigen-labeled Alu 48-mer oligonucleotide (FIG. 5).

The Alu 48-mer R-bands, consistent with the conventional R-banding pattern, were imaged and merged with images generated from the D2-G4 and D3-G9 hybridized probes. The loci of D2-G4 and D3-G9 were visualized against the Alu banding by merging the corresponding FITC and rhodamine images. This merged image allows the direct visualization of D2-G4 and D3-G9 on chromosomes 12 and 6, respectively. The D2-G4 probe lies on the positive R-band 12p13, while D3-G9 lies on the positive R-band 6p21.

Cross-hybridization was not detected with either pseudogene cyclin D2 or D3, presumably because the potentially cross-hybridizing sequence represents only a sufficiently small proportion of the 15- and 16-kb genomic fragments (nonsuppressed) used as probe, and the nucleotide sequences of pseudogenes have diverged from their ancestral active genes.

Example 6

Isolation and Characterization of Genomic Clones of Human D-Type Cyclins

Figure 8A:
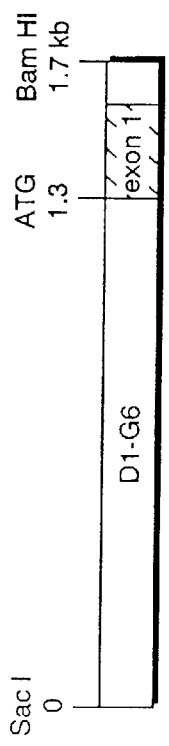
FIGS. 8A through 8C show a schematic representation of the genomic structure of human cyclin D genes, in which each diagram represents one restriction fragment from each cyclin D gene that has been completely sequenced. Solid boxes indicate exon sequences, open boxes indicate intron or 5' and 3' untranslated sequences and hatched boxes represent pseudogenes. The positions of certain restriction sites, ATG and stop codons are indicated at the top of each clone.
Figure 8B:
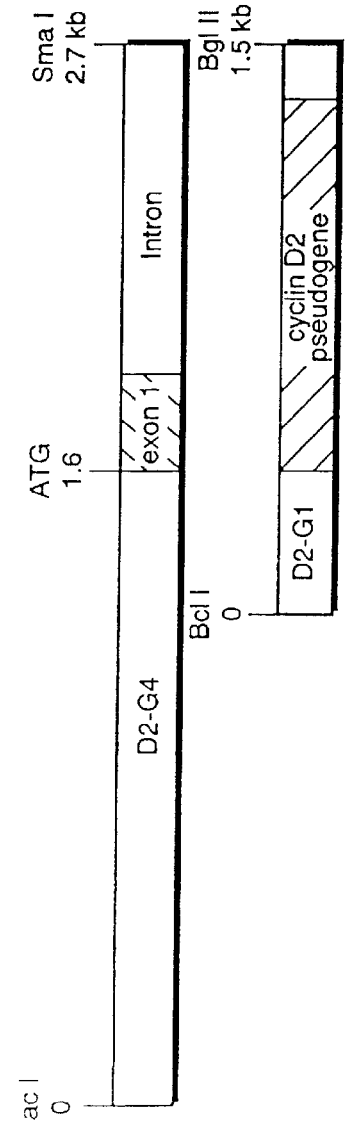
Figure 8C:
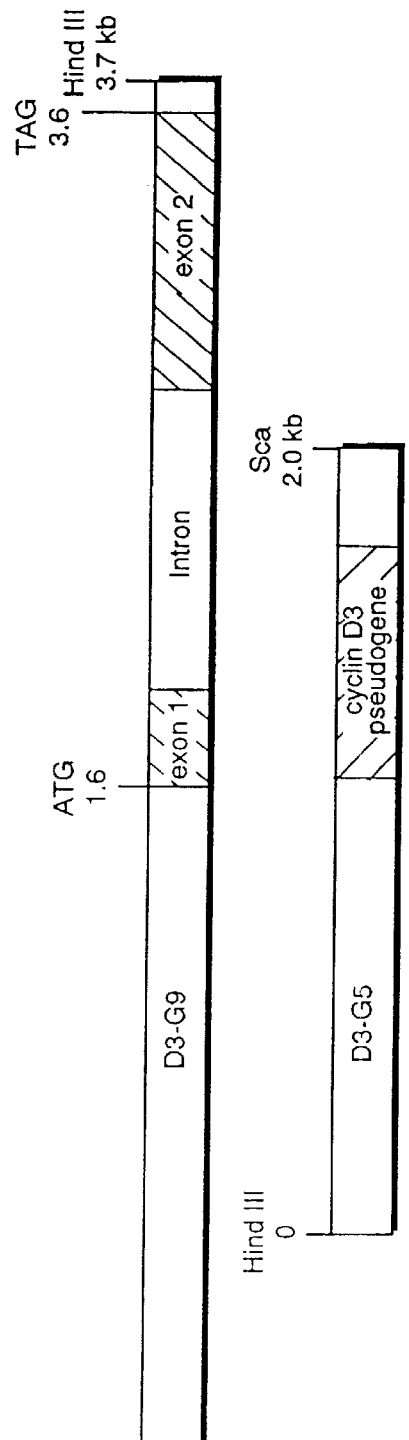

Genomic clones of human D-type cyclins were isolated and characterized to study the genomic structure and to obtain probes for chromosomal mapping. The entire 1.3-kb cyclin D1 cDNA clone was used as probe to screen a normal human liver genomic library. Five million lambda clones were screened, and three positives were obtained. After initial restriction mapping and hybridizations, lambda clone G6 was chosen for further analysis. A 1.7-kb BamHI restriction fragment of λD1-G6 was subcloned into pUC118 and completely sequenced. Comparison with the cDNA clones previously isolated and RNase protection experiment results (Withers, D. A. et al., Mol. Cell. Biol. 11:4846–4853 (1991)) indicated that this fragment corresponds to the 5' part of the cyclin D1 gene. As shown in FIG. 8A, it contains 1150 bp of upstream promoter sequence and a 198-bp exon followed by an intron.

Eighteen lambda genomic clones were isolated from a similar screening using mouse cyl2 cDNA as a probe under low-stringency hybridization conditions, as described above (Example 4). Because it was noted in previous cDNA library screening that the mouse cyl2 cDNA probe can cross-hybridize with the human D1 gene at low stringency, a dot-blot hybridization at high stringency was carried out, using the human D1 cDNA probe. Ten of the 18 clones hybridized with the human D1 probe and 8 did not. On the basis of the restriction digestion analysis, the 8 lambda clones that did not hybridize with the human D1 probe at high stringency fall into three classes respresented by λD2-G1, λD2-G2, and λD2-G4, respectively. These three lambda clones were subcloned into a pUC plasmid vector, and small restriction fragments containing coding region were identified by Southern hybridization using a mouse cyl2 cDNA probe. A 0.4-kb BamHI fragment derived from λD2-G1 was subsequently used as a probe to screen a human hippocampus cell cDNA library at high stringency. Detailed restriction mapping and partial sequencing indicated that λD2-G1 and λD2-G2 were two different clones corresponding to the same gene, whereas λD2-G4 appeared to correspond to a different gene. A 2.7-kb SacI-SmaI fragment from λD2-G4 and 1.5-kb BclI-BglII fragment from λD2-G1 have been completely sequenced. Nucleotide sequence comparison revealed that the clone λD2-G4 corresponds to the D2 cDNA clone λD2-P3 (FIG. 3). As shown in FIG. 8A, the 2.7-kb SacI-SmaI fragment contains 1620 bp of sequence 5' to the presumptive initiating methionine codon identified in D2 cDNA (FIG. 3) and a 195-bp exon followed by a 907-bp intervening sequence.

Lambda genomic clones corresponding to the human cyclin D3 were isolated from the same genomic library using human D3 cDNA as a probe. Of four million clones screened, nine were positives. Two classes of clones, represented by λD3-G4 and λD3-G9, were distinguished by restriction digestion analysis. A 2.0-kb HindIII-ScaI restriction fragment from λD3-G5 and a 3.7-kb SacI-HindIII restriction fragment from λD3-G9 were further subcloned into a pUC plasmid vector for more detailed restriction mapping and complete sequencing, as they both hybridized to the 5' cyclin D3 cDNA probe. As presented in FIG. 9C, the 3.7-kb fragment from clone G9 contains 1.8 kb of sequence 5' to the presumptive initiating methionine codon identified in D3 cDNA (FIG. 4), a 198-bp exon 1, a 684-bp exon 2, and a 870-bp intron.

Comparison of the genomic clones of cyclins D1, D2, and D3 revealed that the coding regions of all three human CCND genes are interrupted at the same position by an intron (indicated by an arrow in FIG. 8). This indicated that the intron occurred before the separation of cyclin D genes.

Example 7

Isolation and Characterization of Two Cyclin D Pseudogenes

The 1.5-kb BclI-BglII fragment subcloned from clone λD2-G1 has been completely sequenced and compared with cyclin D2 cDNA clone λD2-P3. As shown in FIG. 10, it contains three internal stop codons (nucleotide positions 495, 956, and 1310, indicated by asterisks), two frame-shifts (position 1188 and 1291, slash lines), one insertion, and one deletion. It has also accumulated many missense nucleotide substitutions, some of which occurred at the positions that are conserved in all cyclins. For example, triplet CGT at position 277 to 279 of D2 cDNA (FIG. 3) encodes amino acid Arg, which is an invariant residue in all cyclins (see FIG. 8). A nucleotide change from C to T at the corresponding position (nucleotide 731) in clone D2-G1 (FIG. 10) gave rise to a triplet TGT encoding Cys instead of Arg. Sequencing of the 2.0-kb HindIII-ScaI fragment from clone λD3-G5 revealed a cyclin D3 pseudogene (FIG. 11). In addition to a nonsense mutation (nucleotide position 1265), two frame-shifts (position 1210 and 1679), a 15-bp internal duplication (underlined region from position 1361 to 1376), and many missense mutations, a nucleotide change from A to G at position 1182 resulted in an amino acid change from the presumptive initiating methionine codon ATG to GTG encoding Val. On the basis of these analyses, we conclude that clones λD2-G1 and λD3-G5 contain pseudogenes of cyclins D2 and D3, respectively.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. Purified D-type cyclin comprising an amino acid sequence encoded by a nucleic acid which selectively hybrizes to the nucleic acid of SEQ ID NO: 1 under conditions of 2×SSC at 68° C. or higher stringency, which D-type cyclin has the function of a CLN-type protein essential for cell cycle start in budding yeast.

2. The cyclin of claim 1 which is encoded by a gene of mammalian origin.

3. The cyclin of claim 2 which is encoded by a gene of human origin.

4. Purified D-type cyclin comprising an amino acid sequence represented by SEQ ID NO: 2.

5. An antibody which specifically binds a D-type cyclin represented by SEQ ID NO. 2.

6. An antibody of claim 5, which antibody is a monoclonal antibody.

7. An antibody of claim 5, which antibody is labeled for detection of antigen-antibody complexes.

8. Isolated mammalian D1-type cyclin protein which is active in G1 phase and which has the function of a CLN gene essential for cell cycle start in budding yeast, which D1-type cyclin is encoded by a nucleic acid which selectively hybridizes, under conditions of 2×SSC at 68° C. or higher stringency to the nucleic acid represented by SEQ ID NO: 1.

9. Purified D1-type cyclin of human origin.

* * * * *